US012617835B2

(12) United States Patent
Prüss et al.

(10) Patent No.: US 12,617,835 B2
(45) Date of Patent: May 5, 2026

(54) CHIMERIC AUTOANTIBODY RECEPTOR (CAAR) THAT BINDS AUTOANTIBODIES TARGETING THE CENTRAL NERVOUS SYSTEM IN NEUROLOGICAL AUTOIMMUNE DISEASE

(71) Applicants: Deutsches Zentrum für Neurodegenerative Erkrankungen e. V. (DZNE), Bonn (DE); Max-Delbrück-Centrum für Molekulare Medizin in der Helmholtz-Gemeinschaft, Berlin (DE)

(72) Inventors: Harald Prüss, Berlin (DE); S. Momsen Reincke, Berlin (DE); Inan Edes, Berlin (DE)

(73) Assignees: Deutsches Zentrum für Neurodegenerative Erkrankungen e. V. (DZNE), Bonn (DE); Max-Delbrück-Centrum für Molekulare Medizin in der Helmholtz-Gemeinschaft, Berlin (DE)

( * ) Notice: Subject to any disclaimer, the term of this patent is extended or adjusted under 35 U.S.C. 154(b) by 1153 days.

(21) Appl. No.: 17/596,145

(22) PCT Filed: Jun. 5, 2020

(86) PCT No.: PCT/EP2020/065606
§ 371 (c)(1),
(2) Date: Dec. 3, 2021

(87) PCT Pub. No.: WO2020/245343
PCT Pub. Date: Dec. 10, 2020

(65) Prior Publication Data
US 2022/0298221 A1 Sep. 22, 2022

(30) Foreign Application Priority Data
Jun. 5, 2019 (EP) .................................... 19178541

(51) Int. Cl.
| | |
|---|---|
| *C12N 15/11* | (2006.01) |
| *A61K 31/506* | (2006.01) |
| *A61K 40/11* | (2025.01) |
| *A61K 40/31* | (2025.01) |
| *A61K 40/42* | (2025.01) |
| *A61P 25/28* | (2006.01) |
| *C07K 14/47* | (2006.01) |
| *C07K 14/705* | (2006.01) |
| *C07K 14/725* | (2006.01) |
| *C07K 16/28* | (2006.01) |
| *C07K 19/00* | (2006.01) |
| *C12N 5/0783* | (2010.01) |

(52) U.S. Cl.
CPC ........ *C07K 14/7051* (2013.01); *A61K 31/506* (2013.01); *A61K 40/11* (2025.01); *A61K 40/31* (2025.01); *A61K 40/4202* (2025.01); *A61P*

25/28 (2018.01); *C07K 14/4713* (2013.01); *C07K 14/70517* (2013.01); *C07K 16/286* (2013.01); *C12N 5/0636* (2013.01); *A61K 2239/48* (2023.05)

(58) Field of Classification Search
None
See application file for complete search history.

(56) References Cited

FOREIGN PATENT DOCUMENTS

| | | |
|---|---|---|
| WO | WO 2015/168613 A2 | 11/2015 |
| WO | WO 2015/177512 A1 | 11/2015 |
| WO | WO 2018/127584 A1 | 7/2018 |
| WO | WO 2018/127585 A1 | 7/2018 |
| WO | WO 2019/236593 A1 | 12/2019 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser: Boston, pp. 491-495.*
Skolnick et al.(2000). Trends in Biotech. 18(1):34-39.*
Greenfield, A. L., & Hauser, S. L. (2019). "Nucleic Acid-Based Therapeutics Relevant to Neuroimmune Conditions" Neurotherapeutics, 16: 314-318.

(Continued)

*Primary Examiner* — Christine J Saoud
*Assistant Examiner* — Jon M Lockard
(74) *Attorney, Agent, or Firm* — Knobbe, Martens, Olson & Bear, LLP

(57) ABSTRACT

A chimeric autoantibody receptor (CAAR) that enables targeting of an immune cell to autoantibody producing B cells. The CAAR includes an autoantigen or fragment thereof that is bound by autoantibodies associated with neurological autoimmune disease primarily targeting the central nervous system. Also disclosed is a nucleic acid molecule encoding a chimeric autoantibody receptor (CAAR), the nucleic acid sequence encoding an autoantigen or fragment thereof that is bound by autoantibodies associated with a neurological autoimmune disease primarily targeting the central nervous system, a transmembrane domain, and an intracellular signaling domain, a vector comprising a nucleic acid molecule encoding a chimeric autoantibody receptor (CAAR), a genetically modified immune cell comprising the nucleic acid molecule encoding the CAAR and use of the immune cell in the treatment or prevention of a neurological autoimmune disease primarily targeting the central nervous system, such as an autoimmune encephalopathy or encephalomyelopathy, preferably anti-NMDAR encephalitis.

11 Claims, 9 Drawing Sheets
Specification includes a Sequence Listing.

(56)                    References Cited

OTHER PUBLICATIONS

International Search Report in PCT/EP2020/065606 issued Sep. 16, 2020.
144th Annual Meeting American Neurological Association: "ANA 2019 Program Sunday Poster Presentations Autoimmune Neurology", dated Oct. 4, 2019.
Chatenoud, "Precision medicine for autoimmune disease", Nature Biotechnology, vol. 34, No. 9, dated Sep. 1, 2016, pp. 930-932.
Ellebrecht et al., "Reengineering chimeric antigen receptor T cells for targeted therapy of autoimmune disease", Science, vol. 353, No. 6295, dated Jul. 8, 2016, pp. 179-184.
Fransson et al., "CAR/FoxP3-engineered T regulatory cells target the CNS and suppress EAE upon intranasal delivery", Journal of Neuroinflammation, vol. 9, No. 1, dated Jan. 1, 2012, pp. 112.

Kreye et al., "Human cerebrospinal fluid monoclonal N-methyl-D-aspartate receptor autoantibodies are sufficient for encephalitis pathogenesis", Brain, vol. 139, No. 10, dated Aug. 20, 2016, pp. 2641-2652.
Ludwig et al., "Mechanisms of Autoantibody-Induced Pathology", Frontiers In Immunology, vol. 8, dated May 31, 2017, pp. 12-19.
McKee et al., "Recent Updates in Anti-NMDA Receptor Encephalitis Research—Rare Disease Review", Rare Disease Review, dated Feb. 1, 2017.
Ryan et al., "In vivo reprogramming of immune cells: Technologies for induction of antigen-specific tolerance", Advanced Drug Delivery Review, vol. 114, dated Apr. 14, 2017, pp. 240-255.
Tahir, "Is Chimeric Antigen Receptor T-cell Therapy the Future of Autoimmunity Management?", Cureus, dated Oct. 3, 2018.
Sharma, R., et al. "Membrane-bound and soluble forms of an NMDA receptor extracellular domain retain epitopes targeted in auto-immune encephalitis". BMC Biotechnol 18, 41 (2018).

* cited by examiner

A

CAAR-T-Cell        NMDAR-autoantibody        Specific depletion of
                                             autoantibody-producing B cells

B

CAAR-T-Cell        No binding                No effect

A

NMDA receptor

B

ATD-CAAR + HEK sIG-003-102          Control T cells + HEK sIG-003-102

CAAR T cell injection

Bioluminiscence Imaging – 10 min after D-Luciferin injection i.p.

Day:    -2  -1   0   1        5        8        12       15       19   22

NSG mice

IVIG    Nalm-6                      IVIG
i.p.    i.v.                       i.p.

i.v.: intravenous
i.p.: intraperitoneal

ATD-CAAR     ATD-S1-S2-CAAR     Control

Day 5 (pre-treatment)

Day 9 (4 days post-treatment)

Nalm6 #003-102

- ◆ - ATD-CAAR + Dasatinib
- ■ - ATD-CAAR
- ⊝ - ATD-S1-S2-CAAR + Dasatinib
- ▼ - ATD-S1-S2-CAAR Luciferase Killing Assay

- ▲ - control T cells vs. slg-003-102
- ■ - ATD-CAAR vs. slg-003-102 (50 µg/ml #003-102)
- ◆ - ATD-CAAR vs. slg-003-102 (10 µg/ml #003-102)
- ▼ - ATD-CAAR vs. slg-003-102

Figure 11:
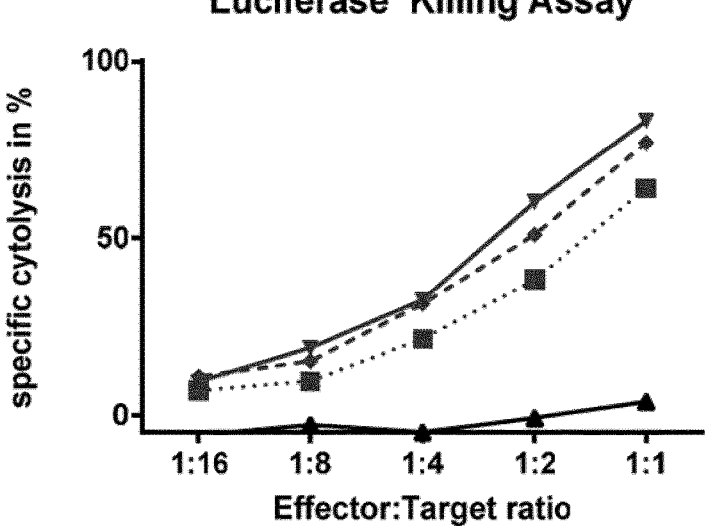

Fig. 11 (cont,)
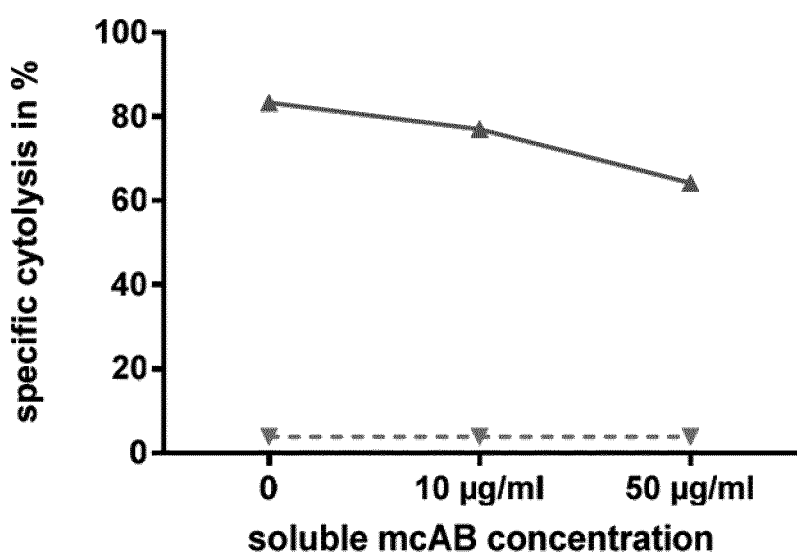
control T cells vs. sIg-003-102
ATD-CAAR vs. sIg-003-102

CHIMERIC AUTOANTIBODY RECEPTOR (CAAR) THAT BINDS AUTOANTIBODIES TARGETING THE CENTRAL NERVOUS SYSTEM IN NEUROLOGICAL AUTOIMMUNE DISEASE

The invention relates to the field of targeted cellular therapy employing a chimeric autoantibody receptor and the treatment of neurological autoimmune disease.

The invention relates to a chimeric autoantibody receptor (CAAR) that enables targeting of an immune cell to autoantibody producing B cells. The CAAR comprises an autoantigen or fragment thereof that is bound by autoantibodies associated with a neurological autoimmune disease primarily targeting the central nervous system. The invention relates to a nucleic acid molecule encoding a chimeric autoantibody receptor (CAAR), the nucleic acid molecule comprising a sequence encoding an autoantigen or fragment thereof that is bound by autoantibodies associated with a neurological autoimmune disease primarily targeting the central nervous system, a sequence encoding a transmembrane domain, and a sequence encoding an intracellular signaling domain.

In one embodiment, the autoantigen encoded by the nucleic acid sequence comprises or consists of an N-methyl-D-aspartate receptor (NMDAR), or one or more NMDAR fragments. The invention further relates to the chimeric autoantibody receptor (CAAR) protein of the invention, a vector comprising a nucleic acid molecule encoding a chimeric autoantibody receptor (CAAR) of the invention, a genetically modified immune cell comprising the nucleic acid molecule encoding the CAAR and the use of the immune cell in the treatment or prevention of a neurological autoimmune disease primarily targeting the central nervous system, such as an autoimmune encephalopathy or encephalomyelopathy, preferably anti-NMDAR encephalitis.

REFERENCE TO SEQUENCE LISTING

The present application is being filed along with a Sequence Listing in electronic format. The Sequence Listing is provided as a file entitled 54687469_1.TXT, created and last modified on Dec. 3, 2021, which is 61.7 Kb in size. The information in the electronic format of the Sequence Listing is incorporated herein by reference in its entirety.

BACKGROUND OF THE INVENTION

Autoimmunity, a main component in nervous system disease, is a misguided immune response to the body's own organs. Neurological autoimmune disease occurs when autoimmunity (autoantibodies) targets a structure within the central or peripheral nervous system. Anti-N-methyl-D-aspartate receptor encephalitis (anti-NMDAR encephalitis) has recently been discovered as an autoimmune neuropsychiatric disease in which autoantibodies against the NR1 subunit of the NMDA receptor are formed and bind to NMDA receptors (NMDAR) in the brain (Titulaer 2013). Binding of the autoantibodies to the NMDAR leads to an internalization of the receptors and thus to a dysfunction of affected nerve cells (Kreye 2016), commonly characterized by symptoms such as epileptic seizures, impaired consciousness, movement disorders, memory loss and signs of psychosis (Dalmau 2011, Prüss 2017).

The removal of the autoantibodies from the blood and cerebrospinal fluid of patients leads to a significant clinical improvement, such that many patients can lead an independent life after appropriate treatment removing said autoantibodies. However, significant problems are associated with established therapeutic approaches using unspecific immunosuppression, such as steroid treatment, plasmapheresis, cyclophosphamide or rituximab treatment (to deplete antibody-producing B-cells). These treatments have led to an improvement in the patient's condition but are associated with significant side effects (Titulaer 2013).

In the case of plasmapheresis, unwanted side effects typically arise as injuries caused by the central venous catheter, the development of circulatory disorders such as hypotensive and/or circulatory dysregulation, i.e. due to fluid shifting, coagulation disorders with thrombosis, and infections, including sepsis.

Drug-induced immunosuppression is especially susceptible to causing severe infections, in addition to the sometimes significant well-known side effects of pharmacological therapy. Furthermore, prophylaxis by vaccinations and the protection of the body by beneficial antibodies that challenge bacterial and viral infection can be negated by unspecific immunotherapies.

For example, the removal of autoantibodies in general does not lead per se to the removal of the autoantibody-producing cells, i.e. the source of the disease-causing agent. In the acute phase of anti-NMDAR encephalitis, substantial quantities of disease-causing autoantibodies are produced by the responsible B cells. This production is not inhibited by removal of the autoantibodies, as long as the responsible B cells remain active, thereby leading to the necessity of repeated autoantibody-removal procedures, such as apheresis and the like.

These problems can only be solved by selective approaches for removal of disease-specific autoantibodies and the cause of their production. Until the present time, to the best knowledge of the inventors, no effective therapeutic options are available for treating neurological autoimmune disease that work according to this principle, namely the specific removal of selected autoimmune antibody-producing cells.

Generally speaking, chimeric antigen receptor (CAR) expressing T cells (CAR-T cells) are human T cells that have been genetically engineered so that their activation depends on binding between a T cell-located antibody of the CAR and target peptides on the surface of a target cell. CAR-T cells are used mainly in cancer therapy, where they detect tumor-specific epitopes via an antigen portion of the CAR and selectively activate the T-cell-mediated cytotoxic activity to kill tumor cells. Adoptive chimeric antigen receptor (CAR)-T cell therapies targeted at CD19 antigen on leukemia and lymphoma B cells has brought about substantial clinical efficacy and currently, more than 40 CD19 CAR-T cell studies are registered at the FDA for the treatment of B-NHL and B-ALL.

The present invention however employs a chimeric autoantibody receptor (CAAR) expressed from engineered T cells (CAAR-T cells), wherein the CAAR comprises—as a targeting domain in place of an antibody fragment—an autoantigen that is bound by autoantibodies, which are evident in neurological autoimmune disease and presented by disease-causing B cells. The CAAR-autoantigen directs the engineered T cell to an autoantibody-producing B-cell, wherein the binding between autoantibody and CAAR-autoantigen leads to an activation of the engineered T-cell and the release of toxic mediators leading to lysis of the disease-specific B cell (FIG. 1A). Other B cells (e.g., those producing/presenting beneficial antibodies e.g. after vacci-
nation) remain spared from the T-cell mediated B-cell deple-
tion (FIG. 1B).

Ellebrecht et al. (2016, Science) and WO 2015/168613
describe a similar approach employing a CAAR-T construct
directed against autoantibodies that bind the skin cell adhe-
sion protein desmoglein 3 (Dsg3). A depletion of Dsg3
autoantibody-producing B cells was achieved.

Richman et al (NIH grant application 9600548) have also
proposed chimeric autoantibody receptor (CAAR)-express-
ing T cells (CAART) to attack autoantibody-producing B
cells in a rat model of muscle-specific kinase (MuSK)-MG
experimental autoimmune MuSK myasthenia (EAMM). For
the CAAR, the single chain anti-tumor Fv of a traditional
CAR was replaced by the autoantigen, the MuSK ectodo-
main, to target the anti-MuSK autoantibody displayed on the
surface of the autoimmune B cells.

Fransson et al (2012) disclose lentivirus vector modified
T cells which express a chimeric antigen receptor (CAR)
targeting myelin oligodendrocyte glycoprotein (MOG).
Ryan et al (2017) references Fransson and mentions the
Dsg3-CAAR disclosed in Ellebrecht (2016). Neither of
these references teaches a CAAR comprising—as a target-
ing domain—an autoantigen that is bound by autoantibodies
evident in neurological autoimmune disease.

WO2018127585 teaches chimeric autoantibody receptors
(CAARs) specific for autoantibody-producing B-cells. The
N-methyl-D-aspartate receptor is suggested as an example
of such an autoantigen. However, no experimental support is
presented for this embodiment and effector T cells are
excluded from use for such a construct. WO2018127584
teaches a monospecific population of Treg cells, wherein the
Treg cells comprise a chimeric receptor, wherein said chi-
meric receptor recognizes a B cell surface marker. No
mention is made of a CAAR comprising an autoantigen
bound by autoantibodies in neurological autoimmune dis-
ease.

Chatenoud (2016) and Tahir (2018) provide an overview
of CAAR technology and reference the CAAR of Ellebrecht
(2016). Ludwig (2017), WO2015177512, Kreye (2016) and
McKee (2017) provide background information on
NMDAR encephalitis and NMDAR autoantibodies. No
mention is made of a CAAR comprising an autoantigen
bound by autoantibodies in neurological autoimmune dis-
ease.

Thus, the current invention addresses the problems of
broad and unspecific immune-depletion and immunosup-
pression in treating neurological autoimmune disease.
Although a number of potential alternatives for treating
neurological autoimmune disease are established or in
development, a significant need remains for providing effec-
tive means for addressing such disease, in particular for
treating neurological autoimmune disease primarily target-
ing the central nervous system, that avoid widespread immu-
nosuppression.

SUMMARY OF THE INVENTION

In light of the prior art the technical problem underlying
the invention was the provision of alternative or improved
means for treating and/or preventing neurological autoim-
mune disease, such as neurological autoimmune disease
primarily targeting the central nervous system, preferably
anti-NMDAR encephalitis. A further objective of the inven-
tion was to provide such therapeutic options whilst avoiding
or minimizing widespread and unspecific immunosuppres-
sion.

This problem is solved by the features of the independent
claims. Preferred embodiments of the present invention are
provided by the dependent claims.

Therefore, the invention relates to a nucleic acid molecule
encoding a chimeric autoantibody receptor (CAAR), the
nucleic acid molecule comprising:
    i. a sequence encoding an autoantigen or fragment thereof
       that is bound by autoantibodies associated with a
       neurological autoimmune disease primarily targeting
       the central nervous system,
    ii. a sequence encoding a transmembrane domain, and
    iii. a sequence encoding an intracellular signaling domain.

To the knowledge of the inventors, the CAAR of the
present invention represents the first autoantibody-specific
cellular immunotherapy approach towards treating neuro-
logical autoimmune disease that primarily targets the central
nervous system. It was surprising that the autoantigen-
comprising constructs described herein would exhibit such
excellent autoantibody-specific B-cell depletion in the in
vitro and in vivo models applied in the examples below.

The present invention leads to a number of fundamental
improvements and advantages over treatments described in
the prior art, for example the CAAR as described herein, and
associated aspects of the inventions including corresponding
CAAR modified immune cells, enables a selective and
potentially curative approach towards treating the neurologi-
cal autoimmune diseases described herein. The autoantibody
specificity achieved by incorporating—as a targeting
domain for the CAAR-modified immune cells—an autoan-
tigen, which is bound by autoantibodies in neurological
autoimmune disease, leads to selective removal of the dis-
ease agent with little or no widespread immunosuppression.
Furthermore, the elimination of the autoantibody producing
B cells represents a potentially curative effect, such that the
underlying cause of the disease agent is removed, thereby
addressing the disease at the level of causality and leading
to enhanced chances of long term or permanent mitigation of
the disease. This combination of benefits represents an
unexpectedly effective approach with a low risk profile
regarding potential side effects due to widespread immuno-
suppression or disease recurrence.

The specific autoantigens employed in the constructs
described herein therefore represent a novel and inventive
group of autoantigens targeted by autoantibodies in neuro-
logical autoimmune disease primarily targeting the central
nervous system. The particular medical conditions to be
treated according to the present invention therefore also
represent a novel and inventive group of autoimmune dis-
eases in which autoantibodies target primarily the central
nervous system.

The present invention represents a surprising and benefi-
cial advancement over earlier descriptions of such CAAR
constructs in treating for example peripheral neurological
autoimmune diseases, such as myasthenia gravis. The effec-
tive depletion of autoantibodies primarily targeting autoan-
tigens of the central nervous system represents a significant
and surprising medical advance over earlier descriptions of
similar CAAR constructs.

A skilled person is capable of electing a suitable autoan-
tigen, known to be a target of autoantibodies that primarily
targets the central nervous system, for introduction into the
CAAR of the present invention. For example, the presence
of serum or cerebrospinal fluid (CSF) antibodies to any
given autoantigen indicates the suitableness of the autoan-
tigen in the present invention. Various subgroups of such
autoimmune disease are presented below and represent
preferred non-limiting embodiments of the invention.

In one embodiment, the autoantigen encoded by the nucleic acid sequence is bound by autoantibodies in an autoimmune encephalopathy or encephalomyelopathy.

In one embodiment, the autoantigen encoded by the nucleic acid sequence is bound by autoantibodies in anti-N-methyl-D-aspartate receptor encephalitis (anti-NMDAR encephalitis).

In one embodiment, the autoantigen encoded by the nucleic acid sequence comprises or consists of an N-methyl-D-aspartate receptor (NMDAR), or one or more NMDAR fragments.

Anti-N-methyl-D-aspartate (NMDA) receptor encephalitis was first described by Dalmau and colleagues (Dalmau et al 2008), who identified multiple patients presenting with prominent neuropsychiatric symptoms. All were confirmed to have serum or cerebrospinal fluid (CSF) antibodies to the NMDA receptor. Anti-NMDAR encephalitis is a severe disease, with patients typically showing psychiatric symptoms such as agitation, bizarre and disinhibited behavior, delusions, auditory and visual hallucinations, cognitive dysfunction, such as short-term memory loss, motor dysfunction, such as dyskinetic movements and orofacial dyskinesias, and epileptic seizures.

In one embodiment, the autoantigen encoded by the nucleic acid sequence comprises or consists of an NR1 subunit of an NMDA receptor, or one or more fragments thereof.

In one embodiment, the autoantigen encoded by the nucleic acid sequence comprises or consists of an NR2 subunit of an NMDA receptor, or one or more fragments thereof.

Studies have revealed that the extracellular N-terminal domain of the NR1 subunit is the main epitope of disease-causing autoantibodies in Anti-NMDAR encephalitis. Various portions of the NMDAR may therefore be employed, and the NR1 subunit, or one or more fragments thereof, are therefore preferred.

The nomenclature employed for defining the various domains of the NMDA receptor are not considered limiting to the present invention. Alternative nomenclatures for the domains are therefore incorporated accordingly. For example, the term "GluN1" has been used in relevant literature to represent the term "NR1", the term "GluN2" has been used in the literature to represent "NR2". Additionally, the term GRIN1 (Glutamate Inotropic Receptor NMDA Type Subunit 1) has been employed to describe the NR1 subunit, for example in the NCBI database under Gene ID: 2902. Alternative nomenclature may be employed, such as commonly used in the art, such as NR1, MRD8, GluN1, NMDA1, NDHMSD, NDHMSR, NMD-R1 and NMDAR1. This alternative NMDAR domain nomenclature, and the corresponding domains, are therefore encompassed by the invention.

Methodologies for determining autoantigens and relevant epitopes from the NMDAR are known to a skilled person, such as those employing cell-based assays, or immunohistochemistry of unfixed mouse brain sections, or similar methodologies used under various experimental conditions. Different subunits of the autoantigen (e.g. NR1 and/or NR2, or various fragments thereof) or different body fluids (serum, plasma, or CSF) may be employed, and different immunoglobulins may be detected (without limitation, IgG, IgA, and/or IgM).

In one embodiment, the autoantigen encoded by the nucleic acid sequence comprises or consists of an amino-terminal domain (ATD) of a NMDA receptor, or one or more fragments thereof.

In further embodiments, the one or more fragments of a NMDA receptor, or any given domain of a NMDA receptor, is a fragment bound by autoantibodies present in a relevant disease. A skilled person is capable of detecting autoantibodies in any of the relevant diseases described herein, and further determining the autoantigen bound by said antibody. The autoantigen may therefore be employed correspondingly in the CAAR of the invention.

In one embodiment, the autoantigen encoded by the nucleic acid sequence comprises or consists of an amino-terminal domain (ATD), an S1 domain and an S2 domain of a NMDA receptor, or one or more fragments thereof, and optionally linkers or spacers positioned between said domains or fragments thereof.

In one embodiment, the autoantigen encoded by the nucleic acid sequence comprises or consists of an amino-terminal domain (ATD), and an S1 domain and/or an S2 domain of a NMDA receptor, or one or more fragments thereof, and optionally linkers or spacers positioned between said domains or fragments thereof.

As is shown in the examples below, the combined use of the amino-terminal domain with an S1 domain and an S2 domain of the NMDAR leads to effective autoantibody binding and subsequent depletion of the cells producing pathogenic autoantibodies.

In one embodiment, the autoantigen encoded by the nucleic acid sequence comprises or consists of a protein selected from the group consisting of leucine-rich glioma-inactivated 1 (LGI1), α-amino-3-hydroxy-5-methyl-4-isoxazolepropionic acid receptor (AMPAR), Ig-Like Domain-Containing Protein 5 (IgLON5), Metabotropic glutamate receptor 5 (mGluR5), glutamic acid decarboxylase (GAD), contactin-associated protein-like 2 (CASPR2), a gamma-aminobutyric acid (GABA) receptor, such as GABA-A and/or GABA-B, myelin oligodendrocyte glycoprotein (MOG) and aquaporin-4 (AQP4), or one or more fragments thereof.

The additional autoantigens presented above are known to be targets of pathogenic autoantibodies in neurological autoimmune disease targeting primarily the central nervous system. A skilled person is capable of determining whether an antigen is suitable in the approach described herein. Routine methods using for example ELISA techniques can be applied with any given immobilized candidate autoantigen, which are subsequently incubated with patient samples, such as urine, blood, serum or CSF, and subsequent detection of antibodies bound to the immobilized antigen is carried out, in order to determine whether any given autoantigen represents a suitable targeting domain in order to direct the activity of a CAAR-engineered immune cell to deplete the specific pathogenic B cell of interest.

Furthermore, the CAAR constructs of the present invention exhibit unexpected and advantageous properties. For example, T-cells transduced with the inventive CAAR show only a minor reduction of killing efficiency when soluble NR1-reactive antibodies are present in cell culture medium. This data, which is described in more detail below, demonstrates that the inventive CAAR-expressing cells maintain their function in a situation similar to that found in patients, i.e. when soluble NR1-reactive antibodies are present and potentially in competition as a binding target of the inventive CAAR-expressing cells. This property could not have been expected or derived from the prior art and indicates the excellent activity induced by the inventive CAAR. These advantages are particularly relevant for both ATD-CAAR and ATD-S1-S2-T cells.

In one embodiment of the invention, the CAAR-expressing cell, such as a T cell, maintains cytotoxic activity against target cells presenting unwanted autoantibodies in the presence of soluble reactive antibodies. In a preferred embodiment, the CAAR comprises an autoantigen that comprises or consists of an amino-terminal domain (ATD), an S1 domain and an S2 domain of a NMDA receptor, or one or more fragments thereof, and optionally linkers or spacers positioned between said domains or fragments thereof.

A further example of a beneficial property of the CAAR of the present invention is that cells expressing the inventive CAAR, such as CAAR-T cells, can be temporarily halted using Dasatinib, a clinically approved Tyrosine Kinase inhibitor. This property therefore enables a "safety strategy", by which the CAAR-expressing cells, such as T cells, can temporarily be inactivated using the drug Dasatinib to help reduce acute toxicity. Should the cytotoxicity of the administered CAAR-expressing cells lead to some unwanted effect, Dasatinib can be administered to temporarily deactivate their activity. CAAR-expressing cells can recover their cytotoxic effects (against cells presenting unwanted autoantibodies) after the drug is withdrawn. The combined administration of Dasatinib is therefore an option to regulate the cytotoxicity of the CAAR-expressing cells, useful in titrating side effects or as a safety switch, post-administration. This property could not have been expected or derived from the prior art and indicates the excellent activity induced by the inventive CAAR. These advantages are particularly relevant for both ATD-CAAR and ATD-S1-S2-T cells.

In one embodiment of the invention, the CAAR-expressing cell, such as a T cell, can be temporarily inhibited by treatment with a suitable agent, preferably with Dasatinib. In a preferred embodiment, the CAAR comprises an autoantigen that comprises or consists of an amino-terminal domain (ATD), an S1 domain and an S2 domain of a NMDA receptor, or one or more fragments thereof, and optionally linkers or spacers positioned between said domains or fragments thereof.

In some embodiments, the CAAR constructs encode (and the CAAR polypeptides comprise accordingly) additionally a marker, such as a transduction marker (preferably a truncated epidermal growth factor receptor; EGFRt), so that a larger number of CAAR-positive T cells can be enriched. As a further advantage, constructs with additional transduction markers may enable, in an in vivo setting, controlled ending of the therapy through treatment with a therapeutic antibody such as cetuximab, as rescue medication. These constructs therefore comprise transgene-encoded cell surface polypeptides for selection, in vivo tracking and/or ablation of engineered cells.

In further embodiments, the nucleic acid molecule encoding a CAAR as described herein is characterized by one or more of the following features:

the transmembrane domain is a CD28, ICOS or CD8 alpha transmembrane domain;

the intracellular domain comprises a CD28, ICOS or CD137 (4-1BB) co-stimulatory domain, or any combination thereof;

the intracellular domain comprises a CD3 zeta chain signaling domain; and/or the nucleic acid molecule comprises additionally one or more sequences encoding one or more leader, linker and/or spacer polypeptides positioned between the autoantigen and transmembrane domain and/or N-terminally of and/or between fragments of the autoantigen, and/or between the transmembrane and intracellular co-stimulatory domain.

As is demonstrated in the examples below, the above transmembrane, costimulatory and signaling domains, optionally in combination with the linkers described herein, lead to effective autoantibody specific B cell depletion. These preferred embodiments are nonlimiting and a skilled person is capable of employing alternative CAR constructs in place of those preferred embodiments mentioned herein.

In further embodiments, the CAAR of the present invention is characterized in that the co-stimulatory domain (transmembrane and intracellular signaling domain) comprises a signaling domain from any one or more of CD28, CD137 (4-1BB), ICOS, CD134 OX40), DapIO, CD27, CD2, CD5, ICAM-1, LFA-1, Lck, TNFR-J, TNFR-II, Fas, CD30, CD40 and combinations thereof.

In further embodiments, the CAAR of the present invention is characterized in that the transmembrane domain is selected from an artificial hydrophobic sequence and transmembrane domains of a Type I transmembrane protein, an alpha, beta or zeta chain of a T cell receptor, CD28, ICOS, CD3 epsilon, CD45, CD4, CD5, CD8, CD9, CD16, CD22, CD33, CD37, CD64, CD80, CD86, CD134, CD137, and CD154.

In further embodiments, the CAAR of the present invention is characterized in that the intracellular signaling domain comprises a signaling domain of one or more of a human CD3 zeta chain, FcyRIII, FccRI, a cytoplasmic tail of a Fc receptor, an immunoreceptor tyrosine-based activation motif (ITAM) bearing cytoplasmic receptors, TCR zeta, FcR gamma, FcR beta, CD3 gamma, CD3 delta, CD3 epsilon, CD5, CD22, CD79a, CD79b, and CD66d, and combinations thereof.

The embodiments described below represent preferred but non-limiting embodiments of the CAAR constructs developed by the inventors. Variation in the particular domains described below is contemplated and encompassed within the scope of the invention.

In further embodiments, the nucleic acid molecule encoding a chimeric autoantibody receptor (CAAR) as described herein, comprises:

i. a sequence encoding a leader polypeptide, wherein the leader polypeptide is preferably a CD8 leader or a NR1 leader polypeptide, said sequence preferably comprising a sequence according to SEQ ID NO 1 or SEQ ID NO 2, respectively;

ii. a sequence encoding an autoantigen, wherein the autoantigen is preferably a N-methyl-D-aspartate receptor (NMDAR) or one or more NMDAR fragments, said sequence preferably comprising a sequence according to SEQ ID NO 3 (ATD) and/or SEQ ID NO 4 (S1) and/or SEQ ID NO 5 (S2) and/or SEQ ID NO 6 (NR1) or any sub-sequence of SEQ ID NO 6 encoding an autoantigenic fragment of a NMDAR NR1 protein (i.e. fragment bound by pathogenic autoantibodies);

iii. optionally a sequence encoding a linker polypeptide positioned between one or more NMDAR fragments, said sequence preferably comprising a sequence according to GGCACC (linker-1);

iv. optionally a sequence encoding a linker polypeptide positioned between the autoantigen and transmembrane domain, said sequence preferably comprising a sequence according to SEQ ID NO 7 (linker-2) or SEQ ID NO 32 (linker-2b);

v. a sequence encoding a transmembrane domain, preferably a CD8 alpha transmembrane domain or an ICOS transmembrane domain, said sequence preferably comprising a sequence according to SEQ ID NO 8 (CD8α) or SEQ ID NO 9 (ICOS);

vi. optionally a sequence encoding a linker polypeptide positioned between a transmembrane domain and an intracellular signaling domain, said sequence preferably comprising a sequence according to GGCAGC (linker-3); and/or vii. a sequence encoding an intracellular signaling domain, said intracellular signaling domain preferably comprising a CD137 (4-1BB) co-stimulatory domain and a CD3 zeta chain signaling domain, said sequence preferably comprising a sequence according to SEQ ID NO 10 (CD137) and SEQ ID NO 11 (CD3z), respectively, wherein optionally a linker sequence is positioned between the co-stimulatory and signaling domains.

In some embodiments, the nucleic acid molecule encoding a chimeric autoantibody receptor (CAAR) as described herein comprises a sequence according to SEQ ID NO 24 (ATD-S1-S2) or SEQ ID NO 25 (ATD-S1) or SEQ ID NO 26 (ATD) or SEQ ID NO 27 (ATD-ICOS).

In a preferred embodiment, the invention relates to an isolated nucleic acid molecule, optionally in the form of an isolated vector, such as an isolated viral vector or transposon, selected from the group consisting of:

a) a nucleic acid molecule comprising a nucleotide sequence
   which encodes a CAAR polypeptide as described herein,
   which encodes a targeting (i.e. an extracellular antigen-binding (auto-antibody-binding) domain or part thereof, the sequence comprising one or more of SEQ ID NOs 3, 4, 5, and/or 6, and/or
   which encodes a CAAR polypeptide as described herein, the sequence comprising one or more of SEQ ID NOs 24, 25, 26, and/or 27;

b) a nucleic acid molecule which is complementary to a nucleotide sequence in accordance with a);

c) a nucleic acid molecule comprising a nucleotide sequence having sufficient sequence identity to be functionally analogous/equivalent to a nucleotide sequence according to a) or b), comprising preferably a sequence identity to a nucleotide sequence according to a) or b) of at least 50%, preferably 60%, 70%, 80%, 85%, 90%, or 95%;

d) a nucleic acid molecule which, as a consequence of the genetic code, is degenerated into a nucleotide sequence according to a) through c); and/or e) a nucleic acid molecule according to a nucleotide sequence of a) through d) which is modified by deletions, additions, substitutions, translocations, inversions and/or insertions and is functionally analogous/equivalent to a nucleotide sequence according to a) through d).

Variation in length of the nucleotide sequences as described herein is also encompassed by the present invention. A skilled person is capable of providing nucleic acid sequence variants that are longer or shorter than SEQ ID NO 3-6, which will still exhibit sufficient similarity to code for the proteins described herein in order to provide the outcomes desired.

For example, shorter variants of SEQ ID NO 3-6 comprising 10, 20, 30, 40, or up to 50 nucleic acids less than the disclosed form may also enable effective coding of an autoantigen, as described herein. Fragments of SEQ ID NO 3-6 are therefore also considered. Additionally, longer variants of SEQ ID NO 3-6 comprising 10, 20, 30, 40, or up to 50 nucleic acids of any given additional sequence more than SEQ ID NO 3-6 may also enable effective outcomes, as described herein.

In a further aspect, the invention relates to a vector comprising a nucleic acid molecule encoding a chimeric autoantibody receptor (CAAR) as described herein.

In some embodiments, the vector is a viral vector, such as a lentiviral vector or retroviral vector.

In some embodiments, the vector is a nanoparticle as a transfection vehicle.

In some embodiments, the vector is a transposon or an RNA vector.

In some embodiments, the vector is a sleeping beauty transposon, preferably a SB100/pT4 sleeping beauty transposon.

In some embodiments, the vector is suitable for integration of the CAAR encoding sequence into a cell via CRISPR/Cas9-mediated gene modification.

In order to express a desired polypeptide, a nucleotide sequence encoding the CAAR polypeptide, can be inserted into appropriate vector. Examples of vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or PI-derived artificial chromosome (PAC), bacteriophages such as lambda phage or MI 3 phage, and animal viruses. CAAR-encoding nucleotide sequences may also be present in the form suitable for integration into a cell via CRISPR/Cas9-mediated gene modification.

In a further aspect, the invention relates to a chimeric autoantibody receptor (CAAR) polypeptide, preferably encoded by a nucleic acid molecule according to any one of the preceding claims, wherein the CAAR comprises:

an autoantigen that is bound by autoantibodies associated with a neurological autoimmune disease primarily targeting the central nervous system, preferably an autoantigen as described in detail above, such as an N-methyl-D-aspartate receptor (NMDAR), or one or more NMDAR fragments, leucine-rich glioma-inactivated 1 (LGI1), α-amino-3-hydroxy-5-methyl-4-isoxazolepropionic acid receptor (AMPAR), Ig-Like Domain-Containing Protein 5 (IgLON5), Metabotropic glutamate receptor 5 (mGluR5), glutamic acid decarboxylase (GAD), contactin-associated protein-like 2 (CASPR2), a gamma-aminobutyric acid (GABA) receptor, such as GABA-A and/or GABA-B, myelin oligodendrocyte glycoprotein (MOG) and aquaporin-4 (AQP4), or one or more fragments thereof,
a transmembrane domain, and
an intracellular signaling domain.

In some embodiments, the chimeric autoantibody receptor (CAAR) polypeptide comprises:

i. a leader polypeptide, wherein the leader polypeptide is preferably a CD8 leader or a NR1 leader polypeptide, according to SEQ ID NO 12 or SEQ ID NO 13, respectively;

ii. an autoantigen, wherein the autoantigen is preferably a N-methyl-D-aspartate receptor (NMDAR) or one or more NMDAR fragments, said autoantigen preferably comprising a sequence according to SEQ ID NO 14 (ATD) and/or SEQ ID NO 15 (S1) and/or SEQ ID NO 16 (S2) and/or SEQ ID NO 17 (NR1) or any subsequence of SEQ ID NO 17 that is an autoantigenic fragment of a NMDAR NR1 protein (i.e. fragment bound by pathogenic autoantibodies);

iii. optionally a linker polypeptide positioned between one or more NMDAR fragments, said linker preferably comprising a sequence according to GT (linker-1);

iv. optionally a linker polypeptide positioned between the autoantigen and transmembrane domain, said linker preferably comprising a sequence according to SEQ ID NO 18 or 19 (linker-2 or 2b);

v. a transmembrane domain, preferably a CD8 alpha transmembrane domain or an ICOS transmembrane domain, said domain preferably comprising a sequence according to SEQ ID NO 20 (CD8α) or SEQ ID NO 21 (ICOS);

vi. optionally a linker polypeptide positioned between a transmembrane domain and an intracellular signaling domain, said linker preferably comprising a sequence according to GS (linker-3); and/or vii. an intracellular signaling domain, said intracellular signaling domain preferably comprising a CD137 (4-1BB) co-stimulatory domain and a CD3 zeta chain signaling domain, said domain comprising preferably a sequence according to SEQ ID NO 22 (CD137) and SEQ ID NO 23 (CD3z), respectively, wherein optionally a linker sequence is positioned between the co-stimulatory and signaling domains.

In some embodiments, the chimeric autoantibody receptor (CAAR) as described herein comprises a sequence according to SEQ ID NO 28 (ATD-S1-S2) or SEQ ID NO 29 (ATD-S1) or SEQ ID NO 30 (ATD) or SEQ ID NO 31 (ATD-ICOS).

Variation in length of the amino acid sequences as described herein is also encompassed by the present invention. A skilled person is capable of providing amino acid sequence variants that are longer or shorter than SEQ ID NO 14-17, which will still exhibit sufficient similarity to the specific proteins described herein in order to provide the outcomes desired. For example, shorter variants of SEQ ID NO 14-17 comprising 10, 20, 30, 40, or up to 50 amino acids less than the full-length form may also enable effective binding, as described herein. Fragments of SEQ ID NO 14-17 are therefore also considered. Additionally, longer variants of SEQ ID NO 14-17 comprising 10, 20, 30, 40, or up to 50 amino acids of any given additional sequence may also enable effective outcomes, as described herein.

In other embodiments of the invention, the autoantigen protein employed may comprise or consist of an amino acid sequence with at least 50%, 60%, 70%, 80%, 90% or 95% sequence identity to SEQ ID NO 14-17. Preferably the sequence variant comprises at least 80%, 90%, 91, 92, 93, 94, 95, 96, 97, 98 or 99% sequence identity to SEQ ID NO 14-17 and preferably exhibits functional analogy to the specific human proteins described herein. Functional analogy is assessed via determining the same or a similar autoantigen-binding and/or autoantibody-specific B cell depletion as described herein. Suitable in vitro assays for determining the desired binding are known to a skilled person.

The amino acid sequences may also comprise 0 to 100, 2 to 50, 5 to 20, or for example 8 to 15, or any value from 0 to 20, amino acid additions or deletions at either the N- and/or C-terminus of the proteins of SEQ ID NO 14-17. The termini may also be modified with additional linker sequences, or removal of sequences, as long as the properties of the protein with respect to autoantibody binding are essentially maintained.

An additional and surprising aspect of the invention is an improved stability of the CAAR as disclosed herein. The CAAR polypeptide can readily be stored for extended periods under appropriate conditions without any loss of binding affinity.

Preferred amino acid and nucleotide sequences of the present invention:

| SEQ ID NO | Sequence | Description |
|---|---|---|
| 1 | ATGGCTCTGCCTGTGACAGCTCTGCTGCTGCCTCTGGCCCTGC TGCTGCATGCTGCCAGACCT | CD8 leader nt |
| 2 | ATGTCTACAATGAGACTGCTGACACTGGCCCTGCTGTTCAGCTG TTCTGTGGCC | NR1 leader nt |
| 3 | AGAGCCGCCTGCGATCCCAAGATCGTGAATATCGGAGCCGTGC TGAGCACCCGGAAGCACGAGCAGATGTTCAGAGAAGCCGTGAA CCAGGCCAACAAGAGACACGGCAGCTGGAAGATCCAGCTGAAC GCCACAAGCGTGACCCACAAGCCTAACGCCATTCAGATGGCCC TGAGCGTGTGCGAGGATCTGATCAGCTCTCAGGTGTACGCCAT CCTGGTGTCTCACCCTCCAACACCTAACGACCACTTCACCCCTA CACCTGTGTCTTACACCGCCGGCTTCTACAGAATCCCTGTGCTG GGCCTGACCACCAGAATGAGCATCTACAGCGACAAGAGCATCC ACCTGAGCTTTCTGCGGACCGTGCCTCCTTACAGCCACCAGTCT AGCGTTTGGTTCGAGATGATGCGGGTGTACAGCTGGAACCACA TCATCCTGCTGGTGTCCGACGACCACGAAGGCAGAGCCGCTCA GAAGAGACTGGAAACCCTGCTGGAAGAGAGAGAGTCCAAGGCC GAGAAGGTGCTGCAGTTCGATCCCGGCACCAAGAACGTGACAG CCCTGCTGATGGAAGCCAAAGAACTGGAAGCCAGAGTGATCAT CCTGAGCGCCTCCGAAGATGATGCCGCCACCGTGTATAGAGCC GCCGCTATGCTGAATATGACCGGCAGCGGATACGTGTGGCTCG TGGGCGAGAGAGAGATTAGCGGAAACGCCCTGAGATACGCCCC TGATGGAATCCTGGGACTGCAGCTGATCAACGGCAAGAACGAG AGCGCCCACATCTCTGATGCCGTGGGGAGTTGTGGCTCAGGCCG TGCATGAGCTGCTGGAAAAAGAGAACATCACCGATCCTCCACG GGGCTGCGTGGGCAACACCAACATCTGGAAAACAGGCCCACTG TTCAAGCGGGTGCTGATGAGCAGCAAATACGCCGATGGCGTGA CAGGCCGGGTCGAGTTTAATGAGGACGGCGACAGAAAGTTCGC CAACTACAGCATCATGAACCTGCAGAACCGGAAGCTGGTGCAA | NMDAR ATD nt |

-continued

| SEQ ID NO | Sequence | Description |
|---|---|---|
| | GTGGGCATCTACAACGGCACCCACGTGATCCCCAACGACCGGA AGATTATCTGGCCTGGCGGCGAAACCGAGAAGCCCAGAGGCTA CCAG | |
| 4 | ATGAGCACCAGACTGAAGATTGTGACCATCCACCAAGAGCCTTT CGTGTACGTGAAGCCCACACTGAGCGACGGCACCTGTAAAGAA GAGTTCACCGTCAACGGCGACCCTGTGAAGAAAGTGATCTGCA CAGGCCCCAACGATACAAGCCCTGGCAGCCCTAGACACACCGT TCCTCAGTGCTGCTACGGCTTCTGCATCGACCTGCTGATCAAGC TGGCCCGGACCATGAACTTCACCTACGAAGTGCACCTGGTGGC CGACGGCAAGTTTGGCACACAAGAGAGAGTGAACAACAGCAAC AAGAAAGAATGGAACGGCATGATGGGCGAGCTGCTGTCTGGAC AGGCCGACATGATTGTGGCCCCTCTGACCATCAACAACGAGCG GGCCCAGTACATCGAGTTCAGCAAGCCATTCAAGTACCAGGGC CTGACAATCCTGGTCAAGAAA | NMDAR S1 nt |
| — | GGCACC | Linker-1 nt |
| 5 | CGGATCACCGGCATCAACGACCCCAGACTGAGAAATCCCTCCG ACAAGTTCATCTACGCCACAGTGAAGCAGAGCAGCGTGGACAT CTACTTCAGACGCCAGGTGGAACTGAGCACCATGTACAGACACA TGGAAAAGCACAACTACGAGTCTGCCGCCGAGGCAATCCAGGC CGTCAGAGATAACAAGCTGCACGCCTTCATCTGGGACAGCGCC GTGCTGGAATTTGAGGCCAGCCAGAAGTGCGATCTGGTCACCA CCGGTGAACTGTTTTTCAGAAGCGGCTTTGGCATCGGCATGCG GAAGGACTCTCCCTGGAAGCAGAATGTGTCCCTGAGCATCCTG AAGTCTCACGAGAACGGCTTCATGGAAGATCTGGACAAGACCTG GGTCCGATACCAAGAGTGCGATAGC | NMDAR S2 nt |
| 6 | GCCCGCGGCCCGAGCCCATGAGCACCATGCGCCTGCTGACGC TCGCCCTGCTGTTCTCCTGCTCCGTCGCCCGTGCCGCGTGCGA CCCCAAGATCGTCAACATTGGCGCGGTGCTGAGCACGCGGAAG CACGAGCAGATGTTCCGCGAGGCCGTGAACCAGGCCAACAAGC GGCACGGCTCCTGGAAGATTCAGCTCAATGCCACCTCCGTCAC GCACAAGCCCAACGCCATCCAGATGGCTCTGTCGGTGTGCGAG GACCTCATCTCCAGCCAGGTCTACGCCATCCTAGTTAGCCATCC ACCTACCCCAACGACCACTTCACTCCCACCCCTGTCTCCTACA CAGCCGGCTTCTACCGCATACCCGTGCTGGGGCTGACCACCCG CATGTCCATCTACTCGGACAAGAGCATCCACCTGAGCTTCCTGC GCACCGTGCCGCCCTACTCCCACCAGTCCAGCGTGTGGTTTGA GATGATGCGTGTCTACAGCTGGAACCACATCATCCTGCTGGTCA GCGACGACCACGAGGGCCGGGCGGCTCAGAAACGCCTGGAGA CGCTGCTGGAGGAGCGTGAGTCCAAGGCAGAGAAGGTGCTGC AGTTTGACCCCAGGGACCAAGAACGTGACGGCCCTGCTGATGGA GGCGAAAGAGCTGGAGGCCCGGGTCATCATCCTTTCTGCCAGC GAGGACGATGCTGCCACTGTATACCGCGCAGCCGCGATGCTGA ACATGACGGGCTCCGGGTACGTGTGGCTGGTCGGCGAGCGCG AGATCTCGGGGAACGCCCTGCGCTACGCCCCGGACGGCATCCT CGGGCTGCAGCTCATCAACGGCAAGAACGAGTCGGCCCACATC AGCGACGCCGTAGGCGTGGTGGCCCAGGCCGTGCACGAGCTC CTCGAGAAGGAGAACATCACCGACCCGCCGCGGGGCTGCGTG GGCAACACCAACATCTGGAAGACCGGGCCGCTCTTCAAGAGAG TGCTGATGTCTTCCAAGTATGCGGATGGGGTGACTGGTCGCGT GGAGTTCAATGAGGATGGGGACCGGAAGTTCGCCAACTACAGC ATCATGAACCTGCAGAACCGCAAGCTGGTGCAAGTGGGCATCT ACAATGGCACCCACGTCATCCCTAATGACAGGAAGATCATCTGG CCAGGCGGAGAGACAGAGAAGCCTCGAGGGTACCAGATGTCCA CCAGACTGAAGATTGTGACGATCCACCAGGAGCCCTTCGTGTAC GTCAAGCCCACGCTGAGTGATGGGACATGCAAGGAGGAGTTCA CAGTCAACGGCGACCCAGTCAAGAAGGTGATCTGCACCGGGCC CAACGACACGTCGCCGGGCAGCCCCCGCCACACGGTGCCTCA GTGTTGCTACGCTTTTGCATCGACCTGCTCATCAAGCTGGCAC GGACCATGAACTTCACCTACGAGGTGCACCTGGTGGCAGATGG CAAGTTCGGCACACAGGAGCGGGTGAACAACAGCAACAAGAGA GAGTGGAATGGGATGATGGGCGAGCTGCTCAGCGGGCAGGCA GACATGATCGTGGCGCCGCTAACCATAAACAACGAGCGCGCGC AGTACATCGAGTTTTCCAAGCCCTTCAAGTACCAGGGCCTGACT ATTCTGGTCAAGAAGGAGATTCCCCGGAGCACGCTGGACTCGT TCATGCAGCCGTTCCAGAGCACACTGTGGCTGCTGGTGGGGCT GTCGGTGCACGTGGTGGCCGTGATGCTGTACCTGCTGGACCGC TTCAGCCCCTTCGGCCGGTTCAAGGTGAACAGCGAGGAGGAGG AGGAGGACGCACTGACCCTGTCCTCGGCCATGTGGTTCTCCTG GGGCGTCCTGCTCAACTCCGGCATCGGGGAAGGCGCCCCCAG AAGCTTCTCAGCGCGCATCCTGGGCATGGTGTGGGCCGGCTTT GCCATGATCATCGTGGCCTCCTACACCGCCAACCTGGCGGCCT | NMDAR complete NR1 nt (GenBank L05666.1) |

-continued

| SEQ ID NO | Sequence | Description |
|---|---|---|
| | TCCTGGTGCTGGACCGGCCGGAGGAGCGCATCACGGGCATCA ACGACCCTCGGCTGAGGAACCCCTCGGACAAGTTTATCTACGC CACGGTGAAGCAGAGCTCCGTGGATATCTACTTCCGGCGCCAG GTGGAGCTGAGCACCATGTACCGGCATATGGAGAAGCACAACT ACGAGAGTGCGGCGGAGGCCATCCAGGCCGTGAGAGACAACA AGCTGCATGCCTTCATCTGGGACTCGGCGGTGCTGGAGTTCGA GGCCTCGCAGAAGTGCGACCTGGTGACGACTGGAGAGCTGTTT TTCCGCTCGGGCTTCGGCATAGGCATGCGCAAAGACAGCCCT GGAAGCAGAACGTCTCCCTGTCCATCCTCAAGTCCCACGAGAAT GGCTTCATGGAAGACCTGGACAAGACGTGGGTTCGGTATCAGG AATGTGACTCGCGCAGCAACGCCCCTGCGACCCTTACTTTTGAG AACATGGCCGGGGTCTTCATGCTGGTAGCTGGGGGCATCGTGG CCGGGATCTTCCTGATTTTCATCGAGATTGCCTACAAGCGGCAC AAGGATGCTCGCCGGAAGCAGATGCAGCTGGCCTTTGCCGCCG TTAACGTGTGGCGGAAGAACCTGCAGCAGTACCATCCCACTGAT ATCACGGGCCCGCTCAACCTCTCAGATCCCTCGGTCAGCACCG TGGTGTGAGGCCCCCGGAGGCGCCCACCTGCCCAGTTAGCCC GGCCAAGGACACTGATGGGTCCTGCTGCTCGGGAAGGCCTGAG GGAAGCCCACCCGCCCCAGAGACTGCCCACCCTGGGCCTCCC GTCCGTCCGCCCGCCCACCCCGCTGCCTGGCGGGCAGCCCCT GCTGGACCAAGGTGCGGACCGGAGCGGCTGAGGACGGGGCAG AGCTGAGTCGGCTGGGCAGGGCCGCAGGGCGCTCCGGCAGAG GCAGGGCCCTGGGGTCTCTGAGCAGTGGGGAGCGGGGGCTAA CTGGCCCCAGGCGGAGGGGCTTGGAGCAGAGACGGCAGCCCC ATCCTTCCCGCAGCACCAGCCTGAGCCACAGTGGGGCCCATGG CCCCAGCTGGCTGGGTCGCCCCTCCTCGGGCGCCTGCGCTCC TCTGCAGCCTGAGCTCCACCCTCCCCTCTTCTTGCGGCACCGC CCACCCACACCCCGTCTGCCCCTTGACCCCACACGCCGGGGCT GGCCCTGCCCTCCCCCACGGCCGTCCCTGACTTCCCAGCTGCA GCGCCTCCCGCCGCCTCGGGCCGCCTC | |
| 7 | GCGTCGACCGGCGGAGGATCTGGCGGAGGCGGATCTTCTGGC | Linker-2 nt |
| 32 | GCTAGCGGCGGAGGCGGATCTGGTGGCGGAGGATCTTCTGGA | Linker-2b nt |
| 8 | ATCTATATCTGGGCTCCTCTGGCCGGCACATGCGGAGTTCTGCT GCTGAGCCTGGTCATCACCCTGTACTGC | CD8α transmembrane domain nt |
| 9 | TTCTGGCTGCCTATTGGCTGCGCCGCCTTTGTGGTCGTGTGTAT CCTGGGCTGCATCCTGATCTGCTGGCTGACCAAGAAAAAGTACA GCAGCAGCGTGCACGACCCCAACGGCGAGTACATGTTCATGAG AGCCGTGAACACCGCCAAGAAGTCCAGACTGACCGACGTGACA CTG | ICOS transmembrane and intracellular domain |
| — | GGCAGC | Linker-3 nt |
| 10 | AAGCGGGGCAGAAAGAAGCTGCTGTACATCTTCAAGCAGCCCT TCATGCGGCCCGTGCAGACAACCCAAGAGGAAGATGGCTGCTC CTGCAGATTCCCTGAGGAAGAGGAAGGCGGCTGCGAGCTG | CD137 (4-1BB) co-stimulatory domain nt |
| 11 | AGAGTGAAGTTCTCCAGATCCGCCGACGCTCCTGCTTACCAGCA GGGACAGAACCAGCTGTATAACGAGCTGAACCTGGGGCGCAGA GAAGAGTACGACGTGCTGGACAAGCGGAGAGGCAGAGATCCTG AGATGGGCGGCAAGCCCAGACGGAAGAATCCTCAAGAGGGCCT GTACAACGAACTCCAGAAAGACAAGATGGCCGAGGCCTACAGC GAGATCGGAATGAAGGGCGAGCGCAGAAGAGGCAAGGGACAC GATGGACTGTATCAGGGCCTGTCTACCGCCACCAAGGACACCT ATGATGCCCTGCACATGCAGGCCCTGCCACCTAGATAA | CD3 zeta chain signaling domain (activation domain) nt |
| 12 | MALPVTALLLPLALLLHAARP | CD8 leader p |
| 13 | MSTMRLLTLALLFSCSVA | NR1 leader p |
| 14 | RAACDPKIVNIGAVLSTRKHEQMFREAVNQANKRHGSWKIQLNATS VTHKPNAIQMALSVCEDLISSQVYAILVSHPPTPNDHFTPTPVSYTA GFYRIPVLGLTTRMSIYSDKSIHLSFLRTVPPYSHQSSVWFEMMRV YSWNHIILLVSDDHEGRAAQKRLETLLEERESKAEKVLQFDPGTKN VTALLMEAKELEARVIILSASEDDAATVYRAAAMLNMTGSGYVWLV GEREISGNALRYAPDGILGLQLINGKNESAHISDAVGVVAQAVHELL EKENITDPPRGCVGNTNIWKTGPLFKRVLMSSKYADGVTGRVEFN EDGDRKFANYSIMNLQNRKLVQVGIYNGTHVIPNDRKIIWPGGETE KPRGYQ | NMDAR ATD p |

-continued

| SEQ ID NO | Sequence | Description |
|---|---|---|
| 15 | MSTRLKIVTIHQEPFVYVKPTLSDGTCKEEFTVNGDPVKKVICTGPN DTSPGSPRHTVPQCCYGFCIDLLIKLARTMNFTYEVHLVADGKFGT QERVNNSNKKEWNGMMGELLSGQADMIVAPLTINNERAQYIEFSK PFKYQGLTILVKK | NMDAR S1 p |
| — | GT | Linker-1 p |
| 16 | RITGINDPRLRNPSDKFIYATVKQSSVDIYFRRQVELSTMYRHMEKH NYESAAEAIQAVRDNKLHAFIWDSAVLEFEASQKCDLVTTGELFFR SGFGIGMRKDSPWKQNVSLSILKSHENGFMEDLDKTWVRYQECD S | NMDAR S2 p |
| 17 | MSTMRLLTLALLFSCSVARAACDPKIVNIGAVLSTRKHEQMFREAV NQANKRHGSWKIQLNATSVTHKPNAIQMALSVCEDLISSQVYAILVS HPPTPNDHFTPTPVSYTAGFYRIPVLGLTTRMSIYSDKSIHLSFLRTV PPYSHQSSVWFEMMRVYSWNHIILLVSDDHEGRAAQKRLETLLEE RESKAEKVLQFDPGTKNVTALLMEAKELEARVIILSASEDDAATVYR AAAMLNMTGSGYVWLVGEREISGNALRYAPDGILGLQLINGKNESA HISDAVGVVAQAVHELLEKENITDPPRGCVGNTNIWKTGPLFKRVL MSSKYADGVTGRVEFNEDGDRKFANYSIMNLQNRKLVQVGIYNGT HVIPNDRKIIWPGGETEKPRGYQMSTRLKIVTIHQEPFVYVKPTLSD GTCKEEFTVNGDPVKKVICTGPNDTSPGSPRHTVPQCCYGFCIDLL IKLARTMNFTYEVHLVADGKFGTQERVNNSNKKEWNGMMGELLS GQADMIVAPLTINNERAQYIEFSKPFKYQGLTILVKKEIPRSTLDSFM QPFQSTLWLLVGLSVHVVAVMLYLLDRFSPFGRFKVNSEEEEEDAL TLSSAMWFSWGVLLNSGIGEGAPRSFSARILGMVWAGFAMIIVASY TANLAAFLVLDRPEERITGINDPRLRNPSDKFIYATVKQSSVDIYFRR QVELSTMYRHMEKHNYESAAEAIQAVRDNKLHAFIWDSAVLEFEAS QKCDLVTTGELFFRSGFGIGMRKDSPWKQNVSLSILKSHENGFME DLDKTWVRYQECDSRSNAPATLTFENMAGVFMLVAGGIVAGIFLIFI EIAYKRHKDARRKQMQLAFAAVNVWRKNLQQYHPTDITGPLNLSD PSVSTVV | NMDAR complete NR1 p (GenBank AAA21180.1) |
| 18 | ASTGGGSGGGGSSG | Linker-2 p |
| 19 | ASGGGGSGGGGSSG | Linker-2b p |
| 20 | IYIWAPLAGTCGVLLLSLVITLYC | CD8α transmembrane domain p |
| 21 | FWLPIGCAAFVVVCILGCILICWLTKKKYSSSVHDPNGEYMFMRAV NTAKKSRLTDVTL | ICOS transmembrane and intracellular domain p |
| — | GS | Linker-3 p |
| 22 | KRGRKKLLYIFKQPFMRPVQTTQEEDGCSCRFPEEEEGGCEL | CD137 (4-1BB) co-stimulatory domain p |
| 23 | RVKFSRSADAPAYQQGQNQLYNELNLGRREEYDVLDKRRGRDPE MGGKPRRKNPQEGLYNELQKDKMAEAYSEIGMKGERRRGKGHD GLYQGLSTATKDTYDALHMQALPPR | CD3 zeta chain signaling domain (activation domain) p |
| 24 | ATGGCTCTGCCTGTGACAGCTCTGCTGCTGCCTCTGGCCCTGC TGCTGCATGCTGCCAGACCTAGAGCCGCCTGCGATCCCAAGAT CGTGAATATCGGAGCCGTGCTGAGCACCCGGAAGCACGAGCAG ATGTTCAGAGAAGCCGTGAACCAGGCCAACAAGAGACACGGCA GCTGGAAGATCCAGCTGAACGCCACAAGCGTGACCCACAAGCC TAACGCCATTCAGATGGCCCTGAGCGTGTGCGAGGATCTGATC AGCTCTCAGGTGTACGCCATCCTGGTGTCTCACCCTCCAACACC TAACGACCACTTCACCCCTACACCTGTGTCTTACACCGCCGGCT TCTACAGAATCCCTGTGCTGGGCCTGACCACCAGAATGAGCATC TACAGCGACAAGAGCATCCACCTGAGCTTTCTGCGGACCGTGC CTCCTTACAGCCACCAGTCTAGCGTTTGGTTCGAGATGATGCGG GTGTACAGCTGGAACCACATCATCCTGCTGGTGTCCGACGACC ACGAAGGCAGAGCCGCTCAGAAGAGACTGGAAACCCTGCTGGA AGAGAGAGAGTCCAAGGCCGAGAAGGTGCTGCAGTTCGATCCC GGCACCAAGAACGTGACAGCCCTGCTGATGGAAGCCAAAGAAC TGGAAGCCAGAGTGATCATCCTGAGCGCCTCCGAAGATGATGC CGCCACCGTGTATAGAGCCGCCGCTATGCTGAATATGACCGGC | CAAR construct ATD-S1-S2 nt CD8 leader/ NMDAR ATD-S1- Linker1-S2/ Linker2/ CD8a TM/ CD137 co-stim/ CD3z signaling |

-continued

| SEQ ID NO | Sequence | Description |
|---|---|---|
| | AGCGGATACGTGTGGCTCGTGGGCGAGAGAGAGATTAGCGGAA<br>ACGCCCTGAGATACGCCCCTGATGGAATCCTGGGACTGCAGCT<br>GATCAACGGCAAGAACGAGAGCGCCCACATCTCTGATGCCGTG<br>GGAGTTGTGGCTCAGGCCGTGCATGAGCTGCTGGAAAAAGAGA<br>ACATCACCGATCCTCCACGGGGCTGCGTGGGCAACACCAACAT<br>CTGGAAAACAGGCCCACTGTTCAAGCGGGTGCTGATGAGCAGC<br>AAATACGCCGATGGCGTGACAGGCCGGGTCGAGTTTAATGAGG<br>ACGGCGACAGAAAGTTCGCCAACTACAGCATCATGAACCTGCA<br>GAACCGGAAGCTGGTGCAAGTGGGCATCTACAACGGCACCCAC<br>GTGATCCCCAACGACCGGAAGATTATCTGGCCTGGCGGCGAAA<br>CCGAGAAGCCCAGAGGCTACCAGATGAGCACCAGACTGAAGAT<br>TGTGACCATCCACCAAGAGCCTTTCGTGTACGTGAAGCCCACAC<br>TGAGCGACGGCACCTGTAAAGAAGAGTTCACCGTCAACGGCGA<br>CCCTGTGAAGAAAGTGATCTGCACAGGCCCCAACGATACAAGC<br>CCTGGCAGCCCTAGACACACCGTTCCTCAGTGCTGCTACGGCT<br>TCTGCATCGACCTGCTGATCAAGCTGGCCCGGACCATGAACTTC<br>ACCTACGAAGTGCACCTGGTGGCCGACGGCAAGTTTGGCACAC<br>AAGAGAGAGTGAACAACAGCAACAAGAAAGAATGGAACGGCAT<br>GATGGGCGAGCTGCTGTCTGGACAGGCCGACATGATTGTGGCC<br>CCTCTGACCATCAACAACGAGCGGGCCCAGTACATCGAGTTCA<br>GCAAGCCATTCAAGTACCAGGGCCTGACAATCCTGGTCAAGAAA<br>GGCACCCGGATCACCGGCATCAACGACCCCAGACTGAGAAATC<br>CCTCCGACAAGTTCATCTACGCCACAGTGAAGCAGAGCAGCGT<br>GGACATCTACTTCAGACGCCAGGTGGAACTGAGCACCATGTACA<br>GACACATGGAAAAGCACAACTACAGTCTGCCGCCGAGGCAAT<br>CCAGGCCGTCAGAGATAACAAGCTGCACGCCTTCATCTGGGAC<br>AGCGCCGTGCTGGAATTTGAGGCCAGCCAGAAGTGCGATCTGG<br>TCACCACCGGTGAACTGTTTTTCAGAAGCGGCTTTGGCATCGGC<br>ATGCGGAAGGACTCTCCCTGGAAGCAGAATGTGTCCCTGAGCA<br>TCCTGAAGTCTCACGAGAACGGCTTCATGGAAGATCTGGACAAG<br>ACCTGGGTCCGATACCAAGAGTGCGATAGCGCGTCGACCGGCG<br>GAGGATCTGGCGGAGGCGGATCTTCTGGCATCTATATCTGGGC<br>TCCTCTGGCCGGCACATGCGGAGTTCTGCTGCTGAGCCTGGTC<br>ATCACCCTGTACTGCAAGCGGGGCAGAAAGAAGCTGCTGTACA<br>TCTTCAAGCAGCCCTTCATGCGGCCCGTGCAGCAACCCAAGA<br>GGAAGATGGCTGCTCCTGCAGATTCCCTGAGGAAGAGGAAGGC<br>GGCTGCGAGCTGAGAGTGAAGTTCTCCAGATCCGCCGACGCTC<br>CTGCTTACCAGCAGGGACAGAACCAGCTGTATAACGAGCTGAA<br>CCTGGGGCGCAGAGAAGAGTACGACGTGCTGGACAAGCGGAG<br>AGGCAGAGATCCTGAGATGGGCGGCAAGCCCAGACGGAAGAAT<br>CCTCAAGAGGGCCTGTACAACGAACTCCAGAAAGACAAGATGG<br>CCGAGGCCTACAGCGAGATCGGAATGAAGGGCGAGCGCAGAA<br>GAGGCAAGGGACACGATGGACTGTATCAGGGCCTGTCTACCGC<br>CACCAAGGACACCTATGATGCCCTGCACATGCAGGCCCTGCCA<br>CCTAGATAA | |
| 25 | ATGGCTCTGCCTGTGACAGCTCTGCTGCTGCCTCTGGCCCTGC<br>TGCTGCATGCTGCCAGACCTAGAGCCGCCTGCGATCCCAAGAT<br>CGTGAATATCGGAGCCGTGCTGAGCACCCGGAAGCACGAGCAG<br>ATGTTCAGAGAAGCCGTGAACCAGGCCAACAAGAGACACGGCA<br>GCTGGAAGATCCAGCTGAACGCCACAAGCGTGACCCACAAGCC<br>TAACGCCATTCAGATGGCCCTGAGCGTGTGCGAGGATCTGATC<br>AGCTCTCAGGTGTACGCCATCCTGGTGTCTCACCCTCCAACACC<br>TAACGACCACTTCACCCCCTACACCTGTGTCTTACACCGCCGGCT<br>TCTACAGAATCCCTGTGCTGGGCCTGACCACCAGAATGAGCATC<br>TACAGCGACAAGAGCATCCACCTGAGCTTTCTGCGGACCGTGC<br>CTCCTTACAGCCACCAGTCTAGCGTTTGGTTCGAGATGATGCGG<br>GTGTACAGCTGGAACCACATCATCCTGCTGGTGTCCGACGACC<br>ACGAAGGCAGAGCCGCTCAGAAGAGACTGGAAACCCTGCTGGA<br>AGAGAGAGAGTCCAAGGCCGAGAAGGTGCTGCAGTTCGATCCC<br>GGCACCAAGAACGTGACAGCCCTGCTGATGGAAGCCAAAGAAC<br>TGGAAGCCAGAGTGATCATCCTGAGCGCCTCCGAAGATGATGC<br>CGCCACCGTGTATAGAGCCGCCGCTATGCTGAATATGACCGGC<br>AGCGGATACGTGTGGCTCGTGGGCGAGAGAGAGATTAGCGGAA<br>ACGCCCTGAGATACGCCCCTGATGGAATCCTGGGACTGCAGCT<br>GATCAACGGCAAGAACGAGAGCGCCCACATCTCTGATGCCGTG<br>GGAGTTGTGGCTCAGGCCGTGCATGAGCTGCTGGAAAAAGAGA<br>ACATCACCGATCCTCCACGGGGCTGCGTGGGCAACACCAACAT<br>CTGGAAAACAGGCCCACTGTTCAAGCGGGTGCTGATGAGCAGC<br>AAATACGCCGATGGCGTGACAGGCCGGGTCGAGTTTAATGAGG<br>ACGGCGACAGAAAGTTCGCCAACTACAGCATCATGAACCTGCA<br>GAACCGGAAGCTGGTGCAAGTGGGCATCTACAACGGCACCCAC<br>GTGATCCCCAACGACCGGAAGATTATCTGGCCTGGCGGCGAAA<br>CCGAGAAGCCCAGAGGCTACCAGATGAGCACCAGACTGAAGAT<br>TGTGACCATCCACCAAGAGCCTTTCGTGTACGTGAAGCCCACAC | CAAR construct<br>ATD-S1 nt<br>CD8 leader/<br>NMDAR ATD-S1/<br>Linker2/<br>CD8a TM/<br>CD137 co-stim/<br>CD3z signaling |

| SEQ ID NO | Sequence | Description |
|---|---|---|
| | TGAGCGACGGCACCTGTAAAGAAGAGTTCACCGTCAACGGCGA CCCTGTGAAGAAAGTGATCTGCACAGGCCCCAACGATACAAGC CCTGGCAGCCCTAGACACACCGTTCCTCAGTGCTGCTACGGCT TCTGCATCGACCTGCTGATCAAGCTGGCCCGGACCATGAACTTC ACCTACGAAGTGCACCTGGTGGCCGACGGCAAGTTTGGCACAC AAGAGAGAGTGAACAACAGCAACAAGAAAGAATGGAACGGCAT GATGGGCGAGCTGCTGTCTGGACAGGCCGACATGATTGTGGCC CCTCTGACCATCAACAACGAGCGGGCCCAGTACATCGAGTTCA GCAAGCCATTCAAGTACCAGGGCCTGACAATCCTGGTCAAGAAA GCGTCGACCGGCGGAGGATCTGGCGGAGGCGGATCTTCTGGC ATCTATATCTGGGCTCCTCTGGCCGGCACATGCGGAGTTCTGCT GCTGAGCCTGGTCATCACCCTGTACTGCAAGCGGGGCAGAAAG AAGCTGCTGTACATCTTCAAGCAGCCCTTCATGCGGCCCGTGCA GACAACCCAAGAGGAAGATGGCTGCTCCTGCAGATTCCCTGAG GAAGAGGAAGGCGGCTGCGAGCTGAGAGTGAAGTTCTCCAGAT CCGCCGACGCTCCTGCTTACCAGCAGGGACAGAACCAGCTGTA TAACGAGCTGAACCTGGGGCGCAGAGAAGAGTACGACGTGCTG GACAAGCGGAGAGGCAGAGATCCTGAGATGGGCGGCAAGCCC AGACGGAAGAATCCTCAAGAGGGCCTGTACAACGAACTCCAGA AAGACAAGATGGCCGAGGCCTACAGCGAGATCGGAATGAAGGG CGAGCGCAGAAGAGGCAAGGGACACGATGGACTGTATCAGGG CCTGTCTACCGCCACCAAGGACACCTATGATGCCCTGCACATGC AGGCCCTGCCACCTAGATAA | |
| 26 | ATGGCTCTGCCTGTGACAGCTCTGCTGCTGCCTCTGGCCCTGC TGCTGCATGCTGCCAGACCTAGAGCCGCCTGCGATCCCAAGAT CGTGAATATCGGAGCCGTGCTGAGCACCCGGAAGCACGAGCAG ATGTTCAGAGAAGCCGTGAACCAGGCCAACAAGAGACACGGCA GCTGGAAGATCCAGCTGAACGCCACAAGCGTGACCCACAAGCC TAACGCCATTCAGATGGCCCTGAGCGTGTGCGAGGATCTGATC AGCTCTCAGGTGTACGCCATCCTGGTGTCTCACCCTCCAACACC TAACGACCACTTCACCCCTACACCTGTGTCTTACACCGCCGGCT TCTACAGAATCCCTGTGCTGGGCCTGACCACCAGAATGAGCATC TACAGCGACAAGAGCATCCACCTGAGCTTTCTGCGGACCGTGC CTCCTTACAGCCACCAGTCTAGCGTTTGGTTCGAGATGATGCGG GTGTACAGCTGGAACCACATCATCCTGCTGGTGTCCGACGACC ACGAAGGCAGAGCCGCTCAGAAGAGACTGGAAACCCTGCTGGA AGAGAGAGAGTCCAAGGCCGAGAAGGTGCTGCAGTTCGATCCC GGCACCAAGAACGTGACAGCCCTGCTGATGGAAGCCAAAGAAC TGGAAGCCAGAGTGATCATCCTGAGCGCCTCCGAAGATGATGC CGCCACCGTGTATAGAGCCGCCGCTATGCTGAATATGACCGGC AGCGGATACGTGTGGCTCGTGGGCGAGAGAGAGATTAGCGGAA ACGCCCTGAGATACGCCCCTGATGGAATCCTGGGACTGCAGCT GATCAACGGCAAGAACGAGAGCGCCCACATCTCTGATGCCGTG GGAGTTGTGGCTCAGGCCGTGCATGAGCTGCTGGAAAAAGAGA ACATCACCGATCCTCCACGGGGCTGCGTGGGCAACACCAACAT CTGGAAAACAGGCCCACTGTTCAAGCGGGTGCTGATGAGCAGC AAATACGCCGATGGCGTGACAGGCCGGGTCGAGTTTAATGAGG ACGGCGACAGAAAGTTCGCCAACTACAGCATCATGAACCTGCA GAACCGGAAGCTGGTGCAAGTGGGCATCTACAACGGCACCCAC GTGATCCCCAACGACCGGAAGATTATCTGGCCTGGCGGCGAAA CCGAGAAGCCCAGAGGCTACCAGGCGTCGACCGGCGGAGGAT CTGGCGGAGGCGGATCTTCTGGCATCTATATCTGGGCTCCTCT GGCCGGCACATGCGGAGTTCTGCTGCTGAGCCTGGTCATCACC CTGTACTGCAAGCGGGGCAGAAAGAAGCTGCTGTACATCTTCAA GCAGCCCTTCATGCGGCCCGTGCAGACAACCCAAGAGGAAGAT GGCTGCTCCTGCAGATTCCCTGAGGAAGAGGAAGGCGGCTGCG AGCTGAGAGTGAAGTTCTCCAGATCCGCCGACGCTCCTGCTTAC CAGCAGGGACAGAACCAGCTGTATAACGAGCTGAACCTGGGGC GCAGAGAAGAGTACGACGTGCTGGACAAGCGGAGAGGCAGAG ATCCTGAGATGGGCGGCAAGCCCAGACGGAAGAATCCTCAAGA GGGCCTGTACAACGAACTCCAGAAAGACAAGATGGCCGAGGCC TACAGCGAGATCGGAATGAAGGGCGAGCGCAGAAGAGGCAAG GGACACGATGGACTGTATCAGGGCCTGTCTACCGCCACCAAGG ACACCTATGATGCCCTGCACATGCAGGCCCTGCCACCTAGATAA | CAAR construct ATD nt CD8 leader/ NMDAR ATD/ Linker2/ CD8a TM/ CD137 co-stim/ CD3z signaling |
| 27 | ATGGCTCTGCCTGTGACAGCTCTGCTGCTGCCTCTGGCCCTGC TGCTGCATGCTGCCAGACCTAGAGCCGCCTGCGATCCCAAGAT CGTGAATATCGGAGCCGTGCTGAGCACCCGGAAGCACGAGCAG ATGTTCAGAGAAGCCGTGAACCAGGCCAACAAGAGACACGGCA GCTGGAAGATCCAGCTGAACGCCACAAGCGTGACCCACAAGCC TAACGCCATTCAGATGGCCCTGAGCGTGTGCGAGGATCTGATC AGCTCTCAGGTGTACGCCATCCTGGTGTCTCACCCTCCAACACC TAACGACCACTTCACCCCTACACCTGTGTCTTACACCGCCGGCT TCTACAGAATCCCTGTGCTGGGCCTGACCACCAGAATGAGCATC | CAAR construct (ICOS) nt CD8 leader/ NMDAR ATD/ Linker2b/ ICOS TM-ICD/ Linker3/ CD137 co-stim/ CD3z signaling |

-continued

| SEQ ID NO | Sequence | Description |
|---|---|---|
| | TACAGCGACAAGAGCATCCACCTGAGCTTTCTGCGGACCGTGC<br>CTCCTTACAGCCACCAGTCTAGCGTTTGGTTCGAGATGATGCGG<br>GTGTACAGCTGGAACCACATCATCCTGCTGGTGTCCGACGACC<br>ACGAAGGCAGAGCCGCTCAGAAGAGACTGGAAACCCTGCTGGA<br>AGAGAGAGAGTCCAAGGCCGAGAAGGTGCTGCAGTTCGATCCC<br>GGCACCAAGAACGTGACAGCCCTGCTGATGGAAGCCAAAGAAC<br>TGGAAGCCAGAGTGATCATCCTGAGCGCCTCCGAAGATGATGC<br>CGCCACCGTGTATAGAGCCGCCGCTATGCTGAATATGACCGGC<br>AGCGGATACGTGTGGCTCGTGGGCGAGAGAGAGATTAGCGGAA<br>ACGCCCTGAGATACGCCCCTGATGGAATCCTGGGACTGCAGCT<br>GATCAACGGCAAGAACGAGAGCGCCCACATCTCTGATGCCGTG<br>GGAGTTGTGGCTCAGGCCGTGCATGAGCTGCTGGAAAAAGAGA<br>ACATCACCGATCCTCCACGGGGCTGCGTGGGCAACACCAACAT<br>CTGGAAAACAGGCCCACTGTTCAAGCGGGTGCTGATGAGCAGC<br>AAATACGCCGATGGCGTGACAGGCCGGGTCGAGTTTAATGAGG<br>ACGGCGACAGAAAGTTCGCCAACTACAGCATCATGAACCTGCA<br>GAACCGGAAGCTGGTGCAAGTGGGCATCTACAACGGCACCCAC<br>GTGATCCCCAACGACCGGAAGATTATCTGGCCTGGCGGCGAAA<br>CCGAGAAGCCCAGAGGCTACCAGGCTAGCGGCGGAGGCGGAT<br>CTGGTGGCGGAGGATCTTCTGGATTCTGGCTGCCTATTGGCTG<br>CGCCGCCTTTGTGGTCGTGTGTATCCTGGGCTGCATCCTGATCT<br>GCTGGCTGACCAAGAAAAAGTACAGCAGCAGCGTGCACGACCC<br>CAACGGCGAGTACATGTTCATGAGAGCCGTGAACACCGCCAAG<br>AAGTCCAGACTGACCGACGTGACACTGGGCAGCAAGCGGGGAA<br>GAAAGAAGCTGCTGTATATCTTCAAGCAGCCCTTCATGCGGCCC<br>GTGCAGACCACACAAGAGGAAGATGGCTGCTCCTGCAGATTCC<br>CCGAGGAAGAAGAAGGCGGCTGCGAGCTGAGAGTGAAGTTCAG<br>CAGATCCGCTGACGCCCCTGCCTATCAGCAGGGACAGAACCAG<br>CTGTACAACGAGCTGAACCTGGGGAGAAGAGAAGAGTACGACG<br>TGCTGGACAAGCGGAGAGGCAGAGATCCTGAGATGGGCGGCA<br>AGCCCAGACGGAAGAATCCTCAAGAGGGCCTGTATAATGAGCT<br>GCAGAAAGACAAGATGGCCGAGGCCTACAGCGAGATCGGAATG<br>AAGGGCGAGCGCAGAAGAGGCAAGGGACACGATGGACTGTAC<br>CAGGGCCTGAGCACCGCCACCAAGGATACCTATGATGCCCTGC<br>ACATGCAGGCCCTGCCTCCAAGATAA | |
| 28 | MALPVTALLLPLALLLHAARPRAACDPKIVNIGAVLSTRKHEQMFRE<br>AVNQANKRHGSWKIQLNATSVTHKPNAIQMALSVCEDLISSQVYAIL<br>VSHPPTPNDHFTPTPVSYTAGFYRIPVLGLTTRMSIYSDKSIHLSFLR<br>TVPPYSHQSSVwFEMMRVYSWNHIILLVSDDHEGRAAQKRLETLL<br>EERESKAEKVLQFDPGTKNVTALLMEAKELEARVIILSASEDDAATV<br>YRAAAMLNMTGSGYVWLVGEREISGNALRYAPDGILGLQLINGKNE<br>SAHISDAVGVVAQAVHELLEKENITDPPRGCVGNTNIWKTGPLFKR<br>VLMSSKYADGVTGRVEFNEDGDRKFANYSIMNLQNRKLVQVGIYN<br>GTHVIPNDRKIIWPGGETEKPRGYQMSTRLKIVTIHQEPFVYVKPTL<br>SDGTCKEEFTVNGDPVKKVICTGPNDTSPGSPRHTVPQCCYGFCI<br>DLLIKLARTMNFTYEVHLVADGKFGTQERVNNSNKKEWNGMMGEL<br>LSGQADMIVAPLTINNERAQYIEFSKPFKYQGLTILVKKGTRITGIND<br>PRLRNPSDKFIYATVKQSSVDIYFRRQVELSTMYRHMEKHNYESAA<br>EAIQAVRDNKLHAFIWDSAVLEFEASQKCDLVTTGELFFRSGFGIG<br>MRKDSPWKQNVSLSILKSHENGFMEDLDKTWVRYQECDSASTGG<br>GSGGGGSSGIYIWAPLAGTCGVLLLSLVITLYCKRGRKKLLYIFKQP<br>FMRPVQTTQEEDGCSCRFPEEEEGGCELRVKFSRSADAPAYQQG<br>QNQLYNELNLGRREEYDVLDKRRGRDPEMGGKPRRKNPQEGLYN<br>ELQKDKMAEAYSEIGMKGERRRGKGHDGLYQGLSTATKDTYDALH<br>MQALPPR | CAAR construct<br>ATD-S1-S2 p<br>CD8 leader/<br>NMDAR ATD-S1-<br>Linker1-S2/<br>Linker2/<br>CD8a TM/<br>CD137 co-stim/<br>CD3z signaling |
| 29 | MALPVTALLLPLALLLHAARPRAACDPKIVNIGAVLSTRKHEQMFRE<br>AVNQANKRHGSWKIQLNATSVTHKPNAIQMALSVCEDLISSQVYAIL<br>VSHPPTPNDHFTPTPVSYTAGFYRIPVLGLTTRMSIYSDKSIHLSFLR<br>TVPPYSHQSSVWFEMMRVYSWNHIILLVSDDHEGRAAQKRLETLL<br>EERESKAEKVLQFDPGTKNVTALLMEAKELEARVIILSASEDDAATV<br>YRAAAMLNMTGSGYVWLVGEREISGNALRYAPDGILGLQLINGKNE<br>SAHISDAVGVVAQAVHELLEKENITDPPRGCVGNTNIWKTGPLFKR<br>VLMSSKYADGVTGRVEFNEDGDRKFANYSIMNLQNRKLVQVGIYN<br>GTHVIPNDRKIIWPGGETEKPRGYQMSTRLKIVTIHQEPFVYVKPTL<br>SDGTCKEEFTVNGDPVKKVICTGPNDTSPGSPRHTVPQCCYGFCI<br>DLLIKLARTMNFTYEVHLVADGKFGTQERVNNSNKKEWNGMMGEL<br>LSGQADMIVAPLTINNERAQYIEFSKPFKYQGLTILVKKASTGGGSG<br>GGGSSSGIYIWAPLAGTCGVLLLSLVITLYCKRGRKKLLYIFKQPFMR<br>PVQTTQEEDGCSCRFPEEEEGGCELRVKFSRSADAPAYQQGGQNQ<br>LYNELNLGRREEYDVLDKRRGRDPEMGGKPRRKNPQEGLYNELQ<br>KDKMAEAYSEIGMKGERRRGKGHDGLYQGLSTATKDTYDALHMQ<br>ALPPR | CAAR construct<br>ATD-S1 p<br>CD8 leader/<br>NMDAR ATD-S1/<br>Linker2/<br>CD8a TM/<br>CD137 co-stim/<br>CD3z signaling |

-continued

| SEQ ID NO | Sequence | Description |
|---|---|---|
| 30 | MALPVTALLLPLALLLHAARPRAACDPKIVNIGAVLSTRKHEQMFRE AVNQANKRHGSWKIQLNATSVTHKPNAIQMALSVCEDLISSQVYAIL VSHPPTPNDHFTPTPVSYTAGFYRIPVLGLTTRMSIYSDKSIHLSFLR TVPPYSHQSSVWFEMMRVYSWNHIILLVSDDHEGRAAQKRLETLL EERESKAEKVLQFDPGTKNVTALLMEAKELEARVIILSASEDDAATV YRAAAMLNMTGSGYVWLVGEREISGNALRYAPDGILGLQLINGKNE SAHISDAVGVVAQAVHELLEKENITDPPRGCVGNTNIWKTGPLFKR VLMSSKYADGVTGRVEFNEDGDRKFANYSIMNLQNRKLVQVGIYN GTHVIPNDRKIIWPGGETEKPRGYQASTGGGSGGGGSSGIYIWAPL AGTCGVLLLSLVITLYCKRGRKKLLYIFKQPFMRPVQTTQEEDGCS CRFPEEEEGGCELRVKFSRSADAPAYQQGQNQLYNELNLGRREE YDVLDKRRGRDPEMGGKPRRKNPQEGLYNELQKDKMAEAYSEIG MKGERRRGKGHDGLYQGLSTATKDTYDALHMQALPPR | CAAR construct ATD p CD8 leader/ NMDAR ATD/ Linker2/ CD8a TM/ CD137 co-stim/ CD3z signaling |
| 31 | MALPVTALLLPLALLLHAARPRAACDPKIVNIGAVLSTRKHEQMFRE AVNQANKRHGSWKIQLNATSVTHKPNAIQMALSVCEDLISSQVYAIL VSHPPTPNDHFTPTPVSYTAGFYRIPVLGLTTRMSIYSDKSIHLSFLR TVPPYSHQSSVWFEMMRVYSWNHIILLVSDDHEGRAAQKRLETLL EERESKAEKVLQFDPGTKNVTALLMEAKELEARVIILSASEDDAATV YRAAAMLNMTGSGYVWLVGEREISGNALRYAPDGILGLQLINGKNE SAHISDAVGVVAQAVHELLEKENITDPPRGCVGNTNIWKTGPLFKR VLMSSKYADGVTGRVEFNEDGDRKFANYSIMNLQNRKLVQVGIYN GTHVIPNDRKIIWPGGETEKPRGYQASGGGGSGGGGSSGFWLPIG CAAFVVVCILGCILICWLTKKKYSSSVHDPNGEYMFMRAVNTAKKS RLTDVTLGSKRGRKKLLYIFKQPFMRPVQTTQEEDGCSCRFPEEEE GGCELRVKFSRSADAPAYQQGQNQLYNELNLGRREEYDVLDKRR GRDPEMGGKPRRKNPQEGLYNELQKDKMAEAYSEIGMKGERRRG KGHDGLYQGLSTATKDTYDALHMQALPPR | CAAR construct (ICOS) p CD8 leader/ NMDAR ATD/ Linker2b/ ICOS TM-ICD/ Linker3/ CD137 co-stim/ CD3z signaling |

In a further aspect, the invention relates to a genetically modified immune cell comprising a nucleic acid molecule encoding a CAAR as described herein, or a vector comprising such a nucleic acid molecule and/or expressing a CAAR as described herein.

In one embodiment, the genetically modified immune cell is selected from the group consisting of a T cell, an NK cell, a macrophage or a dendritic cell.

In one embodiment, the genetically modified immune cell as described herein is a T lymphocyte (T cell) and said T lymphocyte is a CD8+ and/or CD4+ cytotoxic T lymphocyte, or mixture thereof.

In some embodiments, CAAR-engineered immune cells can be edited for deletion of TCRs to avoid GVHD reactions. In some embodiments, CAAR-engineered immune cells can be edited for deletion of HLA to avoid allogeneic rejection and become "universal CAAR-T cells".

In preferred embodiments the immune cell is preferably a T lymphocyte, an NK cell, a macrophage or a dendritic cell. In some preferred embodiments, the immune cell is cytotoxic, preferably cytotoxic towards autoantibody-presenting and/or secreting B cells. Cytotoxic immune cells are known in the field to exhibit cytolytic and/or other beneficial activity in response to unwanted agents, cells or pathogens. By directing the activity of these cells to particular immunogenic targets, namely the autoantigens described herein, pathogenic cells can be eliminated by the corresponding activity of the immune cell described herein.

In a preferred embodiment, the immune cell is a T lymphocyte, preferably a cytotoxic T lymphocyte or a T helper cell.

In some embodiments, the CAAR-engineered immune cell could be engineered to additionally co-express cytokines (such as IL-15, IL-12, IFN-gamma, IFN-alpha, GM-CSF, FLT3L, IL-21, IL-23) or co-stimulatory ligands (CD80, CD86, CD40L) to improve the immune therapeutic effects.

In some embodiments, the CAAR-engineered immune cell could be engineered to additionally co-express siRNAs or shRNAs or miRNAs to down-regulate, or could be genetically edited with CRISPR/Cas, to knock-out expression of the T cell receptor and the major histocompatibility complex, such that these cells can be used as allogeneic cell therapies.

In some embodiments, the CAAR-engineered immune cell could be engineered to additionally co-express siRNAs or shRNAs or miRNAs to down-regulate, or could be genetically edited with the CRISPR/Cas, to knock-out expression of check point molecules on the T cell surface (PD1, Tim3, LAG, etc. . . . ).

Combined approaches employing down-regulation of the major histocompatibility complex or check point molecules on the T cell surface lead to additional, potentially synergistic effects, in optimizing the local immune environment to enhance the cytolytic effect of the CAAR-engineered immune cells of the invention against the pathogenic B cells.

In a further aspect, the invention relates to an immune cell as described herein for use in the treatment or prevention of a neurological autoimmune disease primarily targeting the central nervous system.

In some embodiments, the invention relates to an immune cell as described herein for use in the treatment or prevention of an autoantibody-mediated psychiatric condition.

In one embodiment, the treatment or prevention of a neurological autoimmune disease primarily targeting the peripheral nervous system is not encompassed by the invention. In one embodiment, such a disease is myasthenia gravis.

In some embodiments, the invention relates to an immune cell as described herein for use in the treatment or prevention of autoimmune encephalopathy or encephalomyelopathy.

The invention therefore relates to the medical use of the CAAR-engineered immune cells. The invention therefore also encompasses methods for treating or preventing a medical condition as described herein, comprising the administration of an immune cell as described herein (comprising/expressing a CAAR of the present invention) to a subject in need thereof.

In some embodiments, the autoimmune encephalopathy is a medical condition associated with autoantibodies against the N-methyl-D-aspartate receptor (NMDAR).

In preferred embodiments, the medical condition to be treated is anti-NMDAR encephalitis.

Subject matter of the present invention is therefore the medical use of the CAAR or corresponding engineered immune cells of the present invention in therapy of a disease or a condition in a subject, said disease or condition being associated with anti-NMDAR antibodies, and in a specific embodiment having in addition at least one clinical symptom or clinical condition selected from the group comprising the clinical symptoms/conditions according to the following list (ICD numbers in parentheses refer to the WHO International Classification of Diseases which defines the clinical conditions):

psychiatric abnormalities including depression (F32), mania with psychotic symptoms (F30.2), anxiety (F06.4), phobic anxiety (F40), delusions (F22.0), obsessive-compulsive disorder (F42), organic delusional disorder (F06.3), catatonia (F06.1, F20.2), acute polymorphic psychotic disorder (F23.0, F23.1), dissociative disorders (F44)

movement disorders including dyskinesias/dystonia (G24), myoclonus (G25.3), tremor (G25.0, G25-1, G25-2), tics (F95, G25.69)

epileptic seizures (G40)

hypoventilation (R06.89)

mild cognitive impairment (F06.7)

dementia in Alzheimer's disease (F00), vascular dementia (F01), dementia in other diseases (F02)

pregnancy.

The invention is characterized by the following advantages:

Highly selective removal of the NMDA receptor antibody producing B-cells;

Short-term therapy effects and long-term, potentially permanent, depletion of pathogenic antibodies;

Prevention, or significant reduction in risk, of clinical relapses;

No or reduced severe general immunosuppression, i.e. reduced risk of infections or sepsis;

No or reduced negative effect on vaccinations;

No or reduced toxic immunological side effects;

Unwanted immunological responses are treatable, for example via IL-6-antagonists;

Immediate (preferably within hours) depletion of the pathogenic B-cell;

Low administration number, preferably a single administration of the cells is carried out, e.g. via an intravenous route.

According to the invention, the embodiments of any given aspect are considered to apply to other aspects and embodiments, such that combinations of particular embodiments as disclosed herein are contemplated. For example, embodiments disclosed with respect to the medical treatment may be incorporated as functional features of the CAARs, and vice versa.

DETAILED DESCRIPTION OF THE INVENTION

All cited documents of the patent and non-patent literature are hereby incorporated by reference in their entirety.

Autoantigen and Disease Description:

The invention relates to a chimeric autoantibody receptor (CAAR) that enables targeting of an immune cell to autoantibody producing B cells, wherein the CAAR comprises an autoantigen or fragment thereof that is bound by autoantibodies associated with a neurological autoimmune disease primarily targeting the central nervous system.

The autoantigen of the CAAR therefore represents a targeting subunit, equivalent to an extracellular antigen-binding domain of a CAR, that targets the immune cell to the B cell to be depleted.

As used herein, the term "autoantigen or fragment thereof that is bound by autoantibodies associated with a neurological autoimmune disease primarily targeting the central nervous system" represents a functional definition of the autoantigen comprised within the CAAR. A skilled person is capable of determining the autoantigens of this class and the associated medical conditions. Binding between an autoantigen and antibody is, as such, an established phenomenon and reflects essentially the physical interaction between any given antibody and its target.

As used herein, the term "neurological autoimmune disease primarily targeting the central nervous system" relates to any medical condition with an autoimmune component, in which autoantibodies are present against specific autoantigens predominantly expressed in the central nervous system, in comparison to the peripheral nervous system, or any medical condition with an autoimmune component, in which the binding of autoantibodies to specific autoantigens expressed in the central nervous system is the predominant pathogenic effect of the disease.

Various neurological autoimmune conditions are known to a skilled person, in which the autoantibodies target typically either autoantigens of primarily the central or peripheral nervous system. Medical conditions are however also known, in which autoantibodies are directed against targets present in both the central and peripheral nervous systems. The present invention therefore envisages the use of an autoantigen in the CAAR of the invention that is an autoantibody target in a disease, in which said autoantibodies predominantly target components of the central nervous system, or in which the pathogenic effect of said autoantibodies is caused by the autoantibodies targeting an autoantigen in the central nervous system.

As used herein, the "central nervous system" or CNS refers to the part of the nervous system consisting of the brain and spinal cord. The CNS is contained within the dorsal body cavity, with the brain housed in the cranial cavity and the spinal cord in the spinal canal. The CNS is divided in white and gray matter. This can also be seen macroscopically on brain tissue. The white matter consists of axons and oligodendrocytes, while the gray matter consists of neurons and unmyelinated fibers. Both tissues include a number of glial cells (although the white matter contains more), which are often referred to as supporting cells of the CNS.

From and to the spinal cord are projections of the peripheral nervous system in the form of spinal nerves. The nerves connect the spinal cord to skin, joints, muscles etc. and allow for the transmission of efferent motor as well as afferent sensory signals and stimuli. This allows for voluntary and involuntary motions of muscles, as well as the perception of senses.

As used herein, the "peripheral nervous system" (PNS) consists of the nerves and ganglia outside the brain and spinal cord. The main function of the PNS is to connect the CNS to the limbs and organs, essentially serving as a relay between the brain and spinal cord and the rest of the body. Unlike the CNS, the PNS is not protected by the vertebral column and skull, or by the blood-brain barrier.

One example of a neurological autoimmune condition primarily targeting the peripheral nervous system, which is—in some embodiments—not encompassed by the present invention, is the condition myasthenia gravis. Myasthenia gravis is a chronic autoimmune neuromuscular disease that causes weakness in the skeletal muscles, which are responsible for breathing and moving parts of the body, including the arms and legs. Myasthenia gravis is caused by an error in the transmission of nerve impulses to muscles. It occurs when normal communication between the nerve and muscle is interrupted at the neuromuscular junction—the place where nerve cells connect with the muscles they control. In myasthenia gravis, autoantibodies block and/or destroy the receptors for acetylcholine at the neuromuscular junction, which prevents the muscle from contracting. In most individuals with myasthenia gravis, this is caused by antibodies to the acetylcholine receptor itself. However, antibodies to other proteins, such as MuSK (Muscle-Specific Kinase) protein, can also lead to impaired transmission at the neuromuscular junction. As such, the condition myasthenia gravis is one example of a neurological autoimmune condition primarily targeting the peripheral nervous system, and not the central nervous system, as according to the present invention. In some embodiments, the invention does not encompass autoantigens targeted in neuromuscular disease, when these autoantigens are targeted primarily in the peripheral nervous system.

Emerging research now shows that autoantibodies do have access to the CNS (Zong et al 2017) and that autoantibody-producing B cells are present in the CNS. Under normal conditions, immunoglobulins go through the blood brain barrier (BBB) at a low rate; a good example is immunoglobulin G (IgG). IgG concentration in the cerebrospinal fluid (CSF) is approximately 1% of the levels in the peripheral circulation. This indicates that once the autoantibodies reach the CNS they can cause disease as it has been observed in autoimmune encephalitis. In certain situations, the BBB may also become leaky because of stroke, brain trauma, hemorrhages, microangiopathy, or brain tumors, and antibody penetration might increase.

As used herein, the term "autoantibody-mediated psychiatric condition" relates to any medical condition comprising the presence of autoantibodies, preferably directed to an autoantigen primarily targeted in the central nervous system, in which psychiatric (neuropsychiatric) symptoms are also observed). A number of central nervous system disorders, including encephalitis and severe psychiatric disorders, have been demonstrated to associate with specific neuronal surface autoantibodies (NSAbs). It has become clear that specific autoantibodies targeting neuronal surface antigens and ion channels cause severe mental disturbances, i.e. lead to neuropsychiatric symptoms. A number of studies show the presence of autoantibodies in specific mental conditions such as schizophrenia and bipolar disorders. Additional disorders relate to neuropsychiatric disorders such as schizophrenia, bipolar disorder, MDD, substance-induced psychosis, Huntington's disease, Alzheimer's disease, and neuropsychiatric systemic lupus erythematosus (Zong et al, 2017).

In some embodiments, the diseases to be treated are an autoimmune encephalopathy or encephalomyelopathy.

An "encephalopathy" is typically any disorder or disease of the brain, especially chronic degenerative conditions. Encephalopathy may refer to permanent (or degenerative) brain injury, or a reversible injury. It can be due to direct injury to the brain, or illness remote from the brain. Symptoms often include intellectual disability, irritability, agitation, delirium, confusion, somnolence, stupor, coma and psychosis. As used herein, an "autoimmune encephalopathy" refers to any brain disease with an autoimmune component. As used herein, an "autoimmune encephalomyelopathy" is any disease that affects both the brain and the spinal cord with an autoimmune component.

Anti-N-methyl-D-aspartate (NMDA) receptor encephalitis is a form of encephalitis occurring often in women and is associated with antibodies against NR1 and/or NR2 subunits of the NMDA receptor, although primarily the NR1 subunit.

Anti-NMDA receptor encephalitis was first described several years ago in multiple large studies that characterized the clinical syndrome in detail (Dalmau et al. 2008). Patients with anti-NMDAR encephalitis suffer from a severe form of encephalitis with characteristic clinical multistage features, predominantly affecting children and young women. It progresses from psychiatric symptoms, memory deficits, and epileptic seizures into a state of loss of consciousness, autonomic dysfunction, dyskinesias and hypoventilation (Dalmau et al. 2011, Prüss et al. 2010, Prüss et al. 2013). Hallmark of the disease are antibodies against the NR1 subunit of the NMDAR1. This has profoundly changed the therapeutic concept in encephalitis, since NMDAR encephalitis was not recognized as a distinct subgroup of encephalitis before 2007. Therefore, it was previously considered as encephalitis of unknown etiology and was not adequately treated.

The NMDAR NR1 is a component of NMDA receptor complexes that function as heterotetrameric, ligand-gated ion channels with high calcium permeability and voltage-dependent sensitivity to magnesium. Channel activation requires binding of the neurotransmitter glutamate to the epsilon subunit, glycine binding to the zeta subunit, plus membrane depolarization to eliminate channel inhibition by Mg2+. A number of protein isoforms of the NMDAR NR1 protein are known, such as, without limitation, those of the Gene Bank Acession numbers: XP_011516885.1, XP_005266130.1, XP_005266129.1, XP_005266128.1, NP_001172020.1, NP_001172019.1, NP_000823.4, NP_015566.1, NP_067544.1. Any one or more of said sequences or isoforms or functionally analogous derivatives thereof may be employed as the autoantigen of the CAAR described herein.

The NMDAR has a variety of physiological roles and any dysfunction, either enhanced or decreased activity, may result in neuropsychiatric disorders, such as schizophrenia, bipolar disorder, MDD, substance-induced psychosis, Huntington's disease, Alzheimer's disease, and neuropsychiatric systemic lupus erythematosus (NPSLE). The NMDAR therefore plays a critical role in multiple psychiatric disorders including depression. In addition, a subgroup of patients with atypical dementia harbor anti-NMDAR1 antibodies, removal of which by unspecific removal of all antibodies resulted in clinical improvement in selected cases (Prüss et al. 2010, Doss et al. 2014). Furthermore, autism can occur in the children of mothers suffering from autoantibody-mediated disorders. Several studies have found a correlation between the presence of circulating maternal autoantibodies and neuronal dysfunction in the neonate (Fox-Edmiston et al, 2015). Specifically, maternal anti-brain autoantibodies, which may access the fetal compartment during gestation, have been identified as one risk factor for developing Autism Spectrum Disorder (ASD). The presence of NMDAR-autoantibodies may therefore lead to autism in offspring of diseased mothers, such that the present invention also represents potential treatment of such disorders and/or a prophylactic approach towards avoiding such disease in children.

In contrast to anti-NMDAR in autoimmune encephalitis, which mainly targets the NR1 subunit, autoantibodies have been found that target the NR2 subunit of NMDAR, and these were associated with depression in systemic lupus erythematosus (SLE) patients (Lapteva et al. 2006). In some embodiments of the invention, the autoantigen encoded by the nucleic acid sequence comprises or consists of a protein selected from the group consisting of leucine-rich glioma-inactivated 1 (LGI1), α-amino-3-hydroxy-5-methyl-4-isoxazolepropionic acid receptor (AMPAR), Ig-Like Domain-Containing Protein 5 (IgLON5), Metabotropic glutamate receptor 5 (mGluR5), glutamic acid decarboxylase (GAD), contactin-associated protein-like 2 (CASPR2), a gamma-aminobutyric acid (GABA) receptor, such as GABA-A and/or GABA-B, myelin oligodendrocyte glycoprotein (MOG) and aquaporin-4 (AQP4), or one or more fragments thereof.

The above-mentioned autoantigens are known targets of autoantibodies in neurological autoimmune disease primarily targeting the central nervous system.

AMPAR is an ionotropic glutamate receptor which mediates the fast excitatory neurotransmission in the CNS. Lai and colleagues first reported autoantibodies to AMPAR in limbic encephalitis (Lai et al, 2009). The clinical features of this type of autoimmune encephalitis are short-term memory deficits, emotional/behavioral changes, and seizures, frequent association with paraneoplastic disease, treatment responsiveness and has a tendency to relapse.

Recent research has shown that antigenic targets within the voltage-gated potassium channel (VGKC) complex play a pathophysiological role in autoimmune neurology, as they are bound by autoantibodies which target the extracellular domains of these membrane proteins. For example, autoantibodies are known to bind both leucine-rich glioma-inactivated 1 (LGI1) and contactin-associated protein-like 2 (CASPR2). Patients with LGI1 or CASPR2 antibodies are predominantly male, with typical onset in late-middle age, and show symptoms of limbic encephalitis (a form of encephalitis, a disease characterized by inflammation of the brain, caused by autoantibodies), including seizures, amnesia and cognitive disturbance.

IgLON5-associated encephalitis is a syndrome with different clinical presentations comprising sleep dysfunction, bulbar dysfunction, chorea, and progressive supranuclear palsy-like symptoms. Patients have been reported with IgLON5-associated encephalitis presenting with rapidly progressive cognitive decline, inflammatory lesions on brain magnetic resonance imaging, oligoclonal bands on cerebrospinal fluid and anti-IgLON5 antibodies of the IgG1 class (Montagna et al, 2018).

The metabotropic glutamate receptor 5 (mGluR5) has been reported as an autoantigen in patients with Hodgkin lymphoma (HL) and limbic encephalopathy (Ophelia syndrome) (Lancaster et al, 2011).

GABA-A receptors are ionotropic receptors and GABA is the ligand. Subunits of GABA-AR have a different distribution in the brain and may respond with a different sensitivity to GABA, leading to a different function. A decline in GABA-AR signaling triggers hyperactivity in neurological disorders such as insomnia, anxiety, and epilepsy. Autoantibodies to GABA-A receptors were recently identified in autoimmune encephalitis (Zong 2017).

GABA-B receptors are metabotropic transmembrane receptors that are linked to G-protein-gated potassium channels. Mice which lack functional GABA(B) receptors, showed more anxiety and decreased immobility (antidepressant-like behavior). Autoantibodies to the GABA-BR (anti-GABABR) were reported in limbic encephalitis (Zong 2017).

Autoantibodies against Aquaporin-4 (AQP4) have been found in the majority of patients with neuromyelitis optica spectrum disorder (NMOSD) and the detection of AQP4 autoantibodies is used to classify seropositive NMOSD disease cases. NMOSD is an inflammatory condition of the central nervous system (CNS), mainly characterized by optic neuritis (ON) and transverse myelitis (TM). Autoantibodies against myelin oligodendrocyte glycoprotein (MOG-IgG) have been found in certain cases diagnosed as seronegative NMOSD (Fujihara, 2019).

As is evident from the above, various autoantigens may be employed in the CAAR approach described herein in order to target autoantibody-specific pathogenic B cells in neurological disease primarily targeting the central nervous system.

Chimeric Antigen Receptors and Chimeric Autoantibody Receptors:

According to the present invention, a chimeric antigen receptor (CAR) polypeptide comprises an extracellular antigen-binding domain, comprising an antibody or antibody fragment that binds a target antigen, a transmembrane domain, and an intracellular domain. CARs are typically described as comprising an extracellular ectodomain (antigen-binding domain) derived from an antibody and an endodomain comprising signaling modules derived from T cell signaling proteins. The CAAR of the present invention is based on a CAR structure but employs an autoantigen to direct the CAAR specificity. References to CAR constructs and common knowledge in the context of CAR constructs therefore apply to the present invention, if necessary.

In the present invention, the chimeric autoantibody receptors (CAAR) comprise an autoantigen in place of the extracellular antigen-binding domain of a CAR. This autoantigen may be referred to, without limitation, as a targeting domain, binding domain, or an extracellular autoantibody-binding domain, or as an extracellular ectodomain.

In a preferred embodiment, the ectodomain preferably comprises an autoantigen or fragments thereof bound by autoantibodies present in neurological autoimmune conditions primarily targeting the central immune system.

The autoantigen may be attached to a hinge region that provides flexibility and transduces signals through an anchoring transmembrane moiety to an intracellular signaling domain.

The transmembrane domains originate preferably from either CD8α or CD28. In the first generation of CARs the signaling domain consists of the zeta chain of the TCR complex. The term "generation" refers to the structure of the intracellular signaling domains. Second generation CARs are equipped with a single costimulatory domain originated from CD28 or 4-1BB. Third generation CARs already include two costimulatory domains, e.g. CD28, 4-1 BB, ICOS or OX40, CD3 zeta. The present invention preferably relates to a second or third generation "CAR" format, although the autoantibody-binding fragments described herein may be employed in any given CAR format.

In various embodiments, genetically engineered receptors that redirect cytotoxicity of immune effector cells toward B cells are provided.

These genetically engineered receptors are referred to herein as CAARs. CAARs are molecules that combine autoantigen-autoantibody specificity for a desired target (B-cell that secretes/presents pathogenic autoantibodies) with a T cell receptor-activating intracellular domain to generate a chimeric protein that exhibits a specific cellular immune activity. As used herein, the term "chimeric" describes being composed of parts of different proteins or DNAs from different origins.

The main characteristic of the CAARs described herein are their ability to redirect immune effector cell specificity, thereby triggering the proliferation of antigen-specific effector T cells, cytokine production (such as IFN-γ), and production of molecules that can mediate death of the target B cells expressing the target autoantibody.

Autoantigen Domain:

The present invention is partly based on the discovery that chimeric autoantibody receptors can be used to target autoantibodies that cause autoimmune disease. The invention includes compositions comprising at least one chimeric autoantibody receptor (CAAR) specific for an autoantibody, vectors comprising the same, compositions comprising CAAR vectors packaged in viral particles, and recombinant T cells or other effector cells comprising the CAAR. The invention also includes methods of making a genetically modified T cell expressing a CAAR (CAART) wherein the expressed CAAR comprises an autoantigen bound by an autoantibody present in a neurological autoimmune disease primarily targeting the central nervous system.

The "extracellular antigen-binding domain" or "extracellular binding domain" or "targeting domain" or "autoantigen" are used interchangeably and provide a CAAR with the ability to specifically bind to the target autoantibody of interest. The binding domain may be derived either from a natural, synthetic, semi-synthetic, or recombinant source. Multiple examples of the autoantigen domain are presented herein.

"Specific binding" is to be understood as via one skilled in the art, whereby the skilled person is clearly aware of various experimental procedures that can be used to test binding and binding specificity. Methods for determining equilibrium association or equilibrium dissociation constants are known in the art. Some cross-reaction or background binding may be inevitable in many protein-protein interactions; this is not to detract from the "specificity" of the binding between CAAR and autoantibody. "Specific binding" describes binding of an autoantigen to an autoantibody at greater binding affinity than background (unspecific) binding. The term "directed against" is also applicable when considering the term "specificity" in understanding the interaction between antibody and epitope.

An "antigen (Ag)" refers to a compound, composition, or substance that can stimulate the production of antibodies or a T cell response in an animal. An "epitope" refers to the region of an antigen to which an antibody binds. Epitopes can be formed both from contiguous amino acids or non-contiguous amino acids juxtaposed by tertiary folding of a protein.

By "autoantigen" is meant an endogenous antigen that stimulates production of an autoimmune response, such as production of autoantibodies. Autoantigen also includes a self-antigen or antigen from a normal tissue that is the target of a cell-mediated or an antibody-mediated immune response that may result in the development of an autoimmune disease.

"Autoantibody" refers to an antibody that is produced by a B cell specific for an autoantigen.

An illustrative example of the autoantigen component of the CAARs contemplated herein include but are not limited to the sequences set forth in SEQ ID NOs 2-4 and 10-12.

34

Antibodies and Antibody Fragments:

The CAAR of the present invention—in some embodiments—does not comprise an extracellular antigen-binding domain comprising an antibody or antibody fragment that binds a target polypeptide as described herein. The present CAAR construct is therefore distinct from common CAR constructs.

As used herein, an "antibody" generally refers to a protein consisting of one or more polypeptides substantially encoded by immunoglobulin genes or fragments of immunoglobulin genes. Where the term "antibody" is used, the term "antibody fragment" may also be considered to be referred to. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. The basic immunoglobulin (antibody) structural unit is known to comprise a tetramer or dimer. Each tetramer is composed of two identical pairs of polypeptide chains, each pair having one "light" (L) (about 25 kD) and one "heavy" (H) chain (about 50-70 kD). The N-terminus of each chain defines a variable region of about 100 to 110 or more amino acids, primarily responsible for antigen recognition. The terms "variable light chain" and "variable heavy chain" refer to these variable regions of the light and heavy chains respectively.

The CAARs of the invention are intended to bind against mammalian, in particular human, autoantibody targets. The use of protein names, for example defining the autoantigen of the CAAR construct, may correspond to either mouse or human versions of a protein.

Additional Components of the CAAR

In certain embodiments, the CAARs contemplated herein may comprise linker residues between the various domains, added for appropriate spacing and conformation of the molecule, for example a linker comprising an amino acid sequence that connects the extracellular and transmembrane domains, or fragments of an autoantigen. CAARs contemplated herein, may comprise one, two, three, four, or five or more linkers. In particular embodiments, the length of a linker is about 1 to about 25 amino acids, about 5 to about 20 amino acids, or about 10 to about 20 amino acids, or any intervening length of amino acids.

Illustrative examples of linkers include glycine polymers; glycine-serine polymers; glycine-alanine polymers; alanine-serine polymers; and other flexible linkers known in the art, such as the Whitlow linker. Glycine and glycine-serine polymers are relatively unstructured, and therefore may be able to serve as a neutral tether between domains of fusion proteins such as the CAARs described herein.

In particular embodiments, the binding domain of the CAAR is followed by one or more "linkers", "spacers" or "linker polypeptides" or "spacer polypeptides", which refers in some embodiments to a region that moves the autoantibody binding domain away from the effector cell surface to enable proper contact, antigen binding and immune cell activation. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region. In one embodiment, the spacer domain comprises the CH2 and CH3 domains of IgG1 or IgG4.

The extracellular binding domain of the CAAR may in some embodiments be followed by one or more "hinge domains," which play a role in positioning the binding domain away from the effector cell surface to enable proper cell/cell contact, antigen binding and activation. A CAAR may comprise one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region. Illustrative hinge domains suitable for use in the CAARs described herein include the hinge region derived from the extracellular regions of type 1 membrane proteins such as CD8 alpha, CD4, CD28, PD1, CD 152, and CD7, which may be wild-type hinge regions from these molecules or may be altered. In another embodiment, the hinge domain comprises a PD1, CD 152, or CD8 alpha hinge region.

The "transmembrane domain" is the portion of the CAAR that fuses the extracellular binding portion and intracellular signaling domain and anchors the CAAR to the plasma membrane of the immune effector cell.

The TM domain may be derived either from a natural, synthetic, semi-synthetic, or recombinant source. The TM domain may be derived from the alpha, beta or zeta chain of the T-cell receptor, CD3ε, CD3κ, CD4, CD5, CD8 alpha, CD9, CD 16, CD22, CD27, CD28, CD33, CD37, CD45, CD64, CD80, CD86, CD 134, CD 137, CD 152, CD 154, and PD1. In one embodiment, the CAARs contemplated herein comprise a TM domain derived from CD8 alpha or CD28.

In particular embodiments, CAARs contemplated herein comprise an intracellular signaling domain. An "intracellular signaling domain," refers to the part of a CAAR that participates in transducing the message of effective CAAR binding to a target autoantibody into the interior of the immune effector cell to elicit effector cell function, e.g., activation, cytokine production, proliferation and cytotoxic activity, including the release of cytotoxic factors to the CAAR-bound target, or other cellular responses elicited with antigen binding to the extracellular CAAR domain.

The term "effector function" refers to a specialized function of an immune effector cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function.

CAARs contemplated herein comprise one or more co-stimulatory signaling domains to enhance the efficacy, expansion and/or memory formation of T cells expressing CAAR receptors. As used herein, the term, "co-stimulatory signaling domain" refers to an intracellular signaling domain of a co-stimulatory molecule. Co-stimulatory molecules are cell surface molecules other than antigen receptors or Fc receptors that provide a second signal required for efficient activation and function of T lymphocytes upon binding to the target.

Polypeptides

"Peptide", "polypeptide", "polypeptide fragment" and "protein" are used interchangeably, unless specified to the contrary, and according to conventional meaning, i.e., as a sequence of amino acids. Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring.

In various embodiments, the CAAR polypeptides contemplated herein comprise a signal (or leader) sequence at the N-terminal end of the protein, which co-translationally or post-translationally directs transfer of the protein. Polypeptides can be prepared using any of a variety of well-known recombinant and/or synthetic techniques. Polypeptides contemplated herein specifically encompass the CAARs of the present disclosure, or sequences that have deletions from, additions to, and/or substitutions of one or more amino acid of a CAAR as disclosed herein.

An "isolated peptide" or an "isolated polypeptide" and the like, as used herein, refer to in vitro isolation and/or purification of a peptide or polypeptide molecule from a cellular environment, and from association with other components of the cell, i.e., it is not significantly associated with in vivo substances. Similarly, an "isolated cell" refers to a cell that has been obtained from an in vivo tissue or organ and is substantially free of extracellular matrix.

Nucleic Acids

As used herein, the terms "polynucleotide" or "nucleic acid molecule" refers to any nucleic acid molecule, for example DNA or RNA, such as messenger RNA (mRNA), RNA, genomic RNA (gRNA), plus strand RNA (RNA(+)), minus strand RNA (RNA(−)), genomic DNA (gDNA), complementary DNA (cDNA) or recombinant DNA. Polynucleotides include single and double stranded polynucleotides. Preferably, polynucleotides of the invention include polynucleotides or variants having at least about 50%, 55%, 60%, 65%, 70%, 75%, 80%, 85%, 90%, 95%, 96%, 97%, 98%, 99% or 100% sequence identity to any of the reference sequences described herein, typically where the variant maintains at least one biological activity of the reference sequence. In various illustrative embodiments, the present invention contemplates, in part, polynucleotides comprising expression vectors, viral vectors, and transfer plasmids, and compositions, and cells comprising the same.

Polynucleotides can be prepared, manipulated and/or expressed using any of a variety of well-established techniques known and available in the art. In order to express a desired polypeptide, a nucleotide sequence encoding the polypeptide, can be inserted into appropriate vector. Examples of vectors are plasmid, autonomously replicating sequences, and transposable elements. Additional exemplary vectors include, without limitation, plasmids, phagemids, cosmids, artificial chromosomes such as yeast artificial chromosome (YAC), bacterial artificial chromosome (BAC), or PI-derived artificial chromosome (PAC), bacteriophages such as lambda phage or MI 3 phage, and animal viruses. Examples of categories of animal viruses useful as vectors include, without limitation, retrovirus (including lentivirus), adenovirus, adeno-associated virus, herpesvirus {e.g., herpes simplex virus), poxvirus, baculovirus, papillomavirus, and papovavirus (e.g., SV40). Examples of expression vectors are pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, the coding sequences of the chimeric proteins disclosed herein can be ligated into such expression vectors for the expression of the chimeric protein in mammalian cells. The "control elements" or "regulatory sequences" present in an expression vector are those non-translated regions of the vector—origin of replication, selection cassettes, promoters, enhancers, translation initiation signals (Shine Dalgarno sequence or Kozak sequence) introns, a polyadenylation sequence, 5' and 3' untranslated regions—which interact with host cellular proteins to carry out transcription and translation. Such elements may vary in their strength and specificity. Depending on the vector system and host utilized, any number of suitable transcription and translation elements, including ubiquitous promoters and inducible promoters may be used.

Vectors

In particular embodiments, a cell (e.g., an immune effector cell, such as a T cell) is transduced with a retroviral vector, e.g., gamma-retroviral ora lentiviral vector, encoding a CAAR.

Retroviruses are a common tool for gene delivery. In particular embodiments, a retrovirus is used to deliver a polynucleotide encoding a CAAR to a cell. As used herein, the term "retrovirus" refers to an RNA virus that reverse transcribes its genomic RNA into a linear double-stranded DNA copy and subsequently covalently integrates its genomic DNA into a host genome. Once the virus is integrated into the host genome, it is referred to as a "provirus." The provirus serves as a template for RNA polymerase II and directs the expression of RNA molecules which encode the structural proteins and enzymes needed to produce new viral particles.

Illustrative retroviruses suitable for use in particular embodiments, include, but are not limited to: Moloney murine leukemia virus (M-MuLV), Moloney murine sarcoma virus (MoMSV), Harvey murine sarcoma virus (Ha-MuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are envisaged. In particular embodiments, a lentivirus is used to deliver a polynucleotide comprising a CAAR to a cell.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses.

As will be evident to one of skill in the art, the term "viral vector" is widely used to refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus.

In a preferred embodiment the invention therefore relates to a method for transfecting cells with an expression vector encoding a CAAR. For example, in some embodiments, the vector comprises additional sequences, such as sequences that facilitate expression of the CAAR, such a promoter, enhancer, poly-A signal or Woodchuck Hepatitis Virus (WHP) Posttranscriptional Regulatory Element (WPRE), and/or one or more introns. In preferred embodiments, the CAAR-coding sequence is flanked by transposon sequences, such that the presence of a transposase allows the coding sequence to integrate into the genome of the transfected cell.

In some embodiments, the genetically transformed cells are further transfected with a transposase that facilitates integration of a CAAR coding sequence into the genome of the transfected cells. In some embodiments the transposase is provided as DNA expression vector. However, in preferred embodiments, the transposase is provided as an expressible RNA or a protein such that long-term expression of the transposase does not occur in the transgenic cells. For example, in some embodiments, the transposase is provided as an mRNA (e.g., an mRNA comprising a cap and poly-A tail). Any transposase system may be used in accordance with the embodiments of the present invention. However, in some embodiments, the transposase is salmonid-type Tel-like transposase (SB). For example, the transposase can be the so called "Sleeping beauty" transposase, see e.g., U.S. Pat. No. 6,489,458, incorporated herein by reference. In some embodiments, the transposase is an engineered enzyme with increased enzymatic activity. Some specific examples of transposases include, without limitation, SB 10, SB 11 or SB 100X transposase (see, e.g., Mates et al, 2009, Nat Genet. 41(6):753-61, or U.S. Pat. No. 9,228,180, herein incorporated by reference). For example, a method can involve electroporation of cells with an mRNA encoding an SB 10, SB 11 or SB 100X transposase.

Transposable elements are natural, non-viral gene delivery vehicles capable of mediating stable genomic integration. The Sleeping Beauty (SB) transposon has the ability to cut-and-paste a nucleic acid sequence of interest into the genome, providing the basis for long-term, permanent transgene expression in transgenic cells and organisms, in this case for the transformation of immune cells, preferably T cells, with the CAAR-encoding nucleic acid sequences of the present invention. The SB transposon system is relatively well characterized and has been extensively engineered for efficient gene delivery and gene discovery purposes in a wide range of vertebrates, including humans. A skilled person is capable of identifying appropriate variants of the SB systema and incorporating these into the invention as is necessary. Specific, non-limiting, examples are provided below. The SB system is a safe and simple-to-use vector that enables cost-effective, rapid preparation of therapeutic doses of cell products.

Generally, a transposon system includes a transposon and a transposase. The transposon acts as a carrier, which carries the gene to be inserted into the genome. The transposase is the so-called "workhorse" of the system, catalyzing the process of transposition. The transposase is located between the inverted terminal repeats (ITRs) of the transposon.

Importantly, the transposase gene can be replaced with any nucleic acid sequence of interest, and the transposase can govern transposition events when encoded by a separate plasmid in trans. Physical separation of the transposon from the transposase enabled optimization of transposon versus transposase ratio, and also provided the freedom of supplying the transposase in the form of mRNA, instead of DNA. First, the transposase recognizes the transposon, and binds the ITRs. During synaptic complex formation, the transposon ends are brought together by transposase monomers (presumably forming a tetramer). The transposase generates a DNA double-strand break upon excision, while single-stranded gaps at the integration site. The pre-integration complex containing the transposon bound transposase performs the integration into the host genome. SB transposition is a highly coordinated reaction that efficiently filters out abnormal, toxic transposition intermediates (reviewed in Narayanavari & Izsvák, Cell & Gene Therapy insights, 2017).

Previous optimization of nucleotide residues (including mutations, deletions and additions) within the ITRs of the original SB transposon (pT) resulted in improved transposon versions, such as pT2, pT3, pT2B and pT4, which may be employed for the CAAR-encoding sequences described herein. In one embodiment, pT4 is employed.

Previous screening involving mutagenizing the primary amino acid sequence of the SB transposase has provided a number of hyperactive transposase versions. SB100X is 100-fold hyperactive compared to the originally resurrected transposase (SB10) in certain cell types. Currently available SB transposases include, but are not limited to, SB10, SB11 (3-fold higher activity than SB10), SB12 (4-fold higher than SB10), HSB1-HSB5 (up to 10-fold higher than SB10), HSB13-HSB17 (HSB17 is 17-fold higher than SB10), SB100X (100-fold higher than SB10), SB150X (130-fold higher than SB10). In one embodiment, SB100X is employed.

A further aspect of the invention relates to a genetically modified immune cell comprising a nucleic acid molecule or vector as described herein, and/or expressing a CAAR as described herein.

A further aspect of the invention relates to a vector comprising a nucleic acid molecule as described herein, preferably a viral vector, more preferably a gamma retroviral vector. In another aspect of the invention, the invention relates to a transposon vector, preferably a sleeping beauty vector, encoding and preferably capable of expressing the inventive CAAR.

In a preferred embodiment the immune cells intended for administering in treatment of the diseases mentioned herein are genetically modified with a nucleic acid as described herein, encoding and expressing the CAAR as described herein, using a "Sleeping beauty" transposon system, in particular a sleeping beauty transposase. The Sleeping Beauty transposon system is a synthetic DNA transposon designed to introduce precisely defined DNA sequences into the chromosomes of vertebrate animals, in the context of the present invention for the purposes of modifying immune cells to express the CAAR as described herein. The sleeping beauty transposons combine the advantages of viruses and naked DNA. Viruses have been evolutionarily selected based on their abilities to infect and replicate in new host cells. Simultaneously, cells have evolved major molecular defense mechanisms to protect themselves against viral infections. Avoiding the use of viruses is also important for social and regulatory reasons. The use of non-viral vectors such as the sleeping beauty system therefore avoids many, but not all, of the defenses that cells employ against vectors. For this reason, the sleeping beauty system enables particularly effective and safe genetic modification of the immune cells for administration to a patient.

Sequence Variants:

Sequence variants of the claimed nucleic acids, proteins, antibodies, antibody fragments and/or CAARs, for example those defined by % sequence identity, that maintain similar binding properties of the invention are also included in the scope of the invention. Such variants, which show alternative sequences, but maintain essentially the same binding properties, such as target specificity, as the specific sequences provided are known as functional analogues, or as functionally analogous. Sequence identity relates to the percentage of identical nucleotides or amino acids when carrying out a sequence alignment.

The recitation "sequence identity" as used herein refers to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

It will be appreciated by those of ordinary skill in the art that, as a result of the degeneracy of the genetic code, there are many nucleotide sequences that encode a polypeptide as described herein. Some of these polynucleotides bear minimal homology or sequence identity to the nucleotide sequence of any native gene. Nonetheless, polynucleotides that vary due to differences in codon usage are specifically contemplated by the present invention. Deletions, substitutions and other changes in sequence that fall under the described sequence identity are also encompassed in the invention.

Protein sequence modifications, which may occur through substitutions, are also included within the scope of the invention. Substitutions as defined herein are modifications made to the amino acid sequence of the protein, whereby one or more amino acids are replaced with the same number of (different) amino acids, producing a protein which contains a different amino acid sequence than the primary protein. Substitutions may be carried out that preferably do not significantly alter the function of the protein. Like additions, substitutions may be natural or artificial. It is well known in the art that amino acid substitutions may be made without significantly altering the protein's function. This is particularly true when the modification relates to a "conservative" amino acid substitution, which is the substitution of one amino acid for another of similar properties. Such "conserved" amino acids can be natural or synthetic amino acids which because of size, charge, polarity and conformation can be substituted without significantly affecting the structure and function of the protein. Frequently, many amino acids may be substituted by conservative amino acids without deleteriously affecting the protein's function.

In general, the non-polar amino acids Gly, Ala, Val, Ile and Leu; the non-polar aromatic amino acids Phe, Trp and Tyr; the neutral polar amino acids Ser, Thr, Cys, Gln, Asn and Met; the positively charged amino acids Lys, Arg and His; the negatively charged amino acids Asp and Glu, represent groups of conservative amino acids. This list is not exhaustive. For example, it is well known that Ala, Gly, Ser and sometimes Cys can substitute for each other even though they belong to different groups.

Substitution variants have at least one amino acid residue in the antibody molecule removed and a different residue inserted in its place. The sites of greatest interest for substitutional mutagenesis include the hypervariable regions, but FR alterations are also contemplated. If such substitutions result in a change in biological activity, then more substantial changes, denominated "exemplary substitutions" in the table immediately below, or as further described below in reference to amino acid classes, may be introduced and the products screened.

Potential amino acid substitutions:

| Original residue | Preferred conservative substitutions | Examples of exemplary substitutions |
|---|---|---|
| Ala (A) | Val | Val; Leu; Ile |
| Asg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn, Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Conservative amino acid substitutions are not limited to naturally occurring amino acids, but also include synthetic amino acids. Commonly used synthetic amino acids are omega amino acids of various chain lengths and cyclohexyl alanine which are neutral non-polar analogs; citrulline and methionine sulfoxide which are neutral non-polar analogs, phenylglycine which is an aromatic neutral analog; cysteic acid which is a negatively charged analog and ornithine which is a positively charged amino acid analog. Like the naturally occurring amino acids, this list is not exhaustive, but merely exemplary of the substitutions that are well known in the art.

Genetically Modified Cells and Immune Cells

The present invention contemplates, in particular embodiments, cells genetically modified to express the CAARs contemplated herein, for use in the treatment of B cell related conditions. As used herein, the term "genetically engineered" or "genetically modified" refers to the addition of extra genetic material in the form of DNA or RNA into the total genetic material in a cell. The terms, "genetically modified cells," "modified cells," and, "redirected cells," are used interchangeably.

An "immune cell" or "immune effector cell" is any cell of the immune system that has one or more effector functions (e.g., cytotoxic cell killing activity, secretion of cytokines, induction of ADCC and/or CDC).

Immune effector cells of the invention can be autologous/autogeneic ("self") or non-autologous ("non-self," e.g., allogeneic, syngeneic or xenogeneic). "Autologous", as used herein, refers to cells from the same subject, and represent a preferred embodiment of the invention. "Allogeneic", as used herein, refers to cells of the same species that differ genetically to the cell in comparison. "Syngeneic", as used herein, refers to cells of a different subject that are genetically identical to the cell in comparison. "Xenogeneic", as used herein, refers to cells of a different species to the cell in comparison. In preferred embodiments, the cells of the invention are autologous or allogeneic.

Illustrative immune effector cells used with the CAARs contemplated herein include T lymphocytes. The terms "T cell" or "T lymphocyte" are art-recognized and are intended to include thymocytes, immature T lymphocytes, mature T lymphocytes, resting T lymphocytes, cytokine-induced killer cells (CIK cells) or activated T lymphocytes. Cytokine-induced killer (CIK) cells are typically CD3- and CD56-positive, non-major histocompatibility complex (MHC)-restricted, natural killer (NK)-like T lymphocytes. A T cell can be a T helper (Th; CD4$^+$ T cell) cell, for example a T helper 1 (Th1) or a T helper 2 (Th2) cell. The T cell can be a cytotoxic T cell (CTL; CD8$^+$ T cell), CD4$^+$CD8$^+$ T cell, CD4 CD8 T cell, or any other subset of T cells. Other illustrative populations of T cells suitable for use in particular embodiments include naive T cells and memory T cells.

For example, when reintroduced back to patients after autologous cell transplantation, the T cells modified with the CAAR of the invention as described herein may recognize and kill tumor cells. CIK cells may have enhanced cytotoxic activity compared to other T cells, and therefore represent a preferred embodiment of an immune cell of the present invention.

As would be understood by the skilled person, other cells may also be used as immune effector cells with the CAARs as described herein. In particular, immune effector cells also include NK cells, NKT cells, neutrophils, and macrophages. Immune effector cells also include progenitors of effector cells wherein such progenitor cells can be induced to differentiate into an immune effector cells in vivo or in vitro.

The present invention provides methods for making the immune effector cells which express the CAAR contemplated herein. In one embodiment, the method comprises transfecting or transducing immune effector cells isolated from an individual such that the immune effector cells express one or more CAAR as described herein. In certain embodiments, the immune effector cells are isolated from an individual and genetically modified without further manipulation in vitro. Such cells can then be directly re-administered into the individual. In further embodiments, the immune effector cells are first activated and stimulated to proliferate in vitro prior to being genetically modified to express a CAAR. In this regard, the immune effector cells may be cultured before and/or after being genetically modified (i.e., transduced or transfected to express a CAAR contemplated herein).

In particular embodiments, prior to in vitro manipulation or genetic modification of the immune effector cells described herein, the source of cells is obtained from a subject. In particular embodiments, the CAAR-modified immune effector cells comprise T cells. T cells can be obtained from a number of sources including, but not limited to, peripheral blood mononuclear cells, bone marrow, lymph nodes tissue, cord blood, thymus issue, tissue from a site of infection, ascites, pleural effusion, spleen tissue, and tumors. In certain embodiments, T cells can be obtained from a unit of blood collected from a subject using any number of techniques known to the skilled person, such as sedimentation, e.g., FICOLL™ separation, antibody-conjugated bead-based methods such as MACS™ separation (Miltenyi). In one embodiment, cells from the circulating blood of an individual are obtained by apheresis. The apheresis product typically contains lymphocytes, including T cells, monocytes, granulocyte, B cells, other nucleated white blood cells, red blood cells, and platelets. In one embodiment, the cells collected by apheresis may be washed to remove the plasma fraction and to place the cells in an appropriate buffer or media for subsequent processing. The cells can be washed with PBS or with another suitable solution that lacks calcium, magnesium, and most, if not all other, divalent cations. As would be appreciated by those of ordinary skill in the art, a washing step may be accomplished by methods known to those in the art, such as by using a semiautomated flow through centrifuge. For example, the Cobe 2991 cell processor, the Baxter CytoMate, or the like. After washing, the cells may be resuspended in a variety of biocompatible buffers or other saline solution with or without buffer. In certain embodiments, the undesirable components of the apheresis sample may be removed in the cell directly resuspended culture media.

In certain embodiments, T cells are isolated from peripheral blood mononuclear cells (PBMCs) by lysing the red blood cells and depleting the monocytes, for example, by centrifugation through a PERCOLL™ gradient. A specific subpopulation of T cells can be further isolated by positive or negative selection techniques. One method for use herein is cell sorting and/or selection via negative magnetic immunoadherence or flow cytometry that uses a cocktail of monoclonal antibodies directed to cell surface markers present on the cells negatively selected.

PBMC may be directly genetically modified to express CAARs using methods contemplated herein. In certain embodiments, after isolation of PBMC, T lymphocytes are further isolated and in certain embodiments, both cytotoxic and helper T lymphocytes can be sorted into naive, memory, and effector T cell subpopulations either before or after genetic modification and/or expansion. CD8+ cells can be obtained by using standard methods. In some embodiments, CD8+ cells are further sorted into naive, central memory, and effector cells by identifying cell surface antigens that are associated with each of those types of CD8+ cells.

The immune effector cells, such as T cells, can be genetically modified following isolation using known methods, or the immune effector cells can be activated and expanded (or differentiated in the case of progenitors) in vitro prior to being genetically modified. In a particular embodiment, the immune effector cells, such as T cells, are genetically modified with the chimeric antigen receptors contemplated herein (e.g., transduced with a viral vector comprising a nucleic acid encoding a CAAR) and then are activated and expanded in vitro. In various embodiments, T cells can be activated and expanded before or after genetic modification to express a CAAR, using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

In a further embodiment, a mixture of, e.g., one, two, three, four, five or more, different expression vectors can be used in genetically modifying a donor population of immune effector cells wherein each vector encodes a different chimeric antigen receptor protein as contemplated herein. The resulting modified immune effector cells forms a mixed population of modified cells, with a proportion of the modified cells expressing more than one different CAAR proteins.

In one embodiment, the invention provides a method of storing genetically modified murine, human or humanized CAAR protein expressing immune effector cells which target an autoantibody, comprising cryopreserving the immune effector cells such that the cells remain viable upon thawing. A fraction of the immune effector cells expressing the CAAR proteins can be cryopreserved by methods known in the art to provide a permanent source of such cells for the future treatment of patients afflicted with the B cell related condition. When needed, the cryopreserved transformed immune effector cells can be thawed, grown and expanded for more such cells.

In one embodiment the immune cell is preferably selected from the group consisting of a T lymphocyte or an NK cell, more preferably cytotoxic T lymphocytes.

In a preferred embodiment the genetically modified immune cell comprising a nucleic acid molecule or vector as described herein, and/or expressing a CAAR as described herein, is characterised in that it is CD4+ and/or CD8+ T cell, preferably a mixture of CD4+ and CD8+ T cells. These T cell populations, and preferably the composition comprising both CD4+ and CD8+ transformed cells, show particularly effective cytolytic activity against various B cells, preferably against those cells and/or the associated medical conditions described herein.

In a preferred embodiment the genetically modified immune cells comprising a nucleic acid molecule or vector as described herein, and/or expressing a CAAR as described herein, are CD4+ and CD8+ T cells, preferably in a ration of 1:10 to 10:1, more preferably in a ratio of 5:1 to 1:5, 2:1 to 1:2 or 1:1. Administration of modified CAAR-T cells expressing the CAAR described herein at the ratios mentioned, preferably at a 1:1 CD4+/CD8+ ratio, lead to beneficial characteristics during treatment of the diseases mentioned herein, for example these ratios lead to improved therapeutic response and reduced toxicity.

Compositions and Formulations

The compositions contemplated herein may comprise one or more polypeptides, polynucleotides, vectors comprising said polynucleotides, genetically modified immune effector cells, etc., as contemplated herein. Compositions include but are not limited to pharmaceutical compositions.

A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions of the invention may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

In particular embodiments, compositions of the present invention comprise an amount of CAAR-expressing immune effector cells contemplated herein. As used herein, the term "amount" refers to "an amount effective" or "an effective amount" of a genetically modified therapeutic cell, e.g., T cell, to achieve a beneficial or desired prophylactic or therapeutic result, including clinical results.

A "prophylactically effective amount" refers to an amount of a genetically modified therapeutic cell effective to achieve the desired prophylactic result. Typically, but not necessarily, since a prophylactic dose is used in subjects prior to or at an earlier stage of disease, the prophylactically effective amount is less than the therapeutically effective amount. The term prophylactic does not necessarily refer to a complete prohibition or prevention of a particular medical disorder. The term prophylactic also refers to the reduction of risk of a certain medical disorder occurring or worsening in its symptoms.

A "therapeutically effective amount" of a genetically modified therapeutic cell may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects. The term "therapeutically effective amount" includes an amount that is effective to "treat" a subject (e.g., a patient). When a therapeutic amount is indicated, the precise amount of the compositions of the present invention to be administered can be determined by a physician with consideration of individual differences in age, weight, tumor size, extent of infection or metastasis, and condition of the patient (subject).

It can generally be stated that a pharmaceutical composition comprising the immune cells (T cells) described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mLs or less, even 250 mLs or 100 mLs or less. Hence the density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects of the present invention, particularly since all the infused cells will be redirected to a particular target antigen, lower numbers of cells may be administered. CAAR expressing cell compositions may be administered multiple times at dosages within these ranges. The cells may be allogeneic, syngeneic, xenogeneic, or autologous to the patient undergoing therapy.

Generally, compositions comprising the cells activated and expanded as described herein may be utilized in the treatment and prevention of diseases that arise in individuals who are immunocompromised. The CAAR-modified T cells of the present invention may be administered either alone, or as a pharmaceutical composition in combination with carriers, diluents, excipients, and/or with other components such as IL-2 or other cytokines or cell populations. In particular embodiments, pharmaceutical compositions contemplated herein comprise an amount of genetically modified T cells, in combination with one or more pharmaceutically or physiologically acceptable carriers, diluents or excipients.

Pharmaceutical compositions of the present invention comprising a CAAR-expressing immune effector cell population, such as T cells, may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for parenteral administration, e.g., intravascular (intravenous or intraarterial), intraperitoneal or intramuscular administration.

The liquid pharmaceutical compositions, whether they be solutions, suspensions or other like form, may include one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In a particular embodiment, compositions contemplated herein comprise an effective amount of CAAR-expressing immune effector cells, alone or in combination with one or more therapeutic agents. Thus, the CAAR-expressing immune effector cell compositions may be administered alone or in combination with other known treatments, such as other immunotherapies, etc. The compositions may also be administered in combination with antibiotics. Such therapeutic agents may be accepted in the art as a standard treatment for a particular disease state as described herein, such as a particular cancer. Exemplary therapeutic agents contemplated include cytokines, growth factors, steroids, NSAIDs, DMARDs, anti-inflammatories, chemotherapeutics, radiotherapeutics, therapeutic antibodies, or other active and ancillary agents.

Therapeutic Methods

As used herein, the terms "individual" and "subject" are often used interchangeably and refer to any animal that exhibits a symptom of a disease, disorder, or condition that can be treated with the gene therapy vectors, cell-based therapeutics, and methods disclosed elsewhere herein. In preferred embodiments, a subject includes any animal that exhibits symptoms of a disease, disorder, or condition of the hematopoietic system, e.g., an autoimmune disease, that can be treated with the cell-based therapeutics and methods disclosed herein. Suitable subjects include laboratory animals (such as mouse, rat, rabbit, or guinea pig), farm animals, and domestic animals or pets (such as a cat or dog). Non-human primates and, preferably, human patients, are included.

As used herein "treatment" or "treating" includes any beneficial or desirable effect on the symptoms or pathology of a disease or pathological condition, and may include even minimal reductions in one or more measurable markers of the disease or condition being treated. Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

As used herein, "prevent" and similar words such as "prevented", "preventing" or "prophylactic" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

The quantity and frequency of administration will be determined by such factors as the condition of the patient, and the type and severity of the patient's disease, although appropriate dosages may be determined by clinical trials.

The administration of the compositions contemplated herein may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

FIGURES

The invention is demonstrated by way of example by the following figures. The figures are to be considered as providing a further description of potentially preferred embodiments that enhance the support of one or more non-limiting embodiments of the invention.

SHORT DESCRIPTION OF THE FIGURES

Figure 1:
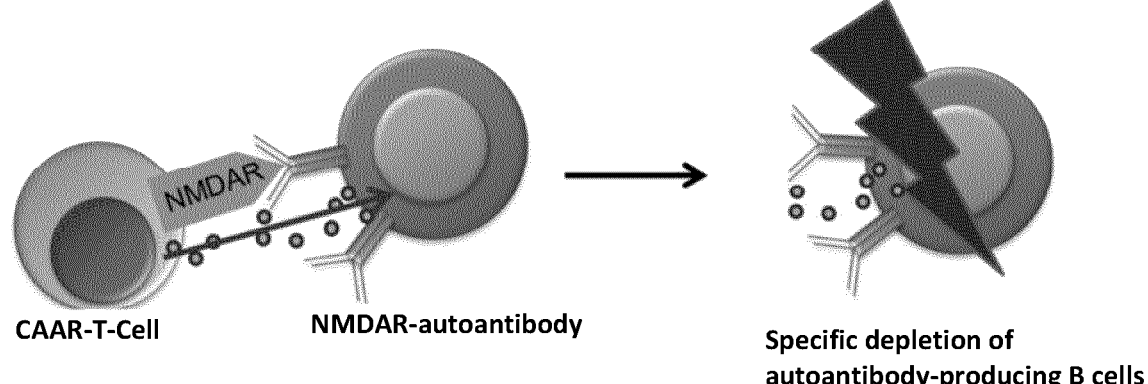
Figure 1:
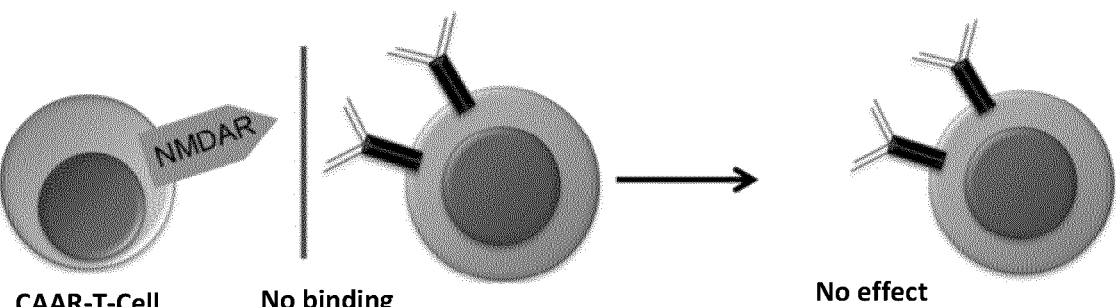

FIG. 1: Schematic outline of the inventive approach.

Figure 2:
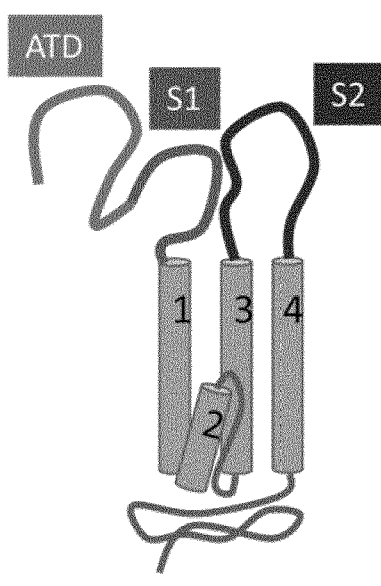
Figure 2:
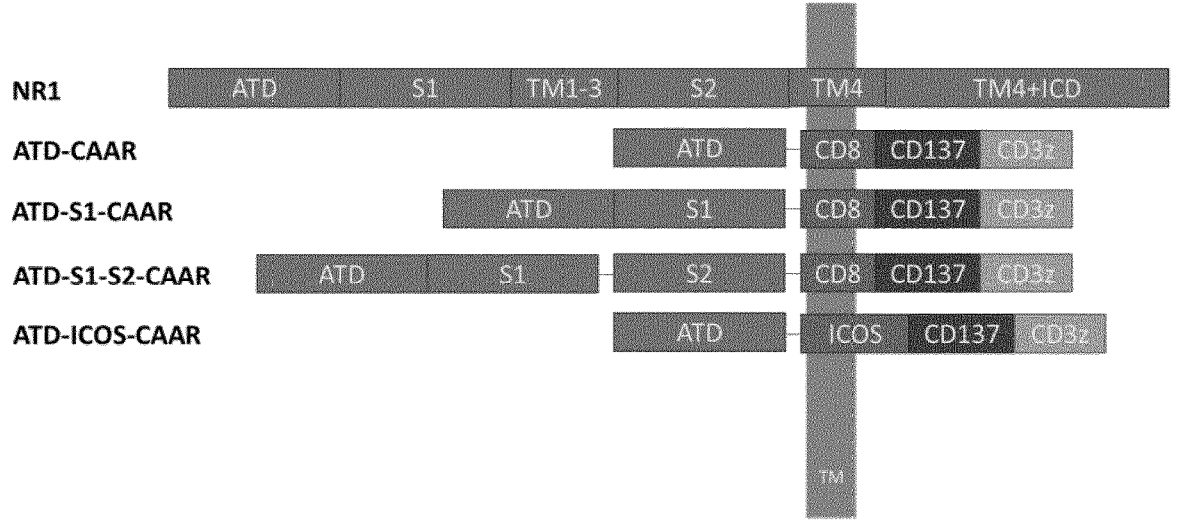

FIG. 2: Schematic representation of DMDA-receptor and corresponding CAAR constructs.

Figure 3:
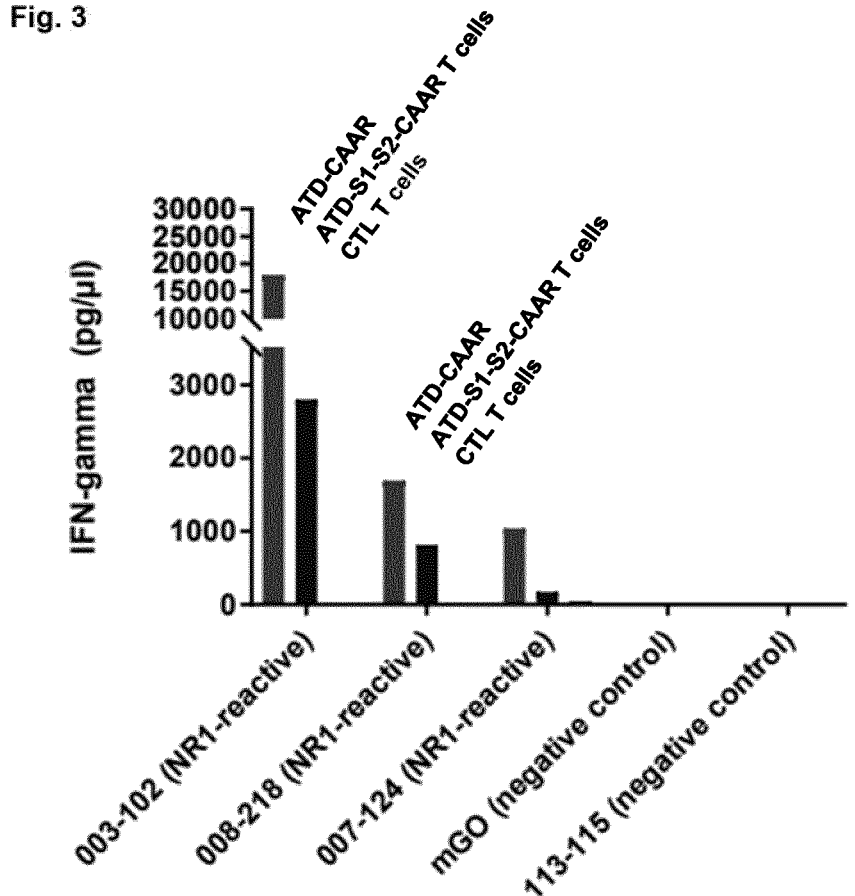

FIG. 3: Combination of NMDAR-antibodies and NMDAR-CAAR-T cells leads to release of interferon-γ.

Figure 4:
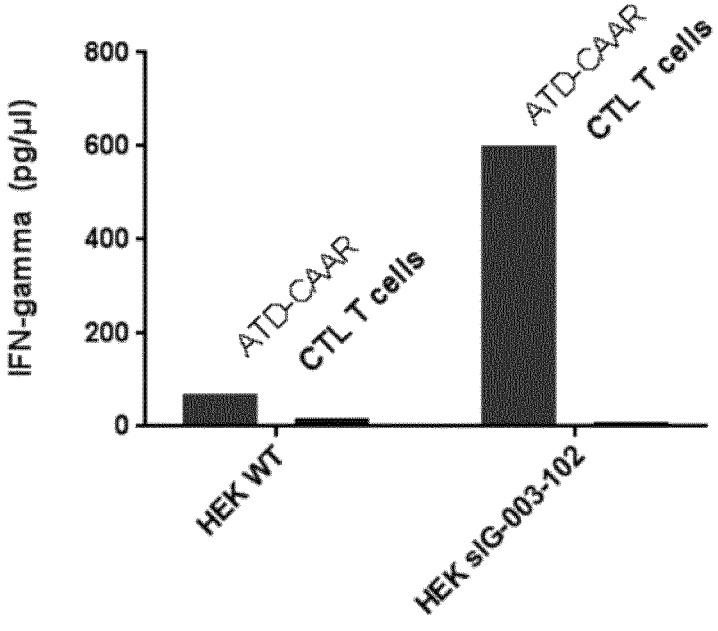
Figure 4:
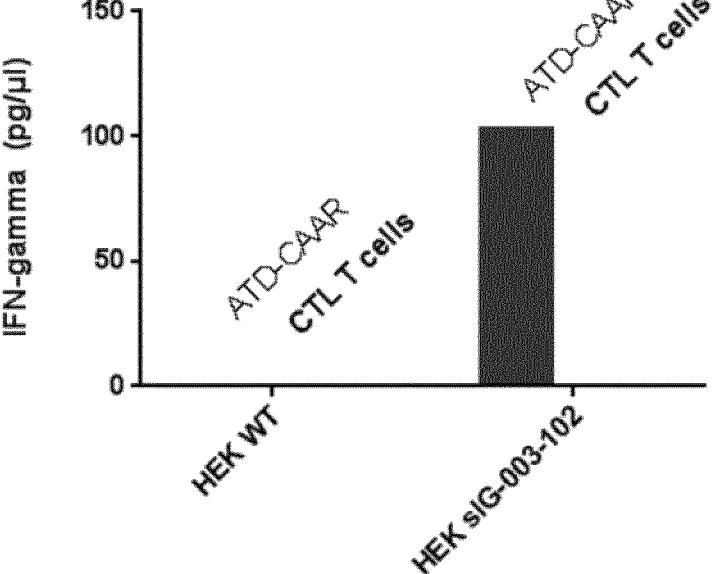

FIG. 4: Activation of CAAR-T cells by NMDAR NR1 antibodies presented on the surface of HEK cells.

Figure 5:
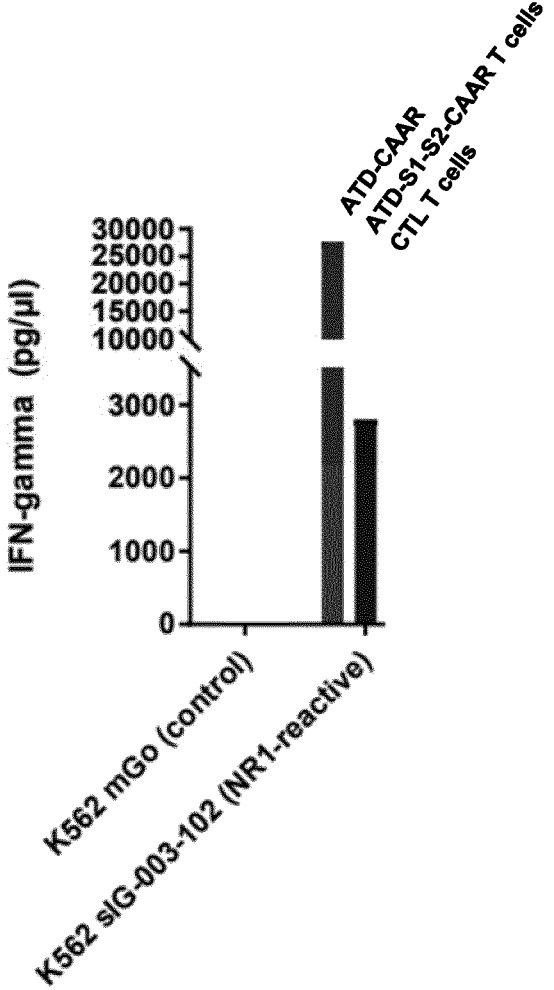

FIG. 5: Activation of CAAR-T cells by NMDAR NR1 antibodies presented on the surface of K562 cells.

Figure 6:
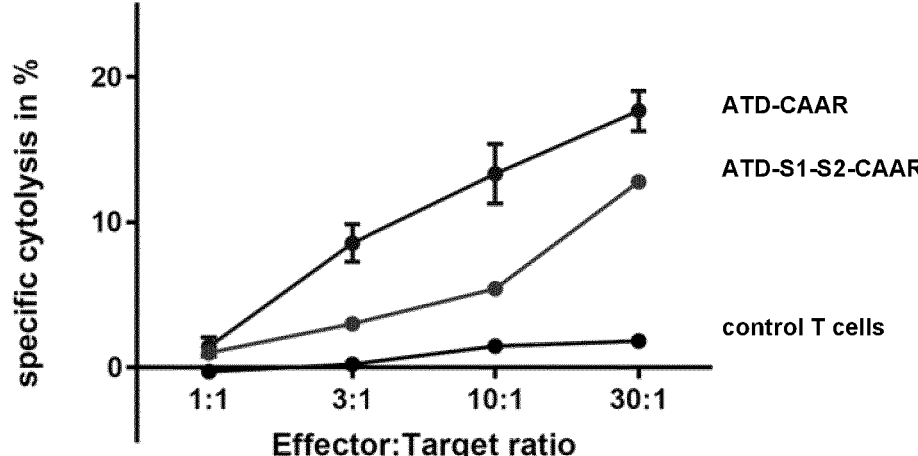

FIG. 6: Cell lysis of K562 cells expressing surface NR1-reactive antibodies by CAAR-T cells.

Figures 7, 8:
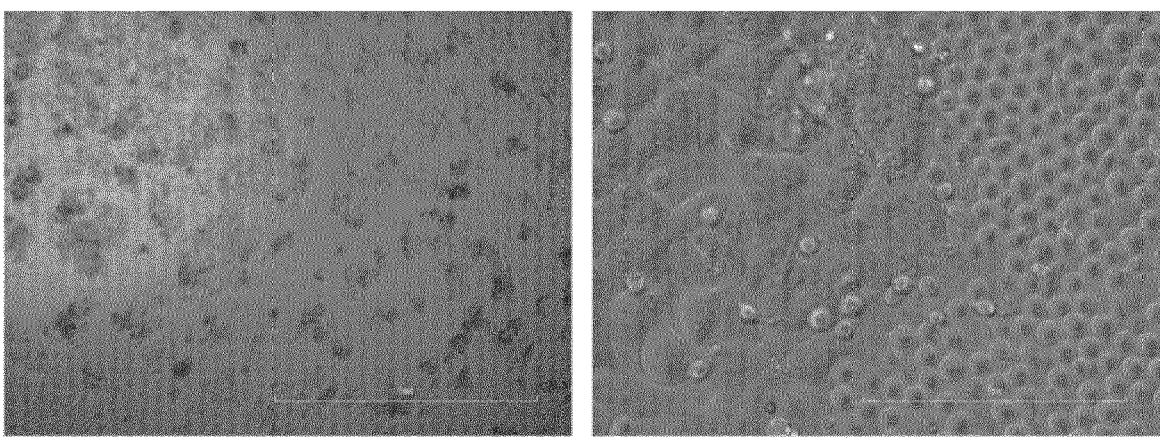

FIG. 7: Cytotoxicity of CAAR-T cells induced by NMDAR NR1 antibodies presented on the surface of HEK cells.

FIG. 8: Experimental plan of the in vivo approach to demonstrate therapeutic efficacy in an animal model.

Figure 9:
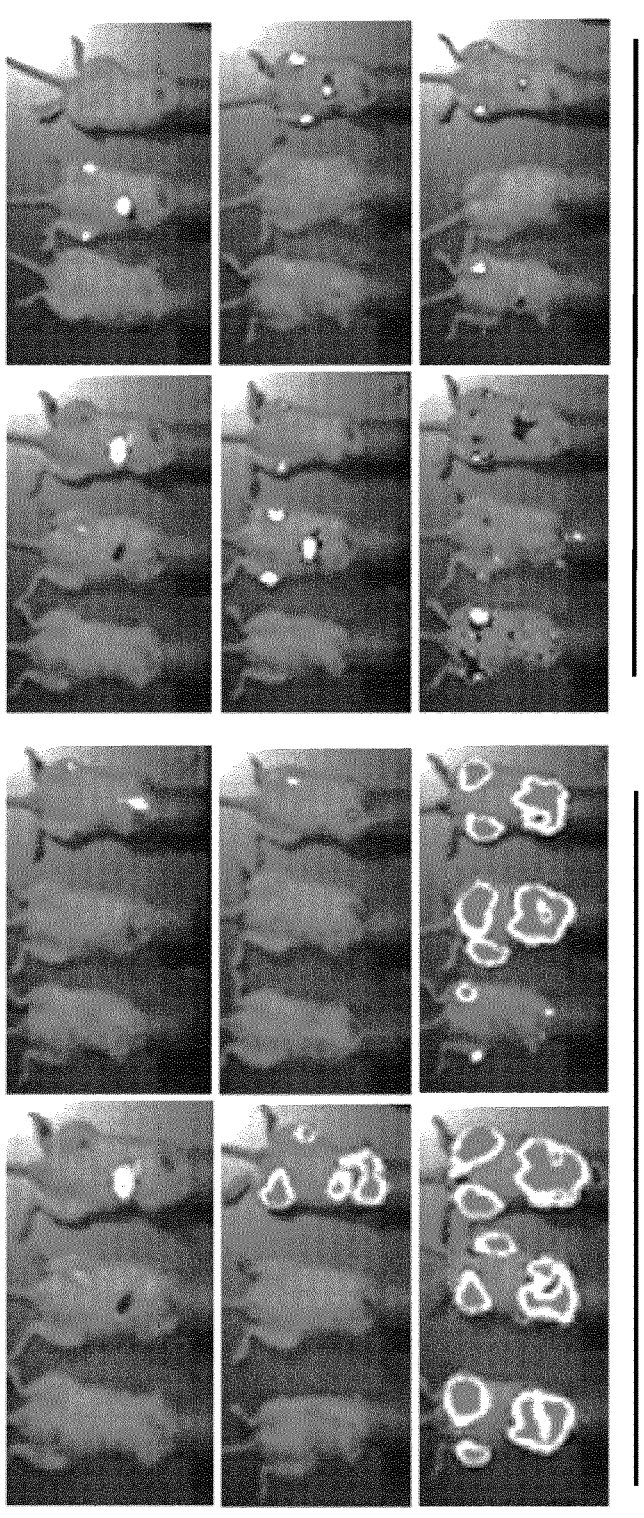

FIG. 9: NR1-CAAR-T cells show efficacy in an in-vivo model of NMDAR encephalitis FIG. 10: ATD-CAAR and ATD-S1-S2-T cells can be temporarily halted with Dasatinib.

FIG. 11: NR1-CAAR T cells maintain their functionality in the presence of soluble NR1-reactive antibodies.

DETAILED DESCRIPTION OF THE FIGURES

FIG. 1: Schematic Outline of the Inventive Approach.

A: CAAR-T cells expressing the CAAR construct of the invention, comprising as an autoantigen one or more NMDAR protein sequences, domains, fragments, or combinations thereof, recognize an autoantigen directed against the NMDAR presented on the surface of a B cell. This leads to specific depletion of said B cells through CAAR activation and the cytolytic capacity of the T cell. B: The CAAR-T cells of the present invention show no effect against B cells producing antibodies directed against other targets, thus enabling the present invention as exhibiting a specific effect against pathogenic autoantibody-producing B cells.

FIG. 2: Schematic Representation of DMDA-Receptor and Corresponding CAAR Constructs.

A: NMDA receptor structure is outlined, indicating the amino terminal domain, and subunits S1 and S2 of the NR1 domain. Transmembrane domains are represented as barrels 1-4. B: Overview of preferred but non-limiting NMDAR-CAAR constructs, indicating the domains of the NMDAR used to generate the antigen (targeting) portion of the CAAR.

FIG. 3: Combination of NMDAR-Antibodies and NMDAR-CAAR-T Cells Leads to Release of Interferon-γ.

Only in combination with NMDAR-antibodies (003-102, 008-218) do CAAR-T cells (left bars in the figure) show a strong release of interferon-γ. Significant amounts of interferon-γ are not detected in samples in which the ELISA plates have been coated with control antibodies (mGo, 113-115), or samples in which NMDAR-antibodies are incubated with control T cells (right bars in the figure). Cells were incubated for 48 h in the presence of the immobilized antibodies.

FIG. 4: Activation of CAAR-T Cells by NMDAR NR1 Antibodies Presented on the Surface of HEK Cells.

A strong activation of CAAR T-cells (left bars in the figure) is seen by the large release of interferon-γ in samples in which co-cultivation with the target HEK293 cells expressing NMDAR NR1 antibodies for 48 h (upper panel) or 24 h (lower panel) was carried out, but not with HEK wild-type cells or in combination with control T cells (right bars in the figure).

FIG. 5: Activation of CAAR-T Cells by NMDAR NR1 Antibodies Presented on the Surface of K562 Cells.

50,000 CAAR T-cells were co-cultured 1:1 with K562 cells expressing NR1-reactive or control antibodies on their surface for 48 hours. Activated ATD-CAAR and ATD-S1-S2 (but not control) T-cells massively released interferon-γ.

FIG. 6: Cell Lysis of K562 Cells Expressing Surface NR1-Reactive Antibodies by CAAR-T Cells.

For quantification of cell killing, target cells were incubated with CAAR T-cells at different Effector: Target (E:T) ratios ranging from 30:1 to 1:1 for 4 hours. Dead cells were stained by 7-AAD and analyzed by flow cytometry. T-cells from a healthy donor transduced with ATD-CAAR or ATD-S1-S2-CAAR resulted in dose-dependent killing of K562 cells expressing surface NR1-reactive antibodies.

FIG. 7: Cytotoxicity of CAAR-T Cells Induced by NMDAR NR1 Antibodies Presented on the Surface of HEK cells.

Co-cultivation of the antibody-presenting HEK cells with the NMDAR-CAAR-T cells led to extensive and early cell death as a result of CAAR-T cell activation (left panel). In contrast, control T cells led to no cytotoxicity (right panel).

FIG. 8: Experimental Plan of the In Vivo Approach to Demonstrate Therapeutic Efficacy in an Animal Model.

Nalm6 cells with surface-presentation of NR1 autoantibody and expressing a Luciferase enzyme (e.g. firefly-Luciferase) tagged with a fluorescent protein (e.g. GFP), are injected on day 1 into mice. On day 5, therapeutic CAAR-T cells expressing a CAAR of the present invention or control T cells without CAAR expression are injected. Bioluminescence imaging is conducted regularly, for example at time points 1, 5, 8, 12, 15, 19 and 22 days, to assess therapeutic effect against the Nalm6 cells.

FIG. 9: NR1-CAAR-T Cells Show Eefficacy in an In-Vivo Model of NMDAR Encephalitis As described in FIG. 8, Nalm6 cells with surface-presentation of NR1 autoantibody #003-102 and expressing a Luciferase enzyme (firefly-Luciferase, ffluc) tagged with a fluorescent protein (GFP, green fluorescent protein), are injected on day 1 into 18 mice. On day 5, therapeutic CAAR-T cells expressing a CAAR of the present invention or control T cells without CAAR expression are injected into 6 animals, per group. In vivo bioluminescence measurements on day 9 (4 days post-treatment) are depicted in the figure. White cloud/ring-like structures, filled with light grey, show tumor burden of Nalm6 cells. Detailed color-based delineation of tumor burden can be obtained via color images of the presented figures.

Figure 10:
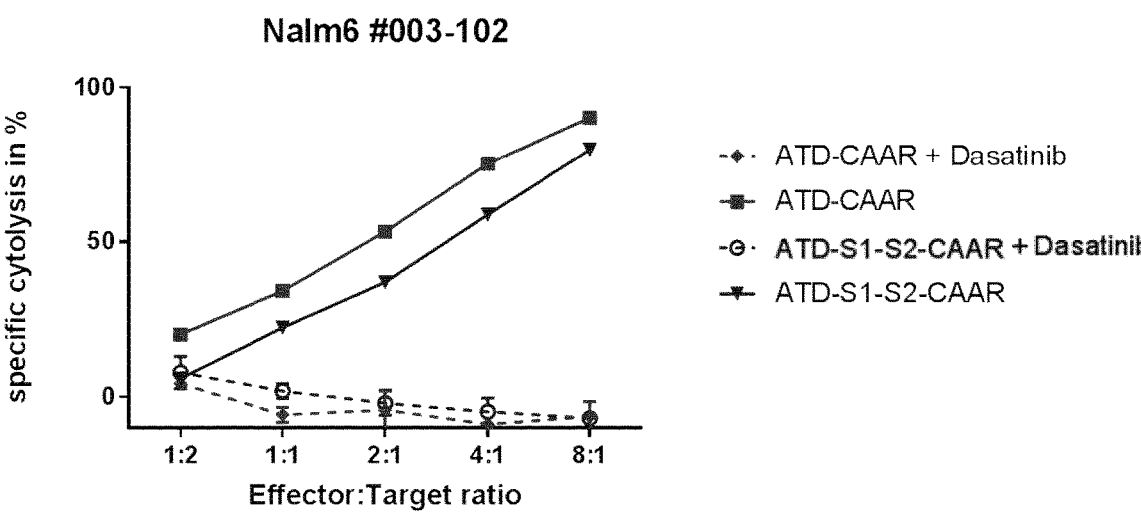

FIG. 10: ATD-CAAR and ATD-S1-S2-T Cells can be Temporarily Halted with Dasatinib Both ATD-CAAR and ATD-S1-S2-T cells can be temporarily halted using Dasatinib, a clinically approved Tyrosine Kinase inhibitor ("safety strategy"). T-cells from a healthy donor transduced with ATD-CAAR or ATD-S1-S2-CAAR resulted in dose-dependent killing of Nalm6 target cells expressing NR1-reactive antibody #003-102. For quantification of cell killing, Nalm6 target cells expressing NR1-reactive antibody #003-102 were incubated with CAAR T-cells at different Effector:Target (E:T) ratios ranging from 1:2 to 8:1 for 18 hours. Percentage of specific lysis was determined by reduction of bioluminescence in a Luciferase-assay.

FIG. 11: NR1-CAAR T Cells Maintain their Functionality in the Presence of Soluble NR1-Reactive Antibodies T-cells from a healthy donor transduced with ATD-CAAR show only a minor reduction (<20%) of killing efficiency when soluble NR1-reactive antibody #003-102 is present in cell culture medium. For quantification of cell killing, Nalm6 target cells expressing NR1-reactive antibody #003-102 were incubated with CAAR T-cells at different Effector: Target (E:T) ratios ranging from 1:16 to 1:1 for 18 hours. Percentage of specific lysis was determined by reduction of bioluminescence in a Luciferase-assay. Soluble antibody #003-102 was present throughout the whole experiment at three concentrations 0 μg/ml (control), 10 μg/μl and 50 μg/ml.

EXAMPLES

The invention is demonstrated by way of the examples disclosed below. The examples provide technical support for a more detailed description of potentially preferred, non-limiting embodiments of the invention.

Example 1: Generation of the NMDAR-CAAR Construct and Corresponding CAAR-T Cells A schematic outline of the inventive approach is demonstrated in FIG. 1.

In order to demonstrate a practical non-limiting embodiment of the invention, the inventors created several CAAR-T constructs (FIG. 2). These are based on the backbone of a CAR vector (FIG. 2B). Domains of the NMDA receptor have been positioned in the CAR vector in place of the customary antibody fragment typically contained in the CAR vector.

For this purpose, various combinations of the immune-relevant extracellular NMDA receptor domains were cloned into the CAR construct (FIG. 2A). As is demonstrated in FIG. 2A, the amino-terminal domain (ATD) and domains S1 and S2 of the NR1 subunit of the NMDA receptor were employed in place of the typical antigen binding antibody fragment of a CAR construct, thereby forming a chimeric autoantibody receptor (CAAR) construct, in which the NMDA receptor fragments serve to direct the CAAR-expressing T cell to B cells presenting autoantibodies directed against the NMDA receptor.

Specific preferred but non-limiting embodiments of the nucleotide sequences employed in generating the CAAR are presented above in the tables outlining the preferred sequences of the invention. The CAAR constructs employed in the following experimental validations are for example is outlined in SEQ ID Nos 30 and 28. These constructs comprise particularly immunogenic combinations of NMDA receptor fragments as the autoantigen, in other words the targeting portion of the CAAR.

This CAAR-T construct was lentivirally transduced into primary human T cells using the shuttle vector FUGW (Addgene # 14883) with transduction rates above 60% and expanded 10-20-fold over 8-12 days using established in vitro cultivation conditions.

The function of the CAAR-T cells was tested in three in vitro assays. In vitro evidence for the desired effect of the CAAR-T cells expressing the CAAR construct of the invention was collected by determining whether contact between the CAAR-T cell with a target anti-NMDAR antibody leads to activation of the CAAR-T cell, as evidenced by interferon γ measurement and cytotoxicity of the target cell.

Example 2: Activation of CAAR-T Cells by Clustered Anti-NMDAR NR1 Antibodies For this purpose, an ELISA plate was coated with human NMDAR antibodies and then incubated with CAAR-T cells or control T cells. Activation of CAAR-T cells results in release of Interferon-γ, which is measured in the supernatant. FIG. 3 shows that only in combination with NMDAR-antibodies (003-102, 008-218) and CAAR-T cells (left bars in the figure), a strong release of interferon-γ is evident. Significant amounts of interferon-γ are not detected in samples in which the ELISA plates have been coated with control antibodies (mGo, 113-115), or samples in which NMDAR-antibodies are incubated with control T cells (right bars in the figure).

Example 3: Activation of CAAR-T Cells by NMDAR NR1 Antibodies Presented on the Surface of HEK or K562 Cells For this purpose, the inventors employed a model of a NMDA receptor antibody-producing human cell that has been established previously. In this model, HEK293 cells express a human monoclonal NMDA receptor antibody localized in their cell membrane. The sequence of the human NMDA receptor antibody was identified previously (Kreye et al., 2016).

FIG. 4 shows that, similar to the assay described in Example 2, a strong activation of CAAR T-cells (left bars in the figure) is evident, corresponding to the large release of interferon-γ only seen in samples in which co-cultivation with the target cells for 48 h (upper panel) or 24 h (lower panel) was carried out, but not with HEK wild-type cells or in combination with control T cells (right bars in the figure).

FIG. 5 shows that co-culture for 48 hours of CAAR T-cells at a ratio of 1:1 with K562 cells expressing NR1-reactive or control antibodies on their surface leads to significant release of interferon gamma.

Example 4: Cytotoxicity of NR1 Antibody-Bearing HEK or K562 cells by CAAR-T Cells Target K562 cells were incubated with CAAR T-cells at different Effector:Target (E:T) ratios ranging from 30:1 to 1:1. T-cells from a healthy donor transduced with ATD-CAAR or ATD-S1-S2-CAAR resulted in dose-dependent killing of K562 cells expressing surface NR1-reactive antibodies. A quantitative representation of the data is provided in FIG. 6.

In order to test the cytotoxicity of the CAAR-T cells further, the inventors employed the HEK293 cells described in Example 3, in which the NMDA receptor antibodies are presented on their cell membrane. FIG. 7 shows that the co-cultivation of the antibody-presenting HEK cells with the NMDAR-CAAR-T cells led to extensive and early cell death as a result of CAAR-T cell activation (left panel). In contrast, control T cells led to no cytotoxicity (right panel).

Example 5: Human B-Cells from Patients with NMDA Receptor Encephalitis are Assessed Using the CAAR-T Cells Described Above In order to validate the cytotoxicity of the CAAR-T cells described above in a human model, human B-cells from patients with NMDA receptor encephalitis are to be incubated with the CAAR-T cells as described above. Co-incubation of the CAAR-T cells with the B cells obtained from patients with NMDA receptor encephalitis, leading to interaction between the autoantibodies against NMDAR autoantibodies that are presented by the patient B cells with the inventive CAAR-T cells, leading to CAAR-T cell activation and B cell death, will demonstrate the applicability of the invention in a disease-relevant pre-clinical in vitro setting.

Example 6: In Vivo Approach to Demonstrate Therapeutic Efficacy in an Animal Model In order to show therapeutic efficacy in an animal model in vivo, Nalm6 cells with surface-presentation of NR1 autoantibody #003-102 or #008-218 and expressing the Luciferase enzyme firefly-Luciferase (ffluc) tagged with a fluorescent protein (GFP, green fluorescent protein), were injected on day 1 into 16 mice. On day 5, therapeutic CAAR-T cells expressing a CAAR of the present invention or control T cells without CAAR expression were injected into 6 animals, per group. As a read-out of the assay, animal survival, target cell reduction (via in vivo bioluminescence measurements) and serum antibody levels are determined. The experimental setup follows in principle the methods disclosed in Ellebrecht et al (2016). Refer to FIG. 8 for a schematic representation of the experimental setup.

The potential readouts for the assay relate to bioluminescence imaging quantification (for the detection of in vivo killing), quantification of anti-NR1 serum levels by ELISA (for the detection of reduction of circulating antibodies), and postmortem analysis of treated animals (in order to determine off-target toxicity).

Information can also be obtained via examination by flow cytometry, in order to determine the expansion of the CAAR-T cells, and histological analysis of lymphatic organs, the brain or other organs, in order to determine whether off-target effects are evident. Low off-target effects (via histological analysis) and significant target cell killing (evidenced by reduced bioluminescence) will demonstrate the applicability of the invention in a disease-relevant pre-clinical in vivo setting.

Preliminary data has been obtained via bioluminescence imaging of Nalm6 cells with surface-presentation of an NR1 autoantibody #003-102 and expressing a Luciferase enzyme (firefly-Luciferase, ffluc) tagged with a fluorescent protein (GFP, green fluorescent protein), according to the scheme presented above. In vivo bioluminescence measurements on day 9 (4 days post-treatment), as depicted in FIG. 9, show a drastic reduction of Nalm6 burden in 6/6 of animals treated with ATD-CAAR, and 5/6 animals treated with ATD-S1-S2-CAAR, as compared to 0/6 animals in the control group. These data show that NR1-CAAR-T cells kill their target cells also in an in-vivo setting.

Example 7: ATD-CAAR and ATD-S1-S2-T Cells can be Temporarily Halted Using Dasatinib Both ATD-CAAR and ATD-S1-S2-T cells can be temporarily halted using Dasatinib, a clinically approved Tyrosine Kinase inhibitor ("safety strategy"). Addition of 100 nM Dasatinib completely abolished killing of target cells in the assay performed. Results are depicted in FIG. 10.

T-cells from a healthy donor transduced with ATD-CAAR or ATD-S1-S2-CAAR resulted in dose-dependent killing of Nalm6 target cells expressing NR1-reactive antibody #003-102. For quantification of cell killing, Nalm6 target cells expressing NR1-reactive antibody #003-102 were incubated with CAAR T-cells at different Effector:Target (E:T) ratios ranging from 1:2 to 8:1 for 18 hours. Percentage of specific lysis was determined by reduction of bioluminescence in a Luciferase-assay.

This data demonstrates that NR1-CAAR T cells can temporarily be inactivated using the drug Dasatinib to help reduce acute toxicity, allowing the T cells to recover their cytotoxic effects after the drug is withdrawn.

Example 8: NR1-CAAR T Cells Maintain their Functionality in the Ppresence of Soluble NR1-Reactive Antibodies T-cells from a healthy donor transduced with ATD-CAAR show only a minor reduction (<20%) of killing efficiency when soluble NR1-reactive antibody #003-102 is present in cell culture medium. The presence of soluble NR1-reactive antibody mirrors the in vivo situation in patients, where pathogenic NR1-reactive antibodies could potentially interfere with killing of NR1-CAAR-T-cell mediated target cell lysis through binding to the CAAR constructs.

In this experiment, for quantification of cell killing, Nalm6 target cells expressing NR1-reactive antibody #003-102 were incubated with CAAR T-cells at different Effector:Target (E:T) ratios ranging from 1:16 to 1:1 for 18 hours. Percentage of specific lysis was determined by reduction of bioluminescence in a Luciferase-assay. Soluble antibody #003-102 was present throughout the whole experiment at three concentrations 0 μg/ml (control), 10 μg/μl and 50 μg/ml. Results are depicted in FIG. 11.

This data demonstrates that NR1-CAAR-T cells maintain their function in a situation similar to that found in patients, i.e. when soluble NR1-reactive antibodies are present and potentially in competition as a binding target of the inventive CAAR-T cells. In particular, no relevant reduction of NR1-CAAR-T cell function was observed when 50 μg/μl of high-affinity NR1-antibody #003-102 was added, which is likely a level of soluble NR1-reactive antibodies that is greater than found in patients. This property could not have been expected or derived from the prior art.

REFERENCES

Dalmau et al. Lancet Neurol. 2011; 10:63-74.
Ellebrecht et al. Science 2016; 353(6295):179-84.
Kreye et al. Brain. 2016; 139:2641-2652.
Prüss, H. Neurotransmitter 2017; 28, 34-41.
Titulaer et al. Lancet Neurol. 2013; 12:157-165.
Zong et al. Front Immunol. 2017; 8: 752.
Dalmau et al. 2008; 7:1091-1098.
Prüss et al. 2010. Neurology. 75(19):1735-9.
Doss et al. 2014. Ann Clin Transl Neurol. 1(10):822-32.
Prüss et al. 2013. Neurology. 78(22):1743-53.
Lapteva et al. Arthritis Rheum (2006) 54(8):2505-14.
Lai et al. Ann Neurol (2009) 65(4):424-34.
Montagna et al (2018) Front. Neurol. 9:329.
Lancaster et al, Neurology 77, 2011, 1701.
dos Passos et al. 2018, Front. Neurol. 9:217.
Fox-Edmiston et al. 2015 CNS Drugs, 29(9): 715-724.
Fujihara, 2019, Curr Opin Neurol. Jun; 32(3):385-394.
Narayanavari & Izsvák, Cell & Gene Therapy insights, 2017; 3(2), 131-158.
Fransson et al. J. of Neuroinflammation, vol. 9, no. 1, 2012, 112
Ryan et al, Advanced Drug Delivery Reviews, Vol. 114, 2017, 240-255
Chatenoud, Nature Biotechnology, Vol. 34, No. 9, 2016, 930-932
Tahir, Cureus, 2018 XP055647054, ISSN: 2168-8184
Ludwig et al, Frontiers In Immunology, Vol. 8, 2017, XP055420435
Kreye et al, Brain, Vol. 139, No. 10, 2016, 2641-2652
McKee et al, Rare Disease Review, 2017, XP055647052

The invention claimed is:

1. A nucleic acid molecule encoding a chimeric autoantibody receptor (CAAR), the nucleic acid molecule comprising:
   i. a sequence encoding an autoantigen comprising an amino-terminal domain (ATD) of an NMDA receptor according to SEQ ID NO 14, or a fragment thereof that is bound by autoantibodies in anti-N-methyl-D-aspartate receptor encephalitis (anti-NMDAR encephalitis),
   ii. a sequence encoding a transmembrane domain, and
   iii. a sequence encoding an intracellular signaling domain.

2. The nucleic acid molecule according to claim 1:
   wherein the transmembrane domain is a CD8 alpha transmembrane domain;
   wherein the intracellular domain comprises a CD137 (4-1BB) co-stimulatory domain;
   wherein the intracellular domain comprises a CD3 zeta chain signaling domain; and
   wherein the nucleic acid molecule comprises additionally one or more sequences encoding one or more leader, linker and/or spacer polypeptides positioned between the autoantigen and transmembrane domain and/or N-terminally of and/or between fragments of the autoantigen, and/or between the transmembrane and intracellular co-stimulatory domain.

3. The nucleic acid molecule encoding a chimeric autoantibody receptor (CAAR) according to claim 1, comprising:
   i. a sequence encoding a leader polypeptide, wherein the leader polypeptide is a CD8 leader polypeptide;
   ii. a sequence encoding an autoantigen according to claim 1;
   iii. optionally a sequence encoding a linker polypeptide positioned between one or more NMDAR fragments;
   iv. optionally a sequence encoding a linker polypeptide positioned between the autoantigen and transmembrane domain;
   V. a sequence encoding a CD8 alpha transmembrane domain;
   vi. optionally a sequence encoding a linker polypeptide positioned between a transmembrane domain and an intracellular signaling domain; and
   vii. a sequence encoding an intracellular signaling domain, said intracellular signaling domain comprising a CD137 (4-1BB) co-stimulatory domain and a CD3 zeta chain signaling domain, wherein optionally a linker sequence is positioned between the co-stimulatory and signaling domains.

4. The nucleic acid molecule encoding a chimeric autoantibody receptor (CAAR) according to claim 1, further comprising one or more of:
   a sequence encoding a leader polypeptide, wherein the leader polypeptide is a CD8 leader polypeptide, said sequence comprising a sequence according to SEQ ID NO 1;
   a sequence encoding an autoantigen according to claim 1, said sequence comprising a sequence according to SEQ ID NO 3 (ATD);
   a sequence encoding a linker polypeptide positioned between one or more NMDAR fragments, said sequence comprising a sequence according to GGCACC (linker-1);
   a sequence encoding a linker polypeptide positioned between the autoantigen and transmembrane domain, said sequence comprising a sequence according to SEQ ID NO 7 (linker-2) or SEQ ID NO 32 (linker-2b);
   a sequence encoding a CD8 alpha transmembrane domain according to SEQ ID NO 8;
   a sequence encoding a linker polypeptide positioned between a transmembrane domain and an intracellular signaling domain, said sequence comprising a sequence according to GGCAGC (linker-3); and
   a sequence encoding an intracellular signaling domain, said intracellular signaling domain comprising a CD137 (4-1BB) co-stimulatory domain and a CD3 zeta chain signaling domain, said sequence comprising a sequence according to SEQ ID NO 10 (CD137) and SEQ ID NO 11 (CD3z), respectively, wherein optionally a linker sequence is positioned between the co-stimulatory and signaling domains.

5. The nucleic acid molecule encoding a chimeric autoantibody receptor (CAAR) according to claim 1, wherein the autoantigen encoded by the nucleic acid sequence comprises one or more fragments of a NR1 and/or NR2 subunit of a NMDA receptor and not a complete NR1 and/or NR2 subunit.

6. The nucleic acid molecule according to claim 1, wherein the autoantigen comprises an amino-terminal domain (ATD) of an NMDA receptor according to SEQ ID NO 14.

7. The nucleic acid molecule according to claim 6, wherein the transmembrane domain is a CD8 alpha transmembrane domain; and wherein the intracellular domain comprises a CD137 (4-1BB) co-stimulatory domain and a CD3 zeta chain signaling domain.

8. The nucleic acid molecule according to claim 7, wherein the transmembrane domain is a CD8 alpha transmembrane domain according to SEQ ID NO 20; and wherein the intracellular domain comprises a CD137 (4-1BB) co-stimulatory domain according to SEQ ID NO 22 and a CD3 zeta chain signaling domain according to SEQ ID NO 23.

9. The nucleic acid molecule according to claim 1, wherein the transmembrane domain and the intracellular domain comprise an ICOS transmembrane domain and ICOS intracellular domain according to SEQ ID NO 21.

10. A vector comprising a nucleic acid molecule encoding a chimeric autoantibody receptor (CAAR) according to claim 1.

11. A vector according to claim 10, wherein the vector is a viral vector, nanoparticles as a transfection vehicle, a transposon or an RNA vector.

\* \* \* \* \*

SEQUENCE LISTING

```
<160> NUMBER OF SEQ ID NOS: 32

<210> SEQ ID NO 1
<211> LENGTH: 63
<212> TYPE: DNA
<213> ORGANISM: Artificial Sequence
<220> FEATURE:
<223> OTHER INFORMATION: CAAR component sequence

<400> SEQUENCE: 1
atggctctgc ctgtgacagc tctgctgctg cctctggccc tgctgctgca tgctgccaga      60
cct                                                                     63

<210> SEQ ID NO 2
<211> LENGTH: 54
<212> TYPE: DNA
<213> ORGANISM: Artificial Sequence
<220> FEATURE:
<223> OTHER INFORMATION: CAAR component
```

-continued

```
<400> SEQUENCE: 2
atgtctacaa tgagactgct gacactggcc ctgctgttca gctgttctgt ggcc          54

<210> SEQ ID NO 3
<211> LENGTH: 1125
<212> TYPE: DNA
<213> ORGANISM: Homo sapiens

<400> SEQUENCE: 3
agagccgcct gcgatcccaa gatcgtgaat atcggagccg tgctgagcac ccggaagcac     60
gagcagatgt tcagagaagc cgtgaaccag gccaacaaga gacacggcag ctggaagatc    120
cagctgaacg ccacaagcgt gacccacaag cctaacgcca ttcagatggc cctgagcgtg    180
tgcgaggatc tgatcagctc tcaggtgtac gccatcctgg tgtctcaccc tccaacacct    240
aacgaccact tcacccctac acctgtgtct tacaccgccg gcttctacag aatccctgtg    300
ctgggcctga ccaccagaat gagcatctac agcgacaaga gcatccacct gagctttctg    360
cggaccgtgc ctccttacag ccaccagtct agcgtttggt tcgagatgat gcgggtgtac    420
agctggaacc acatcatcct gctggtgtcc gacgaccacg aaggcagagc cgctcagaag    480
agactggaaa ccctgctgga agagagagag tccaaggccg agaaggtgct gcagttcgat    540
cccggcacca agaacgtgac agccctgctg atggaagcca agaactgga agccagagtg     600 atcatcctga gcgcctccga agatgatgcc gccaccgtgt atagagccgc cgctatgctg    660
aatatgaccg gcagcggata cgtgtggctc gtgggcgaga gagagattag cggaaacgcc    720
ctgagatacg cccctgatgg aatcctggga ctgcagctga tcaacggcaa gaacgagagc    780
gcccacatct ctgatgccgt gggagttgtg gctcaggccg tgcatgagct gctggaaaaa    840
gagaacatca ccgatcctcc acggggctgc gtgggcaaca ccaacatctg gaaaacaggc    900
ccactgttca gcgggtgct gatgagcagc aaatacgccg atggcgtgac aggccgggtc      960
gagtttaatg aggacggcga cagaaagttc gccaactaca gcatcatgaa cctgcagaac   1020
cggaagctgg tgcaagtggg catctacaac ggcacccacg tgatccccaa cgaccggaag   1080
attatctggc ctggcggcga aaccgagaag cccagaggct accag                   1125

<210> SEQ ID NO 4
<211> LENGTH: 453
<212> TYPE: DNA
<213> ORGANISM: Homo sapiens

<400> SEQUENCE: 4
atgagcacca gactgaagat tgtgaccatc caccaagagc ctttcgtgta cgtgaagccc      60
acactgagcg acggcacctg taaagaagag ttcaccgtca acggcgaccc tgtgaagaaa    120
gtgatctgca caggccccaa cgatacaagc cctggcagcc ctagacacac cgttcctcag    180
tgctgctacg gcttctgcat cgacctgctg atcaagctgg cccggaccat gaacttcacc    240
tacgaagtgc acctggtggc cgacggcaag tttggcacac aagagagagt gaacaacagc    300
aacaagaaag aatggaacgg catgatgggc gagctgctgt ctggacaggc cgacatgatt    360
gtggcccctc tgaccatcaa caacgagcgg gcccagtaca tcgagttcag caagccattc    420
aagtaccagg gcctgacaat cctggtcaag aaa                                 453

<210> SEQ ID NO 5
<211> LENGTH: 414
<212> TYPE: DNA
<213> ORGANISM: Homo sapiens
```

-continued

```
<400> SEQUENCE: 5
cggatcaccg gcatcaacga ccccagactg agaaatccct ccgacaagtt catctacgcc        60
acagtgaagc agagcagcgt ggacatctac ttcagacgcc aggtggaact gagcaccatg       120
tacagacaca tggaaaagca caactacgag tctgccgccg aggcaatcca ggccgtcaga       180
gataacaagc tgcacgcctt catctgggac agcgccgtgc tggaatttga ggccagccag       240
aagtgcgatc tggtcaccac cggtgaactg tttttcagaa gcggctttgg catcggcatg       300
cggaaggact ctccctggaa gcagaatgtg tccctgagca tcctgaagtc tcacgagaac       360
ggcttcatgg aagatctgga caagacctgg gtccgatacc aagagtgcga tagc            414

<210> SEQ ID NO 6
<211> LENGTH: 3245
<212> TYPE: DNA
<213> ORGANISM: Homo sapiens

<400> SEQUENCE: 6
gcccgcggcc cgagcccatg agcaccatgc gcctgctgac gctcgccctg ctgttctcct        60
gctccgtcgc ccgtgccgcg tgcgacccca agatcgtcaa cattggcgcg gtgctgagca       120
cgcggaagca cgagcagatg ttccgcgagg ccgtgaacca ggccaacaag cggcacggct       180
cctggaagat tcagctcaat gccacctccg tcacgcacaa gcccaacgcc atccagatgg       240
ctctgtcggt gtgcgaggac ctcatctcca gccaggtcta cgccatccta gttagccatc       300
cacctacccc caacgaccac ttcactccca cccctgtctc ctacacagcc ggcttctacc       360
gcatacccgt gctggggctg accacccgca tgtccatcta ctcggacaag agcatccacc       420
tgagcttcct gcgcaccgtg ccgccctact cccaccagtc cagcgtgtgg tttgagatga       480
tgcgtgtcta cagctggaac cacatcatcc tgctggtcag cgacgaccac gagggccggg       540
cggctcagaa acgcctggag acgctgctgg aggagcgtga gtccaaggca gagaaggtgc       600
tgcagtttga cccagggacc aagaacgtga cggccctgct gatggaggcg aaagagctgg       660
aggcccgggt catcatcctt tctgccagcg aggacgatgc tgccactgta taccgcgcag       720
ccgcgatgct gaacatgacg ggctccgggt acgtgtggct ggtcggcgag cgcgagatct       780
cggggaacgc cctgcgctac gcccccggacg gcatcctcgg gctgcagctc atcaacggca       840
agaacgagtc ggcccacatc agcgacgccg taggcgtggt ggcccaggcc gtgcacgagc       900
tcctcgagaa ggagaacatc accgacccgc gcgggggctg cgtgggcaac accaacatct       960
ggaagaccgg gccgctcttc aagagagtgc tgatgtcttc caagtatgcg gatggggtga      1020
ctggtcgcgt ggagttcaat gaggatgggg accggaagtt cgccaactac agcatcatga      1080
acctgcagaa ccgcaagctg gtgcaagtgg gcatctacaa tggcacccac gtcatcccta      1140
atgacaggaa gatcatctgg ccaggcggag agacagagaa gcctcgaggg taccagatgt      1200
ccaccagact gaagattgtg acgatccacc aggagccctt cgtgtacgtc aagcccacgc      1260
tgagtgatgg gacatgcaag gaggagttca cagtcaacgg cgacccagtc aagaaggtga      1320
tctgcaccgg gcccaacgac acgtcgccgg gcagcccccg ccacacggtg cctcagtgtt      1380
gctacggctt ttgcatcgac ctgctcatca agctggcacg gaccatgaac ttcacctacg      1440
aggtgcacct ggtggcagat ggcaagttcg gcacacagga gcgggtgaac aacagcaaca      1500
agaaggagtg gaatgggatg atgggcgagc tgctcagcgg gcaggcagac atgatcgtgg      1560
cgccgctaac cataaacaac gagcgcgcgc agtacatcga gttttccaag cccttcaagt      1620
```

-continued

```
accagggcct gactattctg gtcaagaagg agattccccg gagcacgctg gactcgttca    1680
tgcagccgtt ccagagcaca ctgtggctgc tggtgggggct gtcggtgcac gtggtggccg    1740
tgatgctgta cctgctggac cgcttcagcc ccttcggccg gttcaaggtg aacagcgagg    1800
aggaggagga ggacgcactg accctgtcct cggccatgtg gttctcctgg ggcgtcctgc    1860
tcaactccgg catcggggaa ggcgccccca gaagcttctc agcgcgcatc ctgggcatgg    1920
tgtgggccgg ctttgccatg atcatcgtgg cctcctacac cgccaacctg gcggccttcc    1980
tggtgctgga ccggccggag gagcgcatca cgggcatcaa cgaccctcgg ctgaggaacc    2040
cctcggacaa gtttatctac gccacggtga agcagagctc cgtggatatc tacttccggc    2100
gccaggtgga gctgagcacc atgtaccggc atatggagaa gcacaactac gagagtgcgg    2160
cggaggccat ccaggccgtg agagacaaca agctgcatgc cttcatctgg gactcggcgg    2220
tgctggagtt cgaggcctcg cagaagtgcg acctggtgac gactggagag ctgtttttcc    2280
gctcgggctt cggcataggc atgcgcaaag acagccctg gaagcagaac gtctccctgt    2340
ccatcctcaa gtcccacgag aatggcttca tggaagacct ggacaagacg tgggttcggt    2400
atcaggaatg tgactcgcgc agcaacgccc ctgcgaccct tacttttgag aacatggccg    2460
gggtcttcat gctggtagct ggggggcatcg tggccgggat cttcctgatt ttcatcgaga    2520
ttgcctacaa gcggcacaag gatgctcgcc ggaagcagat gcagctggcc tttgccgccg    2580
ttaacgtgtg gcggaagaac ctgcagcagt accatcccac tgatatcacg ggcccgctca    2640
acctctcaga tccctcggtc agcaccgtgg tgtgaggccc ccggaggcgc ccacctgccc    2700
agttagcccg gccaaggaca ctgatgggtc ctgctgctcg ggaaggcctg agggaagccc    2760
acccgcccca gagactgccc accctgggcc tcccgtccgt ccgcccgccc accccgctgc    2820
ctggcgggca gcccctgctg gaccaaggtg cggaccggag cggctgagga cggggcagag    2880
ctgagtcggc tgggcagggc cgcagggcgc tccggcagag gcagggccct ggggtctctg    2940
agcagtgggg agcggggggct aactggcccc aggcggaggg gcttggagca gagacggcag    3000
ccccatcctt cccgcagcac cagcctgagc cacagtgggg cccatggccc cagctggctg    3060
ggtcgcccct cctcgggcgc ctgcgctcct ctgcagcctg agctccaccc tccctcttc    3120 ttgcggcacc gcccacccac accccgtctg ccccttgacc ccacacgccg gggctggccc    3180
tgccctcccc cacggccgtc cctgacttcc cagctgcagc gcctcccgcc gcctcgggcc    3240
gcctc                                                              3245
```

```
<210> SEQ ID NO 7
<211> LENGTH: 42
<212> TYPE: DNA
<213> ORGANISM: Artificial Sequence
<220> FEATURE:
<223> OTHER INFORMATION: CAAR component

<400> SEQUENCE: 7
gcgtcgaccg gcggaggatc tggcggaggc ggatcttctg gc                        42

<210> SEQ ID NO 8
<211> LENGTH: 72
<212> TYPE: DNA
<213> ORGANISM: Artificial Sequence
<220> FEATURE:
<223> OTHER INFORMATION: CAAR component

<400> SEQUENCE: 8
atctatatct gggctcctct ggccggcaca tgcggagttc tgctgctgag cctggtcatc        60
```

-continued accctgtact gc                                                                 72

<210> SEQ ID NO 9
<211> LENGTH: 177
<212> TYPE: DNA
<213> ORGANISM: Artificial Sequence
<220> FEATURE:
<223> OTHER INFORMATION: CAAR component

<400> SEQUENCE: 9
ttctggctgc ctattggctg cgccgccttt gtggtcgtgt gtatcctggg ctgcatcctg        60
atctgctggc tgaccaagaa aaagtacagc agcagcgtgc acgaccccaa cggcgagtac       120
atgttcatga gagccgtgaa caccgccaag aagtccagac tgaccgacgt gacactg         177

<210> SEQ ID NO 10
<211> LENGTH: 126
<212> TYPE: DNA
<213> ORGANISM: Artificial Sequence
<220> FEATURE:
<223> OTHER INFORMATION: CAAR component

<400> SEQUENCE: 10
aagcggggca gaaagaagct gctgtacatc ttcaagcagc ccttcatgcg gcccgtgcag        60
acaacccaag aggaagatgg ctgctcctgc agattccctg aggaagagga aggcggctgc       120
gagctg                                                                   126

<210> SEQ ID NO 11
<211> LENGTH: 339
<212> TYPE: DNA
<213> ORGANISM: Artificial Sequence
<220> FEATURE:
<223> OTHER INFORMATION: CAAR component

<400> SEQUENCE: 11
agagtgaagt tctccagatc cgccgacgct cctgcttacc agcagggaca gaaccagctg        60
tataacgagc tgaacctggg cgcgcagaga gagtacgacg tgctggacaa gcggagaggc       120
agagatcctg agatgggcgg caagcccaga cggaagaatc ctcaagaggg cctgtacaac       180
gaactccaga agacaagat ggccgaggcc tacagcgaga tcggaatgaa gggcgagcgc        240
agaagaggca agggacacga tggactgtat caggggcctgt ctaccgccac caaggacacc      300
tatgatgccc tgcacatgca ggccctgcca cctagataa                              339

<210> SEQ ID NO 12
<211> LENGTH: 21
<212> TYPE: PRT
<213> ORGANISM: Artificial Sequence
<220> FEATURE:
<223> OTHER INFORMATION: CAAR component

<400> SEQUENCE: 12

Met Ala Leu Pro Val Thr Ala Leu Leu Leu Pro Leu Ala Leu Leu Leu
1               5                   10                  15

His Ala Ala Arg Pro
            20

<210> SEQ ID NO 13
<211> LENGTH: 18
<212> TYPE: PRT
<213> ORGANISM: Artificial Sequence
<220> FEATURE:

-continued

<223> OTHER INFORMATION: CAAR component

<400> SEQUENCE: 13

Met Ser Thr Met Arg Leu Leu Thr Leu Ala Leu Leu Phe Ser Cys Ser
1               5                   10                  15

Val Ala

<210> SEQ ID NO 14
<211> LENGTH: 375
<212> TYPE: PRT
<213> ORGANISM: Homo sapiens

<400> SEQUENCE: 14

Arg Ala Ala Cys Asp Pro Lys Ile Val Asn Ile Gly Ala Val Leu Ser
1               5                   10                  15

Thr Arg Lys His Glu Gln Met Phe Arg Glu Ala Val Asn Gln Ala Asn
                20                  25                  30

Lys Arg His Gly Ser Trp Lys Ile Gln Leu Asn Ala Thr Ser Val Thr
            35                  40                  45

His Lys Pro Asn Ala Ile Gln Met Ala Leu Ser Val Cys Glu Asp Leu
        50                  55                  60

Ile Ser Ser Gln Val Tyr Ala Ile Leu Val Ser His Pro Pro Thr Pro
65                  70                  75                  80

Asn Asp His Phe Thr Pro Thr Pro Val Ser Tyr Thr Ala Gly Phe Tyr
                85                  90                  95

Arg Ile Pro Val Leu Gly Leu Thr Thr Arg Met Ser Ile Tyr Ser Asp
                100                 105                 110

Lys Ser Ile His Leu Ser Phe Leu Arg Thr Val Pro Pro Tyr Ser His
            115                 120                 125

Gln Ser Ser Val Trp Phe Glu Met Met Arg Val Tyr Ser Trp Asn His
        130                 135                 140

Ile Ile Leu Leu Val Ser Asp Asp His Glu Gly Arg Ala Ala Gln Lys
145                 150                 155                 160

Arg Leu Glu Thr Leu Leu Glu Glu Arg Glu Ser Lys Ala Glu Lys Val
                165                 170                 175

Leu Gln Phe Asp Pro Gly Thr Lys Asn Val Thr Ala Leu Leu Met Glu
                180                 185                 190

Ala Lys Glu Leu Glu Ala Arg Val Ile Ile Leu Ser Ala Ser Glu Asp
            195                 200                 205

Asp Ala Ala Thr Val Tyr Arg Ala Ala Ala Met Leu Asn Met Thr Gly
        210                 215                 220

Ser Gly Tyr Val Trp Leu Val Gly Glu Arg Glu Ile Ser Gly Asn Ala
225                 230                 235                 240

Leu Arg Tyr Ala Pro Asp Gly Ile Leu Gly Leu Gln Leu Ile Asn Gly
                245                 250                 255

Lys Asn Glu Ser Ala His Ile Ser Asp Ala Val Gly Val Val Ala Gln
            260                 265                 270

Ala Val His Glu Leu Leu Glu Lys Glu Asn Ile Thr Asp Pro Pro Arg
        275                 280                 285

Gly Cys Val Gly Asn Thr Asn Ile Trp Lys Thr Gly Pro Leu Phe Lys
        290                 295                 300

Arg Val Leu Met Ser Ser Lys Tyr Ala Asp Gly Val Thr Gly Arg Val
305                 310                 315                 320

Glu Phe Asn Glu Asp Gly Asp Arg Lys Phe Ala Asn Tyr Ser Ile Met
                325                 330                 335

```
Asn Leu Gln Asn Arg Lys Leu Val Gln Val Gly Ile Tyr Asn Gly Thr
            340                 345                 350

His Val Ile Pro Asn Asp Arg Lys Ile Ile Trp Pro Gly Gly Glu Thr
            355                 360                 365

Glu Lys Pro Arg Gly Tyr Gln
    370                 375

<210> SEQ ID NO 15
<211> LENGTH: 151
<212> TYPE: PRT
<213> ORGANISM: Homo sapiens

<400> SEQUENCE: 15

Met Ser Thr Arg Leu Lys Ile Val Thr Ile His Gln Glu Pro Phe Val
1               5                   10                  15

Tyr Val Lys Pro Thr Leu Ser Asp Gly Thr Cys Lys Glu Glu Phe Thr
            20                  25                  30

Val Asn Gly Asp Pro Val Lys Lys Val Ile Cys Thr Gly Pro Asn Asp
        35                  40                  45

Thr Ser Pro Gly Ser Pro Arg His Thr Val Pro Gln Cys Cys Tyr Gly
    50                  55                  60

Phe Cys Ile Asp Leu Leu Ile Lys Leu Ala Arg Thr Met Asn Phe Thr
65                  70                  75                  80

Tyr Glu Val His Leu Val Ala Asp Gly Lys Phe Gly Thr Gln Glu Arg
                85                  90                  95

Val Asn Asn Ser Asn Lys Lys Glu Trp Asn Gly Met Met Gly Glu Leu
            100                 105                 110

Leu Ser Gly Gln Ala Asp Met Ile Val Ala Pro Leu Thr Ile Asn Asn
        115                 120                 125

Glu Arg Ala Gln Tyr Ile Glu Phe Ser Lys Pro Phe Lys Tyr Gln Gly
    130                 135                 140

Leu Thr Ile Leu Val Lys Lys
145                 150

<210> SEQ ID NO 16
<211> LENGTH: 138
<212> TYPE: PRT
<213> ORGANISM: Homo sapiens

<400> SEQUENCE: 16

Arg Ile Thr Gly Ile Asn Asp Pro Arg Leu Arg Asn Pro Ser Asp Lys
1               5                   10                  15

Phe Ile Tyr Ala Thr Val Lys Gln Ser Ser Val Asp Ile Tyr Phe Arg
            20                  25                  30

Arg Gln Val Glu Leu Ser Thr Met Tyr Arg His Met Glu Lys His Asn
        35                  40                  45

Tyr Glu Ser Ala Ala Glu Ala Ile Gln Ala Val Arg Asp Asn Lys Leu
    50                  55                  60

His Ala Phe Ile Trp Asp Ser Ala Val Leu Glu Phe Glu Ala Ser Gln
65                  70                  75                  80

Lys Cys Asp Leu Val Thr Thr Gly Glu Leu Phe Phe Arg Ser Gly Phe
                85                  90                  95

Gly Ile Gly Met Arg Lys Asp Ser Pro Trp Lys Gln Asn Val Ser Leu
            100                 105                 110

Ser Ile Leu Lys Ser His Glu Asn Gly Phe Met Glu Asp Leu Asp Lys
        115                 120                 125
```

-continued

```
Thr Trp Val Arg Tyr Gln Glu Cys Asp Ser
    130             135

<210> SEQ ID NO 17
<211> LENGTH: 885
<212> TYPE: PRT
<213> ORGANISM: Homo sapiens

<400> SEQUENCE: 17

Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
            20                  25                  30

Leu Ser Thr Arg Lys His Glu Gln Met Phe Arg Glu Ala Val Asn Gln
        35                  40                  45

Ala Asn Lys Arg His Gly Ser Trp Lys Ile Gln Leu Asn Ala Thr Ser
    50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
            115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
            195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Ala Met Leu Asn Met
225                 230                 235                 240

Thr Gly Ser Gly Tyr Val Trp Leu Val Gly Glu Arg Glu Ile Ser Gly
                245                 250                 255

Asn Ala Leu Arg Tyr Ala Pro Asp Gly Ile Leu Gly Leu Gln Leu Ile
            260                 265                 270

Asn Gly Lys Asn Glu Ser Ala His Ile Ser Asp Ala Val Gly Val Val
    275                 280                 285

Ala Gln Ala Val His Glu Leu Leu Glu Lys Glu Asn Ile Thr Asp Pro
    290                 295                 300

Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
            325                 330                 335

Arg Val Glu Phe Asn Glu Asp Gly Asp Arg Lys Phe Ala Asn Tyr Ser
            340                 345                 350

Ile Met Asn Leu Gln Asn Arg Lys Leu Val Gln Val Gly Ile Tyr Asn
```

-continued

```
                355                    360                    365

Gly Thr His Val Ile Pro Asn Asp Arg Lys Ile Ile Trp Pro Gly Gly
    370                    375                    380

Glu Thr Glu Lys Pro Arg Gly Tyr Gln Met Ser Thr Arg Leu Lys Ile
385                    390                    395                    400

Val Thr Ile His Gln Glu Pro Phe Val Tyr Val Lys Pro Thr Leu Ser
                405                    410                    415

Asp Gly Thr Cys Lys Glu Glu Phe Thr Val Asn Gly Asp Pro Val Lys
                420                    425                    430

Lys Val Ile Cys Thr Gly Pro Asn Asp Thr Ser Pro Gly Ser Pro Arg
                435                    440                    445

His Thr Val Pro Gln Cys Cys Tyr Gly Phe Cys Ile Asp Leu Leu Ile
        450                    455                    460

Lys Leu Ala Arg Thr Met Asn Phe Thr Tyr Glu Val His Leu Val Ala
465                    470                    475                    480

Asp Gly Lys Phe Gly Thr Gln Glu Arg Val Asn Asn Ser Asn Lys Lys
                485                    490                    495

Glu Trp Asn Gly Met Met Gly Glu Leu Leu Ser Gly Gln Ala Asp Met
                500                    505                    510

Ile Val Ala Pro Leu Thr Ile Asn Asn Glu Arg Ala Gln Tyr Ile Glu
                515                    520                    525

Phe Ser Lys Pro Phe Lys Tyr Gln Gly Leu Thr Ile Leu Val Lys Lys
        530                    535                    540

Glu Ile Pro Arg Ser Thr Leu Asp Ser Phe Met Gln Pro Phe Gln Ser
545                    550                    555                    560

Thr Leu Trp Leu Leu Val Gly Leu Ser Val His Val Val Ala Val Met
                565                    570                    575

Leu Tyr Leu Leu Asp Arg Phe Ser Pro Phe Gly Arg Phe Lys Val Asn
        580                    585                    590

Ser Glu Glu Glu Glu Glu Asp Ala Leu Thr Leu Ser Ser Ala Met Trp
        595                    600                    605

Phe Ser Trp Gly Val Leu Leu Asn Ser Gly Ile Gly Glu Gly Ala Pro
    610                    615                    620

Arg Ser Phe Ser Ala Arg Ile Leu Gly Met Val Trp Ala Gly Phe Ala
625                    630                    635                    640

Met Ile Ile Val Ala Ser Tyr Thr Ala Asn Leu Ala Ala Phe Leu Val
                645                    650                    655

Leu Asp Arg Pro Glu Glu Arg Ile Thr Gly Ile Asn Asp Pro Arg Leu
                660                    665                    670

Arg Asn Pro Ser Asp Lys Phe Ile Tyr Ala Thr Val Lys Gln Ser Ser
        675                    680                    685

Val Asp Ile Tyr Phe Arg Arg Gln Val Glu Leu Ser Thr Met Tyr Arg
    690                    695                    700

His Met Glu Lys His Asn Tyr Glu Ser Ala Ala Glu Ala Ile Gln Ala
705                    710                    715                    720

Val Arg Asp Asn Lys Leu His Ala Phe Ile Trp Asp Ser Ala Val Leu
                725                    730                    735

Glu Phe Glu Ala Ser Gln Lys Cys Asp Leu Val Thr Thr Gly Glu Leu
                740                    745                    750

Phe Phe Arg Ser Gly Phe Gly Ile Gly Met Arg Lys Asp Ser Pro Trp
        755                    760                    765

Lys Gln Asn Val Ser Leu Ser Ile Leu Lys Ser His Glu Asn Gly Phe
    770                    775                    780
```

```
Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
            820                 825                 830

Ile Glu Ile Ala Tyr Lys Arg His Lys Asp Ala Arg Arg Lys Gln Met
        835                 840                 845

Gln Leu Ala Phe Ala Ala Val Asn Val Trp Arg Lys Asn Leu Gln Gln
    850                 855                 860

Tyr His Pro Thr Asp Ile Thr Gly Pro Leu Asn Leu Ser Asp Pro Ser
865                 870                 875                 880

Val Ser Thr Val Val
                885
```

```
<210> SEQ ID NO 18
<211> LENGTH: 14
<212> TYPE: PRT
<213> ORGANISM: Artificial Sequence
<220> FEATURE:
<223> OTHER INFORMATION: CAAR component

<400> SEQUENCE: 18

Ala Ser Thr Gly Gly Gly Ser Gly Gly Gly Gly Ser Ser Gly
1               5                   10
```

```
<210> SEQ ID NO 19
<211> LENGTH: 14
<212> TYPE: PRT
<213> ORGANISM: Artificial Sequence
<220> FEATURE:
<223> OTHER INFORMATION: CAAR component

<400> SEQUENCE: 19

Ala Ser Gly Gly Gly Gly Ser Gly Gly Gly Gly Ser Ser Gly
1               5                   10
```

```
<210> SEQ ID NO 20
<211> LENGTH: 24
<212> TYPE: PRT
<213> ORGANISM: Artificial Sequence
<220> FEATURE:
<223> OTHER INFORMATION: CAAR component

<400> SEQUENCE: 20

Ile Tyr Ile Trp Ala Pro Leu Ala Gly Thr Cys Gly Val Leu Leu Leu
1               5                   10                  15

Ser Leu Val Ile Thr Leu Tyr Cys
            20
```

```
<210> SEQ ID NO 21
<211> LENGTH: 59
<212> TYPE: PRT
<213> ORGANISM: Artificial Sequence
<220> FEATURE:
<223> OTHER INFORMATION: CAAR component

<400> SEQUENCE: 21

Phe Trp Leu Pro Ile Gly Cys Ala Ala Phe Val Val Val Cys Ile Leu
1               5                   10                  15

Gly Cys Ile Leu Ile Cys Trp Leu Thr Lys Lys Lys Tyr Ser Ser Ser
            20                  25                  30
```

Val His Asp Pro Asn Gly Glu Tyr Met Phe Met Arg Ala Val Asn Thr
        35                  40                  45

Ala Lys Lys Ser Arg Leu Thr Asp Val Thr Leu
    50                  55

<210> SEQ ID NO 22
<211> LENGTH: 42
<212> TYPE: PRT
<213> ORGANISM: Artificial Sequence
<220> FEATURE:
<223> OTHER INFORMATION: CAAR component

<400> SEQUENCE: 22

Lys Arg Gly Arg Lys Lys Leu Leu Tyr Ile Phe Lys Gln Pro Phe Met
1               5                  10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
        35                  40

<210> SEQ ID NO 23
<211> LENGTH: 112
<212> TYPE: PRT
<213> ORGANISM: Artificial Sequence
<220> FEATURE:
<223> OTHER INFORMATION: CAAR component

<400> SEQUENCE: 23

Arg Val Lys Phe Ser Arg Ser Ala Asp Ala Pro Ala Tyr Gln Gln Gly
1               5                  10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 24
<211> LENGTH: 2640
<212> TYPE: DNA
<213> ORGANISM: Artificial Sequence
<220> FEATURE:
<223> OTHER INFORMATION: CAAR construct

<400> SEQUENCE: 24
atggctctgc ctgtgacagc tctgctgctg cctctggccc tgctgctgca tgctgccaga        60
cctagagccg cctgcgatcc caagatcgtg aatatcggag ccgtgctgag cacccggaag       120
cacgagcaga tgttcagaga agccgtgaac caggccaaca agagacacgg cagctggaag       180
atccagctga acgccacaag cgtgacccac aagcctaacg ccattcagat ggccctgagc       240
gtgtgcgagg atctgatcag ctctcaggtg tacgccatcc tggtgtctca ccctccaaca       300
cctaacgacc acttcacccc tacacctgtg tcttacaccg ccggcttcta cagaatccct       360

-continued

```
gtgctgggcc tgaccaccag aatgagcatc tacagcgaca agagcatcca cctgagcttt      420
ctgcggaccg tgcctcctta cagccaccag tctagcgttt ggttcgagat gatgcgggtg      480
tacagctgga accacatcat cctgctggtg tccgacgacc acgaaggcag agccgctcag      540
aagagactgg aaaccctgct ggaagagaga gagtccaagg ccgagaaggt gctgcagttc      600
gatcccggca ccaagaacgt gacagccctg ctgatggaag ccaaagaact ggaagccaga      660
gtgatcatcc tgagcgcctc cgaagatgat gccgccaccg tgtatagagc cgccgctatg      720
ctgaatatga ccggcagcgg atacgtgtgg ctcgtgggcg agagagagat tagcggaaac      780
gccctgagat acgcccctga tggaatcctg ggactgcagc tgatcaacgg caagaacgag      840
agcgcccaca tctctgatgc cgtgggagtt gtggctcagg ccgtgcatga gctgctggaa      900
aaagagaaca tcaccgatcc tccacggggc tgcgtgggca acaccaacat ctggaaaaca      960
ggcccactgt tcaagcgggt gctgatgagc agcaaatacg ccgatggcgt gacaggccgg      1020
gtcgagttta tgaggacggg cgacagaaag ttcgccaact acagcatcat gaacctgcag      1080
aaccggaagc tggtgcaagt gggcatctac aacggcaccc acgtgatccc caacgaccgg      1140
aagattatct ggcctggcgg cgaaaccgag aagcccagag gctaccagat gagcaccaga      1200
ctgaagattg tgaccatcca ccaagagcct ttcgtgtacg tgaagcccac actgagcgac      1260
ggcacctgta agaagagtt caccgtcaac ggcgaccctg tgaagaaagt gatctgcaca      1320
ggccccaacg atacaagccc tggcagccct agacacaccg ttcctcagtg ctgctacggc      1380
ttctgcatcg acctgctgat caagctggcc cggaccatga acttcaccta cgaagtgcac      1440
ctggtggcca acggcaagtt tggcacacaa gagagagtga acaacagcaa caagaaagaa      1500
tggaacggca tgatgggcga gctgctgtct ggacaggccg acatgattgt ggcccctctg      1560
accatcaaca acgagcgggc ccagtacatc gagttcagca agccattcaa gtaccagggc      1620
ctgacaatcc tggtcaagaa aggcacccgg atcaccggca tcaacgaccc cagactgaga      1680
aatccctccg acaagttcat ctacgccaca gtgaagcaga gcagcgtgga catctacttc      1740
agacgccagg tggaactgag caccatgtac agacacatgg aaaagcacaa ctacgagtct      1800
gccgccgagg caatccaggc cgtcagagat aacaagctgc acgccttcat ctgggacagc      1860
gccgtgctgg aatttgaggc cagccagaag tgcgatctgg tcaccaccgg tgaactgttt      1920
ttcagaagcg gctttggcat cggcatgcgg aaggactctc cctggaagca gaatgtgtcc      1980
ctgagcatcc tgaagtctca cgagaacggc ttcatggaag atctggacaa gacctgggtc      2040
cgataccaag agtgcgatag cgcgtcgacc ggcggaggat ctggcggagg cggatcttct      2100
ggcatctata tctgggctcc tctggccggc acatgcggag ttctgctgct gagcctggtc      2160
atcaccctgt actgcaagcg gggcagaaag aagctgctgt acatcttcaa gcagcccttc      2220
atgcggcccg tgcagacaac ccaagaggaa gatggctgct cctgcagatt ccctgaggaa      2280
gaggaaggcg gctgcgagct gagagtgaag ttctccagat ccgccgacgc tcctgcttac      2340
cagcagggac agaaccagct gtataacgag ctgaacctgg ggcgcagaga agagtacgac      2400
gtgctggaca gcggagagg cagagatcct gagatgggcg gcaagcccag acggaagaat      2460
cctcaagagg gcctgtacaa cgaactccag aaagacaaga tggccgaggc ctacagcgag      2520
atcggaatga agggcgagcg cagaagaggc aagggacacg atggactgta tcagggcctg      2580
tctaccgcca ccaaggacac ctatgatgcc ctgcacatgc aggccctgcc acctagataa      2640
```

```
<210> SEQ ID NO 25
<211> LENGTH: 2220
```

-continued

<212> TYPE: DNA
<213> ORGANISM: Artificial Sequence
<220> FEATURE:
<223> OTHER INFORMATION: CAAR construct

<400> SEQUENCE: 25

```
atggctctgc ctgtgacagc tctgctgctg cctctggccc tgctgctgca tgctgccaga      60
cctagagccg cctgcgatcc caagatcgtg aatatcggag ccgtgctgag cacccggaag     120
cacgagcaga tgttcagaga agccgtgaac caggccaaca agagacacgg cagctggaag     180
atccagctga acgccacaag cgtgacccac aagcctaacg ccattcagat ggccctgagc     240
gtgtgcgagg atctgatcag ctctcaggtg tacgccatcc tggtgtctca ccctccaaca     300
cctaacgacc acttcacccc tacacctgtg tcttacaccg ccggcttcta cagaatccct     360
gtgctgggcc tgaccaccag aatgagcatc tacagcgaca agagcatcca cctgagcttt     420
ctgcggaccg tgcctcctta cagccaccag tctagcgttt ggttcgagat gatgcgggtg     480
tacagctgga accacatcat cctgctggtg tccgacgacc acgaaggcag agccgctcag     540
aagagactgg aaaccctgct ggaagagaga gagtccaagg ccgagaaggt gctgcagttc     600
gatcccggca ccaagaacgt gacagccctg ctgatggaag ccaaagaact ggaagccaga     660
gtgatcatcc tgagcgcctc cgaagatgat gccgccaccg tgtatagagc cgccgctatg     720
ctgaatatga ccggcagcgg atacgtgtgg ctcgtgggcg agagagagat tagcggaaac     780
gccctgagat acgcccctga tggaatcctg ggactgcagc tgatcaacgg caagaacgag     840
agcgcccaca tctctgatgc cgtgggagtt gtggctcagg ccgtgcatga gctgctggaa     900
aaagagaaca tcaccgatcc tccacggggc tgcgtgggca acaccaacat ctggaaaaca     960
ggcccactgt tcaagcgggt gctgatgagc agcaaatacg ccgatggcgt gacaggccgg    1020
gtcgagttta tgaggacggg cgacagaaag ttcgccaact acagcatcat gaacctgcag    1080
aaccggaagc tggtgcaagt gggcatctac aacggcaccc acgtgatccc caacgaccgg    1140
aagattatct ggcctggcgg cgaaaccgag aagcccagag ctaccagat gagcaccaga    1200 ctgaagattg tgaccatcca ccaagagcct ttcgtgtacg tgaagcccac actgagcgac    1260
ggcacctgta aagaagagtt caccgtcaac ggcgaccctg tgaagaaagt gatctgcaca    1320
ggccccaacg atacaagccc tggcagccct agacacaccg ttcctcagtg ctgctacggc    1380
ttctgcatcg acctgctgat caagctggcc cggaccatga acttcacta cgaagtgcac    1440 ctggtggccg acggcaagtt tggcacacaa gagagagtga acaacagcaa caagaaagaa    1500
tggaacggca tgatgggcga gctgctgtct ggacaggccg acatgattgt ggcccctctg    1560
accatcaaca cgagcgggc ccagtacatc gagttcagca agccattcaa gtaccagggc    1620
ctgacaatcc tggtcaagaa agcgtcgacc ggcggaggat ctggcggagg cggatcttct    1680
ggcatctata tctgggctcc tctggccggc acatgcggag ttctgctgct gagcctggtc    1740 atcacctgt actgcaagcg gggcagaaag aagctgctgt acatcttcaa gcagcccttc    1800
atgcggcccg tgcagacaac ccaagaggaa gatggctgct cctgcagatt ccctgaggaa    1860
gaggaaggcg gctgcgagct gagagtgaag ttctccagat ccgccgacgc tcctgcttac    1920
cagcagggac agaaccagct gtataacgag ctgaacctgg ggcgcagaga agagtacgac    1980
gtgctggaca gcggagagg cagagatcct gagatgggcg gcaagcccag acggaagaat    2040
cctcaagagg gcctgtacaa cgaactccag aaagacaaga tggccgaggc ctacagcgag    2100
atcggaatga agggcgagcg cagaagaggc aagggacacg atggactgta tcagggcctg    2160
```

-continued

```
tctaccgcca ccaaggacac ctatgatgcc ctgcacatgc aggccctgcc acctagataa    2220

<210> SEQ ID NO 26
<211> LENGTH: 1767
<212> TYPE: DNA
<213> ORGANISM: Artificial Sequence
<220> FEATURE:
<223> OTHER INFORMATION: CAAR construct

<400> SEQUENCE: 26
atggctctgc ctgtgacagc tctgctgctg cctctggccc tgctgctgca tgctgccaga      60
cctagagccg cctgcgatcc caagatcgtg aatatcggag ccgtgctgag cacccggaag     120
cacgagcaga tgttcagaga agccgtgaac caggccaaca agagacacgg cagctggaag     180
atccagctga cgccacaag cgtgacccac aagcctaacg ccattcagat ggccctgagc     240
gtgtgcgagg atctgatcag ctctcaggtg tacgccatcc tggtgtctca ccctccaaca     300
cctaacgacc acttcacccc tacacctgtg tcttacaccg ccggcttcta cagaatccct     360
gtgctgggcc tgaccaccag aatgagcatc tacagcgaca agagcatcca cctgagcttt     420
ctgcggaccg tgcctcctta cagccaccag tctagcgttt ggttcgagat gatgcgggtg     480
tacagctgga accacatcat cctgctggtg tccgacgacc acgaaggcag agccgctcag     540
aagagactgg aaaccctgct ggaagagaga gagtccaagg ccgagaaggt gctgcagttc     600
gatcccggca ccaagaacgt gacagccctg ctgatggaag ccaaagaact ggaagccaga     660
gtgatcatcc tgagcgcctc cgaagatgat gccgccaccg tgtatagagc cgccgctatg     720
ctgaatatga ccggcagcgg atacgtgtgg ctcgtgggcg agagagagat tagcggaaac     780
gccctgagat acgcccctga tggaatcctg ggactgcagc tgatcaacgg caagaacgag     840
agcgcccaca tctctgatgc cgtgggagtt gtggctcagg ccgtgcatga gctgctggaa     900
aaagagaaca tcaccgatcc tccacggggc tgcgtgggca acaccaacat ctggaaaaca     960
ggcccactgt tcaagcgggt gctgatgagc agcaaatacg ccgatggcgt gacaggccgg    1020
gtcgagttta tgaggacgg cgacagaaag ttcgccaact acagcatcat gaacctgcag    1080
aaccggaagc tggtgcaagt gggcatctac aacggcaccc acgtgatccc caacgaccgg    1140
aagattatct ggcctggcgg cgaaaccgag aagcccagag ctaccaggc gtcgaccggc    1200 ggaggatctg gcggaggcgg atcttctggc atctatatct gggctcctct ggccggcaca    1260
tgcggagttc tgctgctgag cctggtcatc accctgtact gcaagcgggg cagaaagaag    1320
ctgctgtaca tcttcaagca gcccttcatg cggcccgtgc agacaaccca agaggaagat    1380
ggctgctcct gcagattccc tgaggaagag gaaggcggct gcgagctgag agtgaagttc    1440
tccagatccg ccgacgctcc tgcttaccag caggacagaa accagctgta taacgagctg    1500
aacctggggc gcagagaaga gtacgacgtg ctggacaagc ggagaggcag agatcctgag    1560
atgggcggca gcccagacg gaagaatcct caagagggcc tgtacaacga actccagaaa    1620
gacaagatgg ccgaggccta cagcgagatc ggaatgaagg gcgagcgcag aagaggcaag    1680
ggacacgatg gactgtatca gggcctgtct accgccacca aggacaccta tgatgccctg    1740
cacatgcagg ccctgccacc tagataa                                         1767

<210> SEQ ID NO 27
<211> LENGTH: 1878
<212> TYPE: DNA
<213> ORGANISM: Artificial Sequence
<220> FEATURE:
<223> OTHER INFORMATION: CAAR construct
```

<400> SEQUENCE: 27
atggctctgc ctgtgacagc tctgctgctg cctctggccc tgctgctgca tgctgccaga          60
cctagagccg cctgcgatcc caagatcgtg aatatcggag ccgtgctgag cacccggaag         120
cacgagcaga tgttcagaga agccgtgaac caggccaaca agagacacgg cagctggaag         180
atccagctga cgccacaag cgtgacccac aagcctaacg ccattcagat ggccctgagc          240
gtgtgcgagg atctgatcag ctctcaggtg tacgccatcc tggtgtctca ccctccaaca         300
cctaacgacc acttcacccc tacacctgtg tcttacaccg ccggcttcta cagaatccct         360
gtgctgggcc tgaccaccag aatgagcatc tacagcgaca gagcatcca cctgagcttt          420 ctgcggaccg tgcctcctta cagccaccag tctagcgttt ggttcgagat gatgcgggtg         480
tacagctgga accacatcat cctgctggtg tccgacgacc acgaaggcag agccgctcag         540
aagagactgg aaaccctgct ggaagagaga gagtccaagg ccgagaaggt gctgcagttc         600
gatcccggca ccaagaacgt gacagccctg ctgatggaag ccaaagaact ggaagccaga         660
gtgatcatcc tgagcgcctc cgaagatgat gccgccaccg tgtatagagc cgccgctatg         720
ctgaatatga ccggcagcgg atacgtgtgg ctcgtgggcg agagagagat tagcggaaac         780
gccctgagat acgcccctga tggaatcctg ggactgcagc tgatcaacgg caagaacgag         840
agcgcccaca tctctgatgc cgtgggagtt gtggctcagg ccgtgcatga gctgctggaa         900
aaagagaaca tcaccgatcc tccacggggc tgcgtgggca acaccaacat ctggaaaaca         960
ggcccactgt tcaagcgggt gctgatgagc agcaaatacg ccgatggcgt gacaggccgg        1020
gtcgagttta tgaggacgg cgacagaaag ttcgccaact acagcatcat gaacctgcag         1080
aaccggaagc tggtgcaagt gggcatctac aacggcaccc acgtgatccc caacgaccgg        1140
aagattatct ggcctggcgg cgaaaccgag aagcccagag ctaccaggc tagcggcgga         1200 ggcggatctg tggcggagg atcttctgga ttctggctgc ctattggctg cgccgccttt        1260
gtggtcgtgt gtatcctggg ctgcatcctg atctgctggc tgaccaagaa aaagtacagc        1320
agcagcgtgc acgaccccaa cggcgagtac atgttcatga gagccgtgaa caccgccaag        1380
aagtccagac tgaccgacgt gacactgggc agcaagcggg aagaaagaa gctgctgtat        1440 atcttcaagc agcccttcat gcggcccgtg cagaccacac aagaggaaga tggctgctcc        1500
tgcagattcc ccgaggaaga agaaggcggc tgcgagctga gagtgaagtt cagcagatcc        1560
gctgacgccc ctgcctatca gcagggacag aaccagctgt acaacgagct gaacctgggg        1620
agaagagaag agtacgacgt gctggacaag cggagaggca gagatcctga gatgggcggc        1680
aagcccagac ggaagaatcc tcaagagggc ctgtataatg agctgcagaa agacaagatg        1740
gccgaggcct acagcgagat cggaatgaag ggcgagcgca gaagaggcaa gggacacgat        1800
ggactgtacc agggcctgag caccgccacc aaggatacct atgatgccct gcacatgcag        1860 gccctgccctc caagataa                                                     1878

<210> SEQ ID NO 28
<211> LENGTH: 879
<212> TYPE: PRT
<213> ORGANISM: Artificial Sequence
<220> FEATURE:
<223> OTHER INFORMATION: CAAR construct

<400> SEQUENCE: 28

Met Ala Leu Pro Val Thr Ala Leu Leu Leu Pro Leu Ala Leu Leu Leu
1               5                   10                  15

-continued

```
His Ala Ala Arg Pro Arg Ala Ala Cys Asp Pro Lys Ile Val Asn Ile
            20                  25                  30

Gly Ala Val Leu Ser Thr Arg Lys His Glu Gln Met Phe Arg Glu Ala
            35                  40                  45

Val Asn Gln Ala Asn Lys Arg His Gly Ser Trp Lys Ile Gln Leu Asn
    50                  55                  60

Ala Thr Ser Val Thr His Lys Pro Asn Ala Ile Gln Met Ala Leu Ser
65                  70                  75                  80

Val Cys Glu Asp Leu Ile Ser Ser Gln Val Tyr Ala Ile Leu Val Ser
            85                  90                  95

His Pro Pro Thr Pro Asn Asp His Phe Thr Pro Thr Pro Val Ser Tyr
            100                 105                 110

Thr Ala Gly Phe Tyr Arg Ile Pro Val Leu Gly Leu Thr Thr Arg Met
            115                 120                 125

Ser Ile Tyr Ser Asp Lys Ser Ile His Leu Ser Phe Leu Arg Thr Val
    130                 135                 140

Pro Pro Tyr Ser His Gln Ser Ser Val Trp Phe Glu Met Met Arg Val
145                 150                 155                 160

Tyr Ser Trp Asn His Ile Ile Leu Leu Val Ser Asp Asp His Glu Gly
            165                 170                 175

Arg Ala Ala Gln Lys Arg Leu Glu Thr Leu Leu Glu Glu Arg Glu Ser
            180                 185                 190

Lys Ala Glu Lys Val Leu Gln Phe Asp Pro Gly Thr Lys Asn Val Thr
            195                 200                 205

Ala Leu Leu Met Glu Ala Lys Glu Leu Glu Ala Arg Val Ile Ile Leu
    210                 215                 220

Ser Ala Ser Glu Asp Asp Ala Ala Thr Val Tyr Arg Ala Ala Ala Met
225                 230                 235                 240

Leu Asn Met Thr Gly Ser Gly Tyr Val Trp Leu Val Gly Glu Arg Glu
            245                 250                 255

Ile Ser Gly Asn Ala Leu Arg Tyr Ala Pro Asp Gly Ile Leu Gly Leu
            260                 265                 270

Gln Leu Ile Asn Gly Lys Asn Glu Ser Ala His Ile Ser Asp Ala Val
            275                 280                 285

Gly Val Val Ala Gln Ala Val His Glu Leu Leu Glu Lys Glu Asn Ile
    290                 295                 300

Thr Asp Pro Pro Arg Gly Cys Val Gly Asn Thr Asn Ile Trp Lys Thr
305                 310                 315                 320

Gly Pro Leu Phe Lys Arg Val Leu Met Ser Ser Lys Tyr Ala Asp Gly
            325                 330                 335

Val Thr Gly Arg Val Glu Phe Asn Glu Asp Gly Asp Arg Lys Phe Ala
            340                 345                 350

Asn Tyr Ser Ile Met Asn Leu Gln Asn Arg Lys Leu Val Gln Val Gly
            355                 360                 365

Ile Tyr Asn Gly Thr His Val Ile Pro Asn Asp Arg Lys Ile Ile Trp
    370                 375                 380

Pro Gly Gly Glu Thr Glu Lys Pro Arg Gly Tyr Gln Met Ser Thr Arg
385                 390                 395                 400

Leu Lys Ile Val Thr Ile His Gln Glu Pro Phe Val Tyr Val Lys Pro
            405                 410                 415

Thr Leu Ser Asp Gly Thr Cys Lys Glu Glu Phe Thr Val Asn Gly Asp
            420                 425                 430
```

-continued

```
Pro Val Lys Lys Val Ile Cys Thr Gly Pro Asn Asp Thr Ser Pro Gly
        435             440             445

Ser Pro Arg His Thr Val Pro Gln Cys Cys Tyr Gly Phe Cys Ile Asp
    450                 455             460

Leu Leu Ile Lys Leu Ala Arg Thr Met Asn Phe Thr Tyr Glu Val His
465                 470              475             480

Leu Val Ala Asp Gly Lys Phe Gly Thr Gln Glu Arg Val Asn Asn Ser
                485             490              495

Asn Lys Lys Glu Trp Asn Gly Met Met Gly Glu Leu Leu Ser Gly Gln
            500             505             510

Ala Asp Met Ile Val Ala Pro Leu Thr Ile Asn Asn Glu Arg Ala Gln
        515             520             525

Tyr Ile Glu Phe Ser Lys Pro Phe Lys Tyr Gln Gly Leu Thr Ile Leu
        530             535             540

Val Lys Lys Gly Thr Arg Ile Thr Gly Ile Asn Asp Pro Arg Leu Arg
545             550             555             560

Asn Pro Ser Asp Lys Phe Ile Tyr Ala Thr Val Lys Gln Ser Ser Val
                565             570             575

Asp Ile Tyr Phe Arg Arg Gln Val Glu Leu Ser Thr Met Tyr Arg His
            580             585             590

Met Glu Lys His Asn Tyr Glu Ser Ala Ala Glu Ala Ile Gln Ala Val
            595             600             605

Arg Asp Asn Lys Leu His Ala Phe Ile Trp Asp Ser Ala Val Leu Glu
        610             615             620

Phe Glu Ala Ser Gln Lys Cys Asp Leu Val Thr Thr Gly Glu Leu Phe
625             630             635             640

Phe Arg Ser Gly Phe Gly Ile Gly Met Arg Lys Asp Ser Pro Trp Lys
            645             650             655

Gln Asn Val Ser Leu Ser Ile Leu Lys Ser His Glu Asn Gly Phe Met
            660             665             670

Glu Asp Leu Asp Lys Thr Trp Val Arg Tyr Gln Glu Cys Asp Ser Ala
        675             680             685

Ser Thr Gly Gly Gly Ser Gly Gly Gly Ser Ser Gly Ile Tyr Ile
        690             695             700

Trp Ala Pro Leu Ala Gly Thr Cys Gly Val Leu Leu Leu Ser Leu Val
705             710             715             720

Ile Thr Leu Tyr Cys Lys Arg Gly Arg Lys Lys Leu Leu Tyr Ile Phe
            725             730             735

Lys Gln Pro Phe Met Arg Pro Val Gln Thr Thr Gln Glu Glu Asp Gly
            740             745             750

Cys Ser Cys Arg Phe Pro Glu Glu Glu Gly Gly Cys Glu Leu Arg
        755             760             765

Val Lys Phe Ser Arg Ser Ala Asp Ala Pro Ala Tyr Gln Gln Gly Gln
770             775             780

Asn Gln Leu Tyr Asn Glu Leu Asn Leu Gly Arg Arg Glu Glu Tyr Asp
785             790             795             800

Val Leu Asp Lys Arg Arg Gly Arg Asp Pro Glu Met Gly Gly Lys Pro
            805             810             815

Arg Arg Lys Asn Pro Gln Glu Gly Leu Tyr Asn Glu Leu Gln Lys Asp
            820             825             830

Lys Met Ala Glu Ala Tyr Ser Glu Ile Gly Met Lys Gly Glu Arg Arg
        835             840             845

Arg Gly Lys Gly His Asp Gly Leu Tyr Gln Gly Leu Ser Thr Ala Thr
```

-continued

```
                850                    855                    860

Lys Asp Thr Tyr Asp Ala Leu His Met Gln Ala Leu Pro Pro Arg
865                    870                    875

<210> SEQ ID NO 29
<211> LENGTH: 739
<212> TYPE: PRT
<213> ORGANISM: Artificial Sequence
<220> FEATURE:
<223> OTHER INFORMATION: CAAR construct

<400> SEQUENCE: 29

Met Ala Leu Pro Val Thr Ala Leu Leu Leu Pro Leu Ala Leu Leu Leu
1               5                   10                  15

His Ala Ala Arg Pro Arg Ala Ala Cys Asp Pro Lys Ile Val Asn Ile
                20                  25                  30

Gly Ala Val Leu Ser Thr Arg Lys His Glu Gln Met Phe Arg Glu Ala
            35                  40                  45

Val Asn Gln Ala Asn Lys Arg His Gly Ser Trp Lys Ile Gln Leu Asn
        50                  55                  60

Ala Thr Ser Val Thr His Lys Pro Asn Ala Ile Gln Met Ala Leu Ser
65                  70                  75                  80

Val Cys Glu Asp Leu Ile Ser Ser Gln Val Tyr Ala Ile Leu Val Ser
                85                  90                  95

His Pro Pro Thr Pro Asn Asp His Phe Thr Pro Thr Pro Val Ser Tyr
                100                 105                 110

Thr Ala Gly Phe Tyr Arg Ile Pro Val Leu Gly Leu Thr Thr Arg Met
            115                 120                 125

Ser Ile Tyr Ser Asp Lys Ser Ile His Leu Ser Phe Leu Arg Thr Val
    130                 135                 140

Pro Pro Tyr Ser His Gln Ser Ser Val Trp Phe Glu Met Met Arg Val
145                 150                 155                 160

Tyr Ser Trp Asn His Ile Ile Leu Leu Val Ser Asp Asp His Glu Gly
                165                 170                 175

Arg Ala Ala Gln Lys Arg Leu Glu Thr Leu Leu Glu Glu Arg Glu Ser
            180                 185                 190

Lys Ala Glu Lys Val Leu Gln Phe Asp Pro Gly Thr Lys Asn Val Thr
            195                 200                 205

Ala Leu Leu Met Glu Ala Lys Glu Leu Glu Ala Arg Val Ile Ile Leu
    210                 215                 220

Ser Ala Ser Glu Asp Asp Ala Ala Thr Val Tyr Arg Ala Ala Ala Met
225                 230                 235                 240

Leu Asn Met Thr Gly Ser Gly Tyr Val Trp Leu Val Gly Glu Arg Glu
                245                 250                 255

Ile Ser Gly Asn Ala Leu Arg Tyr Ala Pro Asp Gly Ile Leu Gly Leu
                260                 265                 270

Gln Leu Ile Asn Gly Lys Asn Glu Ser Ala His Ile Ser Asp Ala Val
            275                 280                 285

Gly Val Val Ala Gln Ala Val His Glu Leu Leu Glu Lys Glu Asn Ile
        290                 295                 300

Thr Asp Pro Pro Arg Gly Cys Val Gly Asn Thr Asn Ile Trp Lys Thr
305                 310                 315                 320

Gly Pro Leu Phe Lys Arg Val Leu Met Ser Ser Lys Tyr Ala Asp Gly
                325                 330                 335

Val Thr Gly Arg Val Glu Phe Asn Glu Asp Gly Asp Arg Lys Phe Ala
```

-continued

```
            340             345             350

Asn Tyr Ser Ile Met Asn Leu Gln Asn Arg Lys Leu Val Gln Val Gly
        355             360             365

Ile Tyr Asn Gly Thr His Val Ile Pro Asn Asp Arg Lys Ile Ile Trp
    370             375             380

Pro Gly Gly Glu Thr Glu Lys Pro Arg Gly Tyr Gln Met Ser Thr Arg
385             390             395             400

Leu Lys Ile Val Thr Ile His Gln Glu Pro Phe Val Tyr Val Lys Pro
                405             410             415

Thr Leu Ser Asp Gly Thr Cys Lys Glu Glu Phe Thr Val Asn Gly Asp
            420             425             430

Pro Val Lys Lys Val Ile Cys Thr Gly Pro Asn Asp Thr Ser Pro Gly
        435             440             445

Ser Pro Arg His Thr Val Pro Gln Cys Cys Tyr Gly Phe Cys Ile Asp
    450             455             460

Leu Leu Ile Lys Leu Ala Arg Thr Met Asn Phe Thr Tyr Glu Val His
465             470             475             480

Leu Val Ala Asp Gly Lys Phe Gly Thr Gln Glu Arg Val Asn Asn Ser
            485             490             495

Asn Lys Lys Glu Trp Asn Gly Met Met Gly Glu Leu Leu Ser Gly Gln
        500             505             510

Ala Asp Met Ile Val Ala Pro Leu Thr Ile Asn Asn Glu Arg Ala Gln
        515             520             525

Tyr Ile Glu Phe Ser Lys Pro Phe Lys Tyr Gln Gly Leu Thr Ile Leu
    530             535             540

Val Lys Lys Ala Ser Thr Gly Gly Gly Ser Gly Gly Gly Ser Ser
545             550             555             560

Gly Ile Tyr Ile Trp Ala Pro Leu Ala Gly Thr Cys Gly Val Leu Leu
            565             570             575

Leu Ser Leu Val Ile Thr Leu Tyr Cys Lys Arg Gly Arg Lys Lys Leu
            580             585             590

Leu Tyr Ile Phe Lys Gln Pro Phe Met Arg Pro Val Gln Thr Thr Gln
        595             600             605

Glu Glu Asp Gly Cys Ser Cys Arg Phe Pro Glu Glu Glu Glu Gly Gly
    610             615             620

Cys Glu Leu Arg Val Lys Phe Ser Arg Ser Ala Asp Ala Pro Ala Tyr
625             630             635             640

Gln Gln Gly Gln Asn Gln Leu Tyr Asn Glu Leu Asn Leu Gly Arg Arg
            645             650             655

Glu Glu Tyr Asp Val Leu Asp Lys Arg Arg Gly Arg Asp Pro Glu Met
            660             665             670

Gly Gly Lys Pro Arg Arg Lys Asn Pro Gln Glu Gly Leu Tyr Asn Glu
            675             680             685

Leu Gln Lys Asp Lys Met Ala Glu Ala Tyr Ser Glu Ile Gly Met Lys
        690             695             700

Gly Glu Arg Arg Arg Gly Lys Gly His Asp Gly Leu Tyr Gln Gly Leu
705             710             715             720

Ser Thr Ala Thr Lys Asp Thr Tyr Asp Ala Leu His Met Gln Ala Leu
            725             730             735

Pro Pro Arg
```

<210> SEQ ID NO 30
<211> LENGTH: 588

-continued

<212> TYPE: PRT
<213> ORGANISM: Artificial Sequence
<220> FEATURE:
<223> OTHER INFORMATION: CAAR construct

<400> SEQUENCE: 30

Met Ala Leu Pro Val Thr Ala Leu Leu Leu Pro Leu Ala Leu Leu Leu
1               5                   10                  15

His Ala Ala Arg Pro Arg Ala Ala Cys Asp Pro Lys Ile Val Asn Ile
            20                  25                  30

Gly Ala Val Leu Ser Thr Arg Lys His Glu Gln Met Phe Arg Glu Ala
            35                  40                  45

Val Asn Gln Ala Asn Lys Arg His Gly Ser Trp Lys Ile Gln Leu Asn
        50                  55                  60

Ala Thr Ser Val Thr His Lys Pro Asn Ala Ile Gln Met Ala Leu Ser
65                  70                  75                  80

Val Cys Glu Asp Leu Ile Ser Ser Gln Val Tyr Ala Ile Leu Val Ser
                85                  90                  95

His Pro Pro Thr Pro Asn Asp His Phe Thr Pro Thr Pro Val Ser Tyr
            100                 105                 110

Thr Ala Gly Phe Tyr Arg Ile Pro Val Leu Gly Leu Thr Thr Arg Met
            115                 120                 125

Ser Ile Tyr Ser Asp Lys Ser Ile His Leu Ser Phe Leu Arg Thr Val
        130                 135                 140

Pro Pro Tyr Ser His Gln Ser Ser Val Trp Phe Glu Met Met Arg Val
145                 150                 155                 160

Tyr Ser Trp Asn His Ile Ile Leu Leu Val Ser Asp Asp His Glu Gly
                165                 170                 175

Arg Ala Ala Gln Lys Arg Leu Glu Thr Leu Leu Glu Glu Arg Glu Ser
            180                 185                 190

Lys Ala Glu Lys Val Leu Gln Phe Asp Pro Gly Thr Lys Asn Val Thr
            195                 200                 205

Ala Leu Leu Met Glu Ala Lys Glu Leu Glu Ala Arg Val Ile Ile Leu
        210                 215                 220

Ser Ala Ser Glu Asp Asp Ala Ala Thr Val Tyr Arg Ala Ala Ala Met
225                 230                 235                 240

Leu Asn Met Thr Gly Ser Gly Tyr Val Trp Leu Val Gly Glu Arg Glu
                245                 250                 255

Ile Ser Gly Asn Ala Leu Arg Tyr Ala Pro Asp Gly Ile Leu Gly Leu
            260                 265                 270

Gln Leu Ile Asn Gly Lys Asn Glu Ser Ala His Ile Ser Asp Ala Val
        275                 280                 285

Gly Val Val Ala Gln Ala Val His Glu Leu Leu Glu Lys Glu Asn Ile
        290                 295                 300

Thr Asp Pro Pro Arg Gly Cys Val Gly Asn Thr Asn Ile Trp Lys Thr
305                 310                 315                 320

Gly Pro Leu Phe Lys Arg Val Leu Met Ser Ser Lys Tyr Ala Asp Gly
                325                 330                 335

Val Thr Gly Arg Val Glu Phe Asn Glu Asp Gly Asp Arg Lys Phe Ala
            340                 345                 350

Asn Tyr Ser Ile Met Asn Leu Gln Asn Arg Lys Leu Val Gln Val Gly
        355                 360                 365

Ile Tyr Asn Gly Thr His Val Ile Pro Asn Asp Arg Lys Ile Ile Trp
        370                 375                 380

-continued

```
Pro Gly Gly Glu Thr Glu Lys Pro Arg Gly Tyr Gln Ala Ser Thr Gly
385             390             395             400

Gly Gly Ser Gly Gly Gly Gly Ser Ser Gly Ile Tyr Ile Trp Ala Pro
            405             410             415

Leu Ala Gly Thr Cys Gly Val Leu Leu Leu Ser Leu Val Ile Thr Leu
            420             425             430

Tyr Cys Lys Arg Gly Arg Lys Lys Leu Leu Tyr Ile Phe Lys Gln Pro
            435             440             445

Phe Met Arg Pro Val Gln Thr Thr Gln Glu Glu Asp Gly Cys Ser Cys
    450             455             460

Arg Phe Pro Glu Glu Glu Glu Gly Gly Cys Glu Leu Arg Val Lys Phe
465             470             475             480

Ser Arg Ser Ala Asp Ala Pro Ala Tyr Gln Gln Gly Gln Asn Gln Leu
            485             490             495

Tyr Asn Glu Leu Asn Leu Gly Arg Arg Glu Glu Tyr Asp Val Leu Asp
            500             505             510

Lys Arg Arg Gly Arg Asp Pro Glu Met Gly Gly Lys Pro Arg Arg Lys
            515             520             525

Asn Pro Gln Glu Gly Leu Tyr Asn Glu Leu Gln Lys Asp Lys Met Ala
    530             535             540

Glu Ala Tyr Ser Glu Ile Gly Met Lys Gly Glu Arg Arg Arg Gly Lys
545             550             555             560

Gly His Asp Gly Leu Tyr Gln Gly Leu Ser Thr Ala Thr Lys Asp Thr
            565             570             575

Tyr Asp Ala Leu His Met Gln Ala Leu Pro Pro Arg
            580             585

<210> SEQ ID NO 31
<211> LENGTH: 625
<212> TYPE: PRT
<213> ORGANISM: Artificial Sequence
<220> FEATURE:
<223> OTHER INFORMATION: CAAR construct

<400> SEQUENCE: 31

Met Ala Leu Pro Val Thr Ala Leu Leu Leu Pro Leu Ala Leu Leu Leu
1               5               10              15

His Ala Ala Arg Pro Arg Ala Ala Cys Asp Pro Lys Ile Val Asn Ile
            20              25              30

Gly Ala Val Leu Ser Thr Arg Lys His Glu Gln Met Phe Arg Glu Ala
            35              40              45

Val Asn Gln Ala Asn Lys Arg His Gly Ser Trp Lys Ile Gln Leu Asn
    50              55              60

Ala Thr Ser Val Thr His Lys Pro Asn Ala Ile Gln Met Ala Leu Ser
65              70              75              80

Val Cys Glu Asp Leu Ile Ser Ser Gln Val Tyr Ala Ile Leu Val Ser
            85              90              95

His Pro Pro Thr Pro Asn Asp His Phe Thr Pro Thr Pro Val Ser Tyr
            100             105             110

Thr Ala Gly Phe Tyr Arg Ile Pro Val Leu Gly Leu Thr Thr Arg Met
            115             120             125

Ser Ile Tyr Ser Asp Lys Ser Ile His Leu Ser Phe Leu Arg Thr Val
    130             135             140

Pro Pro Tyr Ser His Gln Ser Ser Val Trp Phe Glu Met Met Arg Val
145             150             155             160
```

```
Tyr Ser Trp Asn His Ile Ile Leu Leu Val Ser Asp Asp His Glu Gly
            165                 170                 175

Arg Ala Ala Gln Lys Arg Leu Glu Thr Leu Leu Glu Glu Arg Glu Ser
            180                 185                 190

Lys Ala Glu Lys Val Leu Gln Phe Asp Pro Gly Thr Lys Asn Val Thr
            195                 200                 205

Ala Leu Leu Met Glu Ala Lys Glu Leu Glu Ala Arg Val Ile Ile Leu
    210                 215                 220

Ser Ala Ser Glu Asp Asp Ala Ala Thr Val Tyr Arg Ala Ala Ala Met
225                 230                 235                 240

Leu Asn Met Thr Gly Ser Gly Tyr Val Trp Leu Val Gly Glu Arg Glu
            245                 250                 255

Ile Ser Gly Asn Ala Leu Arg Tyr Ala Pro Asp Gly Ile Leu Gly Leu
            260                 265                 270

Gln Leu Ile Asn Gly Lys Asn Glu Ser Ala His Ile Ser Asp Ala Val
            275                 280                 285

Gly Val Val Ala Gln Ala Val His Glu Leu Leu Glu Lys Glu Asn Ile
            290                 295                 300

Thr Asp Pro Pro Arg Gly Cys Val Gly Asn Thr Asn Ile Trp Lys Thr
305                 310                 315                 320

Gly Pro Leu Phe Lys Arg Val Leu Met Ser Ser Lys Tyr Ala Asp Gly
            325                 330                 335

Val Thr Gly Arg Val Glu Phe Asn Glu Asp Gly Asp Arg Lys Phe Ala
            340                 345                 350

Asn Tyr Ser Ile Met Asn Leu Gln Asn Arg Lys Leu Val Gln Val Gly
            355                 360                 365

Ile Tyr Asn Gly Thr His Val Ile Pro Asn Asp Arg Lys Ile Ile Trp
    370                 375                 380

Pro Gly Gly Glu Thr Glu Lys Pro Arg Gly Tyr Gln Ala Ser Gly Gly
385                 390                 395                 400

Gly Gly Ser Gly Gly Gly Gly Ser Ser Gly Phe Trp Leu Pro Ile Gly
            405                 410                 415

Cys Ala Ala Phe Val Val Val Cys Ile Leu Gly Cys Ile Leu Ile Cys
            420                 425                 430

Trp Leu Thr Lys Lys Lys Tyr Ser Ser Ser Val His Asp Pro Asn Gly
            435                 440                 445

Glu Tyr Met Phe Met Arg Ala Val Asn Thr Ala Lys Lys Ser Arg Leu
    450                 455                 460

Thr Asp Val Thr Leu Gly Ser Lys Arg Gly Arg Lys Lys Leu Leu Tyr
465                 470                 475                 480

Ile Phe Lys Gln Pro Phe Met Arg Pro Val Gln Thr Thr Gln Glu Glu
            485                 490                 495

Asp Gly Cys Ser Cys Arg Phe Pro Glu Glu Glu Glu Gly Gly Cys Glu
            500                 505                 510

Leu Arg Val Lys Phe Ser Arg Ser Ala Asp Ala Pro Ala Tyr Gln Gln
            515                 520                 525

Gly Gln Asn Gln Leu Tyr Asn Glu Leu Asn Leu Gly Arg Arg Glu Glu
            530                 535                 540

Tyr Asp Val Leu Asp Lys Arg Arg Gly Arg Asp Pro Glu Met Gly Gly
545                 550                 555                 560

Lys Pro Arg Arg Lys Asn Pro Gln Glu Gly Leu Tyr Asn Glu Leu Gln
            565                 570                 575

Lys Asp Lys Met Ala Glu Ala Tyr Ser Glu Ile Gly Met Lys Gly Glu
```

-continued

```
                580                585                590
Arg Arg Arg Gly Lys Gly His Asp Gly Leu Tyr Gln Gly Leu Ser Thr
          595                600                605

Ala Thr Lys Asp Thr Tyr Asp Ala Leu His Met Gln Ala Leu Pro Pro
    610                615                620

Arg
625

<210> SEQ ID NO 32
<211> LENGTH: 42
<212> TYPE: DNA
<213> ORGANISM: Artificial Sequence
<220> FEATURE:
<223> OTHER INFORMATION: CAAR component

<400> SEQUENCE: 32
gctagcggcg gaggcggatc tggtggcgga ggatcttctg ga                        42
```